US007691854B2

(12) United States Patent
Gielen-Haertwig et al.

(10) Patent No.: US 7,691,854 B2
(45) Date of Patent: Apr. 6, 2010

(54) DIHYDROPYRIDINE DERIVATIVES FOR USE AS HUMAN NEUTROPHIL ELASTASE INHIBITORS

(75) Inventors: Heike Gielen-Haertwig, Monheim (DE); Volkhart Min-Jian Li, Velbert (DE); Ulrich Rosentreter, Wuppertal (DE); Karl-Heinz Schlemmer, Wuppertal (DE); Swen Allerheiligen, Essen (DE); Leila Telan, Wuppertal (DE); Lars Bärfacker, Oberhausen (DE); Jörg Keldenich, Wuppertal (DE); Mary F. Fitzgerald, Yarnton (GB); Kevin Nash, Herts (GB); Barbara Albrecht, Wülfrath (DE); Dirk Meurer, Neustadt am Rübenberge (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 1059 days.

(21) Appl. No.: 10/525,867

(22) PCT Filed: Aug. 18, 2003

(86) PCT No.: PCT/EP03/09120

§ 371 (c)(1), (2), (4) Date: Mar. 13, 2006

(87) PCT Pub. No.: WO2004/020412

PCT Pub. Date: Mar. 11, 2004

(65) Prior Publication Data

US 2007/0167406 A1 Jul. 19, 2007

(30) Foreign Application Priority Data

Aug. 27, 2002 (GB) ................................ 0219896.8

(51) Int. Cl.

| | |
|---|---|
| ***A61K 31/44*** | (2006.01) |
| ***C07D 213/72*** | (2006.01) |
| ***C07D 401/02*** | (2006.01) |

(52) U.S. Cl. ............................. 514/235.2; 514/253.01; 514/340; 514/344; 514/352; 544/124; 544/360; 546/276.4; 546/289; 546/304

(58) Field of Classification Search ....................... None
See application file for complete search history.

(56) References Cited

U.S. PATENT DOCUMENTS 5,314,887 A 5/1994 Aldrich et al.

FOREIGN PATENT DOCUMENTS

| | | |
|---|---|---|
| GB | 2383326 | 6/2003 |
| WO | 03053930 | 7/2003 |

OTHER PUBLICATIONS

Kandeel et al, Journal fuer Praktische Chemie, 1984, 326(2), pp. 248-252.*

Erian, et al., "A Novel Synthesis of Fused Pyrazole Systems as Antimicrobial Agents," *Pharmazie*, 53 (11): 748-751 (1998).

* cited by examiner

*Primary Examiner*—Zinna N Davis
(74) *Attorney, Agent, or Firm*—Edwards Angell Palmer & Dodge LLP; Weiying Yang; Nicholas J. DiCeglie, Jr.

(57) ABSTRACT

The invention relates to novel dihydropyridine derivatives, of Formula (I) processes for their preparation, and their use in medicaments, especially for the treatment of chronic obstructive pulmonary diseases, acute coronary syndrome, acute myocardial infarction and heart failure development.

(I)

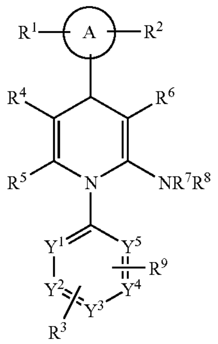

17 Claims, No Drawings

DIHYDROPYRIDINE DERIVATIVES FOR USE AS HUMAN NEUTROPHIL ELASTASE INHIBITORS

This application is a 371 of PCT/EP03/09120 filed Aug. 18, 2003.

The present invention relates to novel dihydropyridine derivatives, processes for their preparation, and their use in medicaments, especially for the treatment of chronic obstructive pulmonary diseases, acute coronary syndrome, acute myocardial infarction and heart failure development.

The fibrous protein elastin, which comprises an appreciable percentage of all protein content in some tissues, such as the arteries, some ligaments, the lungs and the heart, can be hydrolysed or otherwise destroyed by a select group of enzymes classified as elastases. Human leukocyte elastase (HLE, EC 3.4.21.37), also known as human neutrophil elastase (HNE), is a glycosylated, strongly basic serine protease and is found in the azurophilic granules of human polymorphonuclear leukocytes PMN). HNE is released from activated PMN and has been implicated causally in the pathogenesis of acute and chronic inflammatory diseases. HNE is capable of degrading a wide range of matrix proteins including elastin and collagen, and in addition to these actions on connective tissue HNE has a broad range of inflammatory actions including upregulation of IL-8 gene expression, oedema formation, mucus gland hyperplasia and mucus hypersecretion. It also acts as a mediator of tissue injury by hydrolysing collagen structures, e.g. in the heart after acute myocardial infarction or during the development of heart failure, thus damaging endothelial cells, promoting extravasation of neutrophils adhering to the endothelium and influencing the adhesion process itself.

Pulmonary diseases where HNE is believed to play a role include lung fibrosis, pneumonia, acute respiratory distress syndrome (ARDS), pulmonary emphysema, including smoking-induced emphysema, chronic obstructive pulmonary diseases (COPD) and cystic fibrosis. In cardiovascular diseases, HNE is involved in the enhanced generation of ischaemic tissue injury followed by myocardial dysfunction after acute myocardial infarction and in the remodelling processes occurring during the development of heart failure. HNE has also been causally implicated in rheumatoid arthritis, atherosclerosis, brain trauma, cancer and related conditions in which neutrophil participation is involved.

Thus, inhibitors of HLE activity can be potentially useful in the treatment of a number of inflammatory diseases, especially of chronic obstructive pulmonary diseases [R. A. Stockley, *Neutrophils and protease/antiprotease imbalance*, Am. J. Respir. Crit. Care 160, S49-S52 (1999)]. Inhibitors of HLE activity can also be potentially useful in the treatment of acute myocardial syndrome, unstable angina pectoris, acute myocardial infarction and coronary artery bypass grafts (CABG) [C. P. Tiefenbacher et al., *Inhibition of elastase improves myocardial function after repetitive ischaemia and myocardial infarction in the rat heart*, Eur. J. Physiol. 433, S563-S570 (1997); Dinerman et al, *Increased neutrophil elastase release in unstable angina pectoris and acute myocardial infarction*, J. Am. Coll. Cardiol. 15, 1559-1563 (1990)], of the development of heart failure [S. J. Gilbert et al., *Increased expression of promatrix metalloproteinase-9 and neutrophil elastase in canine dilated cardiomyopathy*, Cardiov. Res. 34, S377-S383 (1997)] and of atherosclerosis [Dollery et al., *Neutrophil elastase in human atherosclerotic plaque*, Circulation 107, 2829-2836 (2003)].

Ethyl 6-amino-1,4-bis(4-chlorophenyl)-5-cyano-2-methyl-1,4-dihydro-3-pyridinecarboxylate has been synthesized and tested for potential antimicrobial activity as described in A. W. Erian et al., *Pharmazie* 53 (11), 748-751 (1998).

The present invention relates to compounds of the general formula (I)

(I)

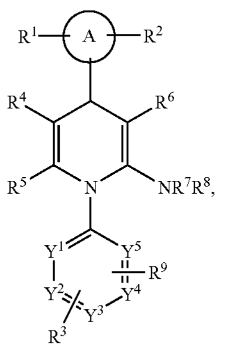

wherein

A represents an aryl or heteroaryl ring, $R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents $C_1$-$C_6$-alkoxycarbonyl, $C_1$-$C_6$-alkenoxycarbonyl, hydroxycarbonyl, aminocarbonyl, mono- or di-$C_1$-$C_4$-alkylaminocarbonyl, $C_6$-$C_{10}$-arylaminocarbonyl, heteroarylcarbonyl, heterocyclylcarbonyl or cyano, wherein $C_1$-$C_6$-alkoxycarbonyl, mono- and di-$C_1$-$C_4$-alkylaminocarbonyl can be substituted with one to three identical or different radicals selected from the group consisting of hydroxy, $C_1$-$C_4$-alkoxy, hydroxycarbonyl, $C_1$-$C_4$-alkoxycarbonyl, amino, mono- and di-$C_1$-$C_4$-alkylamino, aminocarbonyl, mono- and di-$C_1$-$C_4$-alkylaminocarbonyl, $C_1$-$C_4$-alkylcarbonylamino, heteroaryl, heterocyclyl and tri-($C_1$-$C_6$-alkyl)-silyl, $R^5$ represents $C_1$-$C_4$-alkyl, which can be substituted with one to three identical or different radicals selected from the group consisting of halogen, hydroxy, $C_1$-$C_6$-alkoxy, $C_1$-$C_6$-alkenoxy, $C_1$-$C_6$-alkylthio, amino, mono- and di-$C_1$-$C_6$-alkylamino, hydroxycarbonyl, $C_1$-$C_6$-alkoxycarbonyl and the radical —O—($C_1$-$C_4$)-alkyl-O—($C_1$-$C_4$)-alkyl, or $R^5$ represents $C_1$-$C_6$-alkoxycarbonyl, $R^6$ represents cyano, aminocarbonyl, mono- or di-$C_1$-$C_4$-alkylaminocarbonyl, $C_3$-$C_8$-cycloalkylaminocarbonyl, $C_1$-$C_6$-alkylcarbonyl, hydroxycarbonyl, $C_1$-$C_6$-alkoxycarbonyl, heteroaryl, heterocyclyl, heteroarylcarbonyl or heterocyclylcarbonyl, wherein mono- and di-$C_1$-$C_4$-alkylaminocarbonyl, $C_1$-$C_6$-alkylcarbonyl, $C_1$-$C_6$-alkoxycarbonyl, heteroaryl, heterocyclyl, heteroarylcarbonyl and heterocyclylcarbonyl can be substituted with one to three identical or different radicals selected from the group consisting of $C_1$-$C_4$-alkyl, hydroxy, $C_1$-$C_4$-alkoxy, hydroxycarbonyl, $C_1$-$C_4$-alkoxycarbonyl, amino, mono- and di-$C_1$-$C_4$-alkylamino, aminocarbonyl, mono- and di-$C_1$-$C_4$-alkylaminocarbonyl, $C_1$-$C_4$-alkylcarbonylamino, tri-($C_1$-$C_6$-alkyl)-silyl, phenyl and heteroaryl, $R^7$ represents hydrogen, $C_1$-$C_6$-alkyl, aminocarbonyl, mono- or di-$C_1$-$C_6$-alkylaminocarbonyl or $C_1$-$C_6$-alkoxycarbonyl, $R^8$ represents hydrogen or $C_1$-$C_6$-alkyl, $R^9$ represents hydrogen, halogen, nitro, cyano, trifluoromethyl, $C_1$-$C_6$-alkyl, hydroxy, $C_1$-$C_6$-alkoxy or trifluoromethoxy, wherein $C_1$-$C_6$-alkyl and $C_1$-$C_6$-alkoxy can be further substituted with one to three identical or different radicals selected from the group consisting of hydroxy and $C_1$-$C_4$-alkoxy, and $Y^1$, $Y^2$, $Y^3$, $Y^4$ and $Y^5$ independently from each other represent CH or N, wherein the ring contains either 0, 1 or 2 nitrogen atoms.

The compounds according to this invention can also be present in the form of their salts, hydrates and/or solvates.

Physiologically acceptable salts are preferred in the context of the present invention.

Physiologically acceptable salts according to the invention are non-toxic salts which in general are accessible by reaction of the compounds (I) with an inorganic or organic base or acid conventionally used for this purpose. Non-limiting examples of pharmaceutically acceptable salts of compounds (I) include the alkali metal salts, e.g. lithium, potassium and sodium salts, the alkaline earth metal salts such as magnesium and calcium salts, the quaternary ammonium salts such as, for example, triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydrochlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes.

Hydrates of the compounds of the invention or their salts are stoichiometric compositions of the compounds with water, such as for example hemi-, mono-, or dihydrates.

Solvates of the compounds of the invention or their salts are stoichiometric compositions of the compounds with solvents.

The present invention includes both the individual enantiomers or diastereomers and the corresponding racemates or diastereomeric mixtures of the compounds according to the invention and their respective salts. In addition, all possible tautomeric forms of the compounds described above are included according to the present invention. The diastereomeric mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl in general represents a straight-chain or branched hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, hexyl, isohexyl. The same applies to radicals such as alkoxy, alkylthio, alkylamino, alkoxycarbonyl and alkoxycarbonylamino.

Alkoxy illustratively and preferably represents methoxy, ethoxy, n-propoxy, iso-propoxy, tert.-butoxy, n-pentoxy and n-hexoxy.

Alkylcarbonyl in general represents a straight-chain or branched hydrocarbon radical having 1 to 6, preferably 1 to 4 carbon atoms which has a carbonyl function at the position of attachment. Non-limiting examples include formyl, acetyl, n-propionyl, n-butyryl, isobutyryl, pivaloyl, n-hexanoyl.

Alkoxycarbonyl illustratively and preferably represents methoxycarbonyl, ethoxycarbonyl, n-propoxycarbonyl, isopropoxycarbonyl, tert.-butoxycarbonyl, n-pentoxycarbonyl and n-hexoxycarbonyl.

Alkylamino represents an alkylamino radical having one or two (independently selected) alkyl substituents, illustratively and preferably representing methylamino, ethylamino, n-propylamino, isopropylamino, tert.-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

Alkylaminocarbonyl represents an alkylaminocarbonyl radical having one or two (independently selected) alkyl substituents, illustratively and preferably representing methylaminocarbonyl, ethylaminocarbonyl, n-propylaminocarbonyl, isopropylaminocarbonyl, tert.-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert.-butyl-N-methylaminocarbonyl, N-ethyl-N-n-pentylaminocarbonyl and N-n-hexyl-N-methylaminocarbonyl.

Cycloalkylaminocarbonyl represents a cycloalkylaminocarbonyl radical having one or two (independently selected) cycloakyl substituents with 3 to 8, preferably 4 to 6 ring carbon atoms which is bound via a carbonyl group, illustratively and preferably representing cyclopropylaminocarbonyl, cyclobutylaminocarbonyl, cyclopentylaminocarbonyl, cyclohexylaminocarbonyl and cycloheptylaminocarbonyl.

Aryl represents a mono- to tricyclic aromatic carbocyclic radical having generally 6 to 14 carbon atoms, illustratively and preferably representing phenyl, naphthyl and phenanthrenyl.

Heteroaryl per se and in heteroarylcarbonyl represents an aromatic mono- or bicyclic radical having generally 5 to 10 and preferably 5 or 6 ring atoms and up to 5 and preferably up to 4 hetero atoms selected from the group consisting of S, O and N, illustratively and preferably representing thienyl, furyl, pyrrolyl, thiazolyl, oxazolyl, imidazolyl, pyridyl, pyrimidyl, pyridazinyl, indolyl, indazolyl, benzofuranyl, benzothienyl, quinolinyl, isoquinolinyl.

Heteroarylcarbonyl illustratively and preferably represents thienylcarbonyl, furylcarbonyl, pyrrolylcarbonyl, thiazolylcarbonyl, oxazolylcarbonyl, imidazolylcarbonyl, pyridylcarbonyl, pyrimidylcarbonyl, pyridazinylcarbonyl, indolylcarbonyl, indazolylcarbonyl, benzofuranylcarbonyl, benzothienylcarbonyl, quinolinylcarbonyl, isoquinolinylcarbonyl.

Heterocyclyl per se and in heterocyclylcarbonyl represents a mono- or polycyclic, preferably mono- or bicyclic, nonaromatic heterocyclic radical having generally 4 to 10 and preferably 5 to 8 ring atoms and up to 3 and preferably up to 2 hetero atoms and/or hetero groups selected from the group consisting of N, O, S, SO and $SO_2$. The heterocyclyl radicals can be saturated or partially unsaturated. Preference is given to 5- to 8-membered monocyclic saturated heterocyclyl radicals having up to two hetero atoms selected from the group consisting of O, N and S, such as illustratively and preferably tetrahydrofuran-2-yl, pyrrolidin-2-yl, pyrrolidin-3-yl, pyrrolinyl, piperidinyl, morpholinyl, perhydroazepinyl.

Heterocyclylcarbonyl illustratively and preferably represents tetrahydrofuran-2-carbonyl, pyrrolidine-2-carbonyl, pyrrolidine-3-carbonyl, pyrrolinecarbonyl, piperidinecarbonyl, morpholinecarbonyl, perhydroazepinecarbonyl.

Halogen represents fluorine, chlorine, bromine and iodine.

When stated, that $Y^1$, $Y^2$, $Y^3$, $Y^4$ and $Y^5$ represent CH or N, CH shall also stand for a ring carbon atom, which is substituted with a substituent $R^3$ or $R^9$.

A * symbol next to a bond denotes the point of attachment in the molecule.

In another embodiment, the present invention relates to compounds of general formula (I), wherein A represents an aryl ring, $R^1$, $R^2$ and $R^3$ independently from each other represent hydrogen, methyl, ethyl, fluoro, chloro, bromo, nitro, cyano, trifluoromethyl or trifluoromethoxy, $R^4$ represents $C_1$-$C_6$-alkoxycarbonyl, $C_1$-$C_6$-alkenoxycarbonyl, hydroxycarbonyl, aminocarbonyl, mono- or di-$C_1$-$C_4$-alkylaminocarbonyl, heteroarylcarbonyl or cyano, wherein $C_1$-$C_6$-alkoxycarbonyl, mono- and di-$C_1$-$C_4$-alkylaminocarbonyl can be substituted with one to three identical or different radicals selected from the group consisting of hydroxy, $C_1$-$C_4$-alkoxy, $C_1$-$C_4$-alkoxycarbonyl, amino, mono- and di-$C_1$-$C_4$-alkylamino, heterocycle and tri-($C_1$-$C_6$-alkyl)-silyl, $R^5$ represents $C_1$-$C_4$-alkyl, which can be substituted with one to three identical or different radicals selected from the group consisting of halogen, $C_1$-$C_6$-alkoxy, $C_1$-$C_6$-alkenoxy, $C_1$-$C_6$-alkylthio and the radical —O—($C_1$-$C_4$)-alkyl-O—($C_1$-$C_4$)-alkyl, or $R^5$ represents $C_1$-$C_6$-alkoxycarbonyl, $R^6$ represents cyano, aminocarbonyl, mono- or di-$C_1$-$C_4$-alkylaminocarbonyl, $C_3$-$C_8$-cycloalkylaminocarbonyl, $C_1$-$C_6$-alkylcarbonyl, hydroxycarbonyl, $C_1$-$C_6$-alkoxycarbonyl, heteroaryl or heterocyclyl, wherein mono- and di-$C_1$-$C_4$-alkylaminocarbonyl, $C_1$-$C_6$-alkylcarbonyl, $C_1$-$C_6$-alkoxycarbonyl, heteroaryl and heterocyclyl can be substituted with one to three identical or different radicals selected from the group consisting of hydroxy, $C_1$-$C_4$-alkoxy and tri-($C_1$-$C_6$-alkyl)-silyl, or $R^6$ represents a moiety of the formula

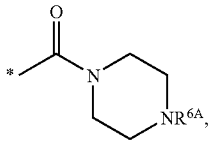
,
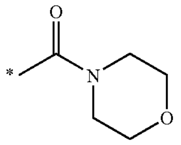
or
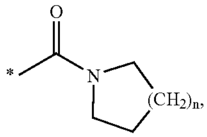
, wherein $R^{6A}$ is selected from the group consisting of hydrogen and $C_1$-$C_6$-alkyl, and n represents an integer of 1 or 2, $R^7$ represents hydrogen, $C_1$-$C_6$-alkyl, aminocarbonyl or mono- or di-$C_1$-$C_6$-alkylaminocarbonyl, $R^8$ represents hydrogen or $C_1$-$C_6$-alkyl, $R^9$ represents hydrogen, halogen, nitro, cyano, trifluoromethyl, trifluoromethoxy, methyl or ethyl, and $Y^1$, $Y^2$, $Y^3$, $Y^4$ and $Y^5$ each represent CH.

In another embodiment, the present invention relates to compounds according to general formula (I), wherein A is phenyl.

In another embodiment, the present invention relates to compounds according to general formula (I), wherein $R^1$ is hydrogen.

In another embodiment, the present invention relates to compounds according to general formula (I), wherein $R^2$ is cyano, especially wherein A is phenyl and $R^2$ is cyano located in para-position relative to the dihydropyridine ring.

In another embodiment, the present invention relates to compounds according to general formula (I), wherein $R^3$ is hydrogen In another embodiment, the present invention relates to compounds according to general formula (I), wherein $R^4$ is $C_1$-$C_6$-alkoxycarbonyl or cyano.

In another embodiment, the present invention relates to compounds according to general formula (I), wherein $R^5$ is methyl.

In another embodiment, the present invention relates to compounds according to general formula (I), wherein $R^6$ is cyano, aminocarbonyl, mono- or di-methyl- or -ethylaminocarbonyl, methoxycarbonyl or ethoxycarbonyl.

In another embodiment, the present invention relates to compounds according to general formula (I), wherein $R^7$ and/or $R^8$ is hydrogen.

In another embodiment, the present invention relates to compounds according to general formula (I), wherein $R^9$ is trifluoromethyl or nitro.

In another embodiment, the present invention relates to compounds of general formula (II)

(II)

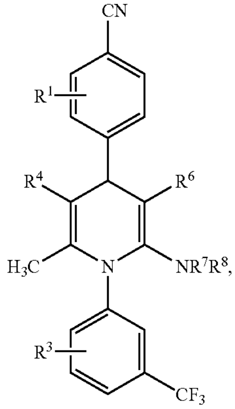
, wherein $R^1$, $R^3$, $R^4$, $R^6$, $R^7$ and $R^8$ have the meaning indicated above.

The compounds of the present invention can enolize into the corresponding imines:

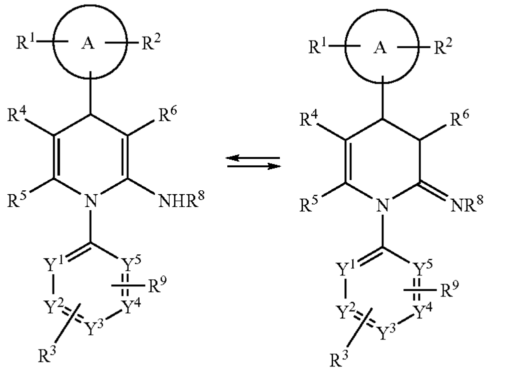

The compounds of general formula (I), wherein $R^7$ and $R^8$ represent hydrogen, can be synthesized by condensing compounds of general formula (III)

(III)

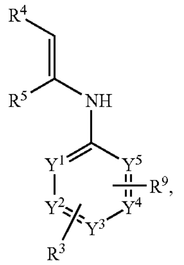

wherein $R^3$, $R^4$, $R^5$, $R^9$, and $Y^1$ to $Y^5$ have the meaning described above, in the presence of a base, in a three-component-reaction, with compounds of the general formulas (IV) and (V)

(IV)

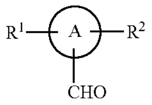

(V)

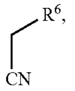

wherein $R^1$, $R^2$, $R^6$ and A have the meaning described above. Alternatively, in a first step compounds of the general formulas (IV) and (V) can be reacted, and the resulting product is reacted with or without isolation with compounds of the general formulas (III).

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is ethanol.

Suitable bases for the process are generally inorganic or organic bases. These preferably include cyclic amines, such as, for example, piperidine, morpholine, N-methylmorpholine, pyridine or 4-N,N-dimethylaminopyridine, or $(C_1-C_4)$-trialkyl-amines, such as, for example, triethylamine or diisopropylethylamine. Preference is given to piperidine. The base is employed in an amount from 0.1 mol to 10 mol, preferably from 0.1 mol to 1 mol, relative to 1 mol of the compound of the general formula (III).

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of general formula (III) can be synthesized by reacting compounds of general formula (VI)

(VI)

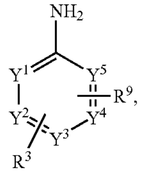

wherein $R^3$, $R^9$, and $Y^1$ to $Y^5$ have the meaning described above, in the presence of an acid with compounds of the general formula (VII)

(VII)

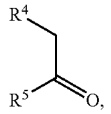

wherein $R^4$ and $R^5$ have the meaning described above.

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. For the process also acetic acid can be employed as solvent. It is also possible to use mixtures of the above-mentioned solvents. Preferred for the process is ethanol, toluene or benzene.

Suitable acids for the process are generally inorganic or organic acids. These preferably include carboxylic acids, such as, for example acetic acid or trifluoroacetic acid, or sulfonic acids, such as, for example, methanesulfonic acid or p-toluenesulfonic acid. Preference is given to acetic acid or trifluoroacetic acid. The acid is employed in an amount from 0.25 mol to 100 mol, relative to 1 mol of the compounds of the general formulas (VI) and (VII), respectively.

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of the general formulas (IV), (V), (VI) and (VII) are known per se, or they can be prepared by customary methods.

Compounds of the general formula (I), wherein $R^7$ represents an ureido (aminocarbonyl, mono- or di-$C_1$-$C_6$-alkylaminocarbonyl) group, can be synthesized by reacting compounds of the general formula (I), wherein $R^7$ represents hydrogen, with isocyanates (VIII):

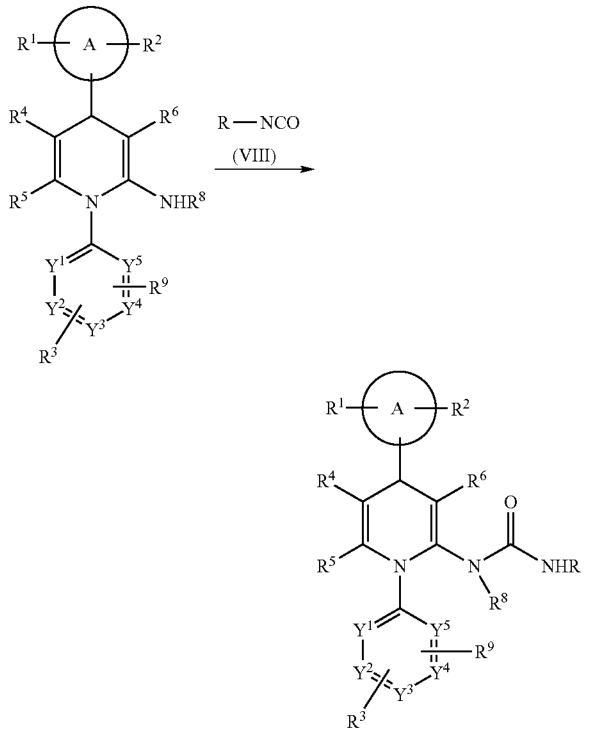

The compounds of general formula (I), wherein $R^7$ and/or $R^8$ are alkyl, can be synthesized by reacting compounds of general formula (I), wherein $R^7$ and $R^8$ are hydrogen, in the presence of a base with compounds of general formula (IX)

$X—R^7$ or $X—R^8$ (IX), wherein $R^7$ and $R^8$ are alkyl and X is a leaving group such as triflate or iodide.

Suitable solvents for the processes are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or hydrocarbons such as pentane, hexane, cyclohexane, benzene, toluene or xylene, or halogenohydrocarbons such as dichloromethane, dichloroethane, trichloromethane or chlorobenzene. It is also possible to use mixtures of the above-mentioned solvents. Preferred for the process is 1,2-dimethoxyethane or acetonitrile.

Suitable bases for the alkylation process are generally inorganic or organic bases. These preferably include cyclic amines, such as, for example, piperidine, morpholine, N-methylmorpholine, pyridine or 4-N,N-dimethylaminopyridine, or $(C_1$-$C_4)$-trialkylamines, such as, for example, triethylamine or diisopropylethylamine. Preference is given to diisopropylethylamine. The base is employed in an amount from 0.1 mol to 10 mol, preferably from 1 mol to 3 mol, relative to 1 mol of the compound of the general formula (I).

The processes are in general carried out in a temperature range from 0° C. to +150° C., preferably from 0° C. to +80° C.

The processes are generally carried out at normal pressure. However, it is also possible to carry them out at elevated pressure or at reduced pressure (for example in a range from 0.5 to 5 bar).

The above-mentioned method can be illustrated by the following scheme:

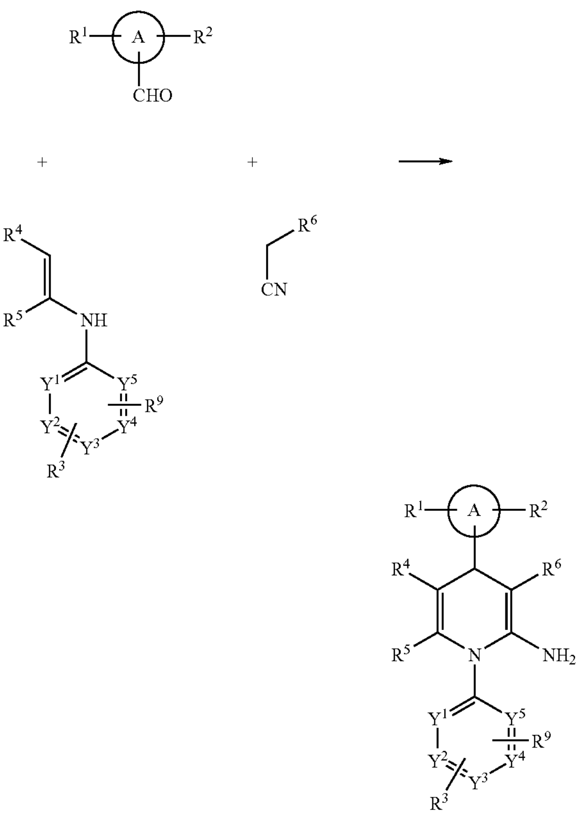

The compounds according to the invention exhibit an unforeseeable, useful pharmacological and pharmacokinetic activity spectrum. They are therefore suitable for use as medicaments for the treatment and/or prophylaxis of disorders in humans and animals.

Surprisingly, the compounds of the present invention show human neutrophil elastase (HNE) inhibitory activity and are therefore suitable for the preparation of medicaments for the treatment of diseases associated with HNE activity. They may thus provide an effective treatment of acute and chronic inflammatory processes, such as rheumatoid arthritis, atherosclerosis, and especially of acute and chronic pulmonary diseases, such as lung fibrosis, cystic fibrosis, pneumonia, acute respiratory distress syndrome (ARDS), in particular pulmonary emphysema, including smoking-induced emphysema, and chronic-obstructive pulmonary diseases (COPD), chronic bronchitis and bronchiectasis. The compounds of the present invention may further provide an effective treatment for cardiovascular ischaemic diseases such as acute coronary syndrome, acute myocardial infarction, unstable and stable angina pectoris, coronary artery bypass grafts (CABG) and heart failure development, for atherosclerosis, mitral valvular disease, atrial septal defects, percutaneous transluminal coronary angioplasty (PTCA), inflammation after open heart surgery and for pulmonary hypertension. They may also prove useful for an effective treatment of rheumatoid arthritis, acute inflammatory arthritis, cancer, acute pancreatitis, ulcerative colitis, periodontal disease, Chury-Strauss syndrome, acute and chronic atopic dermatitis, psoriasis, systemic lupus erythematosus, bullous pemphigus, sepsis, alcoholic hepatitis, liver fibrosis, Behcet's disease, allergic fungal sinusitis, allergic sinusitis, Crohn's disease, Kawasaki disease, glomerulonephritis, acute pyelonephritis, colorectal diseases, chronic suppurative otitis media, chronic venous leg ulcers, inflammatory bowel disease, bacterial and viral infections, brain trauma, stroke and other conditions in which neutrophil participation is involved.

The present invention further provides medicaments containing at least one compound according to the invention, preferably together with one or more pharmacologically safe excipient or carrier substances, and also their use for the abovementioned purposes.

The active component can act systemically and/or locally. For this purpose, it can be applied in a suitable manner, for example orally, parenterally, pulmonally, nasally, sublingually, lingually, buccally, rectally, transdermally, conjunctivally, otically or as an implant.

For these application routes, the active component can be administered in suitable application forms.

Useful oral application forms include application forms which release the active component rapidly and/or in modified form, such as for example tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include for example inhalatory pharmaceutical forms (including powder inhalers, nebulizers), nasal drops/solutions, sprays; tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders or implants.

The active components can be converted into the recited application forms in a manner known per se. This is carried out using inert non-toxic, pharmaceutically suitable excipients. These include inter alia carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

For human use, in the case of oral administration, it is recommendable to administer doses of from 0.001 to 50 mg/kg, preferably of 0.01 mg/kg to 20 mg/kg. In the case of parenteral administration, such as, for example, intravenously or via mucous membranes nasally, buccally or inhalationally, it is recommendable to use doses of 0.001 mg/kg to 0.5 mg/kg.

In spite of this, it can be necessary in certain circumstances to depart from the amounts mentioned, namely as a function of body weight, application route, individual behaviour towards the active component, manner of preparation and time or interval at which application takes place. It can for instance be sufficient in some cases to use less than the aforementioned minimum amount, while in other cases the upper limit mentioned will have to be exceeded. In the case of the application of larger amounts, it can be advisable to divide them into a plurality of individual doses spread through the day.

The percentages in the tests and examples which follows are, unless otherwise stated, by weight; parts are by weight. Solvent ratios, dilution ratios and concentrations reported for liquid/liquid solutions are each based on the volume.

A. EVALUATION OF PHYSIOLOGICAL ACTIVITY

The potential of the compounds of the invention to inhibit neutrophil elastase activity may be demonstrated, for example, using the following assays:

I. In Vitro Enzyme Assays of Human Neutrophil Elastase (HNE)

Assay Contents assay buffer: 0.1 M HEPES-NaOH buffer pH 7.4, 0.5 M NaCl, 0.1% (w/v) bovine serum albumin;

suitable concentration (see below) of HNE (18 U/mg lyophil., #20927.01, SERVA Electrophoresis GmbH, Heidelberg, Germany) in assay buffer;

suitable concentration (see below) of substrate in assay buffer;

suitable concentration of test compounds diluted with assay buffer from a 10 mM stock solution in DMSO.

EXAMPLE A

In Vitro Inhibition of HNE Using a Fluorogenic Peptide Substrate (Continuous Read-Out Signal, 384 MTP Assay Format):

In this protocol, the elastase substrate MeOSuc-Ala-Ala-Pro-Val-AMC (#324740, Calbiochem-Novabiochem Corporation, Merck KGaA, Darmstadt, Germany) is used. The test solution is prepared by mixing 10 µl of test compound dilution, 20 µl of HNE enzyme dilution (final concentration 8-0.4 µU/ml, routinely 2.1 µU/ml) and 20 µl of substrate dilution (final concentration 1 mM-1 µM, routinely 20 µM), respectively. The solution is incubated for 0-2 hrs at 37° C. (routinely one hour). The fluorescence of the liberated AMC due to the enzymatic reaction is measured at 37° C. (TECAN spectra fluor plus plate reader). The rate of increase of the fluorescence (ex. 395 nm, em. 460 nm) is proportional to elastase activity. $IC_{50}$ values are determined by RFU-versus-[I] plots. $K_m$ and $K_{m(app.)}$ values are determined by Lineweaver-Burk plots and converted to $K_i$ values by Dixon plots.

The preparation examples had $IC_{50}$ values within the range of 5 nM-5 µM in this assay. Representative data are given in Table 1:

TABLE 1

| Example No. | $IC_{50}$ [nM] |
|---|---|
| 2 | 30 |
| 4 | 27 |
| 12 | 90 |
| 25 | 40 |
| 43 | 800 |
| 44 | 130 |
| 47 | 500 |
| 50 | 10 |

EXAMPLE B

In Vitro Inhibition of HNE Using a Fluorogenic, Unsoluble Elastin Substrate (Discontinuous Read-Out Signal, 96 MTP Assay Format):

In this protocol the elastase substrate elastin-fluorescein (#100620, ICN Biomedicals GmbH, Eschwege, Germany) is used. The test solution is prepared by mixing 3 μl of test compound dilution, 77 μl of HNE enzyme dilution (final concentration 0.22 U/ml-2.2 mU/ml, routinely 21.7 μU/ml) and 80 μl substrate suspension (final concentration 2 mg/ml). The suspension is incubated for 0-16 hrs at 37° C. (routinely four hours) under slightly shaking conditions. To stop the enzymatic reaction, 160 μl of 0.1 M acetic acid are added to the test solution (final concentration 50 mM). The polymeric elastin-fluorescein is pulled down by centrifugation (Eppendorf 5804 centrifuge, 3.000 rpm, 10 min). The supernatant is transferred into a new MTP and the fluorescence of the liberated peptide fluorescein due to the enzymatic reaction is measured (BMG Fluostar plate reader). The rate of fluorescence (ex. 490 nm, em. 520 nm) is proportional to elastase activity. $IC_{50}$ values are determined by RFU-versus-[I] plots.

II. In Vitro Human Neutrophil Assays

EXAMPLE A

In Vitro PMN Elastolysis Assay:

This assay is used to determine the elastolytic potential of human polymorphonuclear cells (PMNs) and assess the proportion of degradation due to, neutrophil elastase [cf. Z. W. She et al., Am. J. Respir. Cell. Mol. Biol. 9, 386-392 (1993)].

Tritiated elastin, in suspension, is coated on to a 96 well plate at 10 μg per well. Test and reference [ZD-0892 (J. Med. Chem. 40, 1876-1885, 3173-3181 (1997), WO 95/21855) and α1 protease inhibitor (α1PI)] compounds are added to the wells at the appropriate concentrations. Human PMNs are separated from peripheral venous blood of healthy donors and resuspended in culture media. The neutrophils are added to the coated wells at concentrations ranging between $1\times10^6$ to $1\times10^5$ cells per well. Porcine pancreatic elastase (1.3 μM) is used as a positive control for the assay, and α1PI (1.2 μM) is used as the positive inhibitor of neutrophil elastase. The cellular control is PMNs without compound at each appropriate cell density. The cells plus compounds are incubated in a humidified incubator at 37° C. for 4 hours. The plates are centrifuged to allow the harvest of cell supernatant only. The supernatant is transferred in 75 μl volumes to corresponding wells of a 96 well Lumaplate™ (solid scintillant containing plates). The plates are dried until no liquid is visible in the wells and read in a beta counter for 3 minutes per well.

Elastolysis of the $^3$H-elastin results in an increase in counts in the supernatant. An inhibition of this elastolysis shows a decrease, from the cellular control, of tritium in the supernatant. α1PI gave 83.46±3.97% (mean±s.e.m.) inhibition at 1.2 μLM (n=3 different donors at $3.6\times10^5$ cells per well). $IC_{50}$ values were obtained for the reference compound ZD-0892 of 45.50±7.75 nM (mean±s.e.m.) (n=2 different donors at $3.6\times10^5$ cells per well).

Given that ZD-0892 is a selective inhibitor of PMN elastase along with the data from α1PI inhibition, these results indicate that the majority of elastin degradation by PMNs is due to the release of neutrophil elastase, and not to another elastolytic enzyme such as matrix metalloproteases (MMPs). The compounds of this invention are evaluated for their inhibitory activity in this HNE-dependent model of neutrophil elastolysis.

EXAMPLE B

In Vitro Inhibition of Membrane Bound Elastase:

Measurement of the inhibition of elastase bound to neutrophil membranes is performed using a human neutrophil assay. Neutrophils are stimulated with LPS at 37° C. for 35 min and then spun at 1600 rpm. Subsequently, the membrane bound elastase is fixed to the neutrophils with 3% paraformaldehyde and 0.25% glutaraldehyde for 3 min at 4° C. The neutrophils are then spun, and vehicle and the compound under evaluation are added, followed by addition of the substrate MeO-Suc-Ala-Ala-Pro-Val-AMC (#324740, Calbiochem-Novabiochem Corporation, Merck KGaA, Darmstadt, Germany) at 200 μM. Following a 25 min incubation at 37° C., the reaction is terminated with PMSF (phenylmethanesulfonyl fluoride), and the fluorescence is read at ex: 400 nm and em: 505 nm. $IC_{50}$ values are determined by interpolation from plots of relative fluorescence vs. inhibitor concentration.

III. In Vivo Models

EXAMPLE A

In Vivo Model of Acute Lung Injury in the Rat:

Instillation of human neutrophil elastase (HNE) into rat lung causes acute lung damage. The extent of this injury can be assessed by measuring lung haemorrhage.

Rats are anaesthetised with Hypnorm/Hypnovel/water and instilled with HNE or saline delivered by microsprayer into the lungs. Test compounds are administered by intravenous injection, by oral gavage or by inhalation at set times prior to the administration of HNE. Sixty minutes after the administration of elastase animals are killed by an anaesthetic overdose (sodium pentobarbitone) and the lungs lavaged with 2 ml heparinised phosphate buffered saline (PBS). Bronchoalveolar lavage (BAL) volume is recorded and the samples kept on ice. Each BAL sample is centrifuged at 900 r.p.m. for 10 minutes at 4-10° C. The supernatant is discarded and the cell pellet resuspended in PBS and the sample spun down again. The supernatant is again discarded and the cell pellet resuspended in 1 ml 0.1% cetyltrimethylammonium bromide (CTAB)/PBS to lyse the cells. Samples are frozen until blood content is assayed. Prior to the haemorrhage assay the samples are defrosted and mixed. 100 μl of each sample are placed into a separate well of a 96 well flat-bottomed plate. All samples are tested in duplicate. 100 μl 0.1% CTAB/PBS is included as a blank. The absorbance of the well contents is measured at 415 nm using a spectrophotometer. A standard curve is constructed by measuring the OD at 415 nm of different concentrations of blood in 0.1% CTAB/PBS. Blood content values are calculated by comparison to the standard curve (included in each plate) and normalised for the volume of BAL fluid retrieved.

The compounds of this invention are evaluated intravenously, orally or by inhalation for their inhibitory activity in this model of HNE-induced haemorrhage in the rat.

EXAMPLE B

In Vivo Model of Acute Myocardial Infarction in the Rat:

Elastase inhibitors are tested in a rat thread infarct model. Male Wistar rats (weighing>300 g) receive 10 mg/kg aspirin 30 min prior to surgery. They are anaesthetized by isofluran and ventilated (120-130 strokes/min, 200-250 μl stroke volume; MiniVent Type 845, Hugo Sachs Elektronik, Germany) during the whole surgery. Following a left thoracotomy at the fourth intercostal space, the pericardium is opened and the heart briefly exteriorized. A thread is turned around the left coronary artery (LAD) without occluding the artery. The thread is passed under the skin to the neck of the animal. The thorax is closed and the animal is allowed to recover for 4 days. At the fifth day, rats are anaesthetized with ether for 3 ml, and the thread is tied and the LAD occluded under ECG control. Test compounds are administered before or after LAD occlusion per os, intraperitoneally or intravenously (bolus or permanent infusion). After 1 hr occlusion, the thread is reopened to allow reperfusion. Hearts are excised, and infarct sizes are determined 48 hours later by staining of the re-occluded hearts with Evans blue, followed by TTC (triphenyltetrazolium chloride) staining of 2 mm heart sections. Normoxic (not occluded tissue) areas stain blue, ischemic (occluded but surviving tissue) areas stain red and necrotic (occluded dead tissue) areas remain white. Each tissue section is scanned and infarct sizes are determined by computer planimetry.

B. EXAMPLES

| Abbreviations: | |
|---|---|
| aq. | aqueous |
| Bp. | boiling point |
| DCI | direct chemical ionisation (for MS) |
| DMSO | dimethylsulfoxide |
| DMF | N,N-dimethylformamide |
| EI | electron impact ionisation (for MS) |
| ESI | electro-spray ionisation (for MS) |
| HPLC | high performance liquid chromatography |
| LC-MS | liquid chromatography coupled with mass spectroscopy |
| MS | mass spectroscopy |
| NMR | nuclear magnetic resonance |
| of th. | of theory (for yield) |
| $R_t$ | retention time (for HPLC) |
| THF | tetrahydrofuran |
| tlc | thin layer chromatography |

General Methods:

All reactions were carried out under an argon atmosphere unless otherwise noted.

Solvents were used as purchased from Aldrich without further purification. "Silica gel" or "Silica" refers to Silica gel 60 (0.040 mm-0.063 mm) from Merck KGaA company. Compounds purified over preparative HPLC were purified over a RP18-column with acetonitrile and water as the eluent, using a 1:9 to 9:1 gradient.

LC-MS and HPLC Methods:

Method 1 (LC-MS)

Instrument: Micromass Quattro LCZ, HP1100; Column: Symmetry C18, 50 mm×2.1 mm, 3.5 μm; Eluent A: acetonitrile+0.1% formic acid, Eluent B: water+0.1% formic acid; Gradient: 0.0 min 10% A→4.0 min 90% A→6.0 min 90% A; Oven: 40° C.; Flow: 0.5 ml/min; UV-detection: 208-400 nm Method 2 (LC-MS)

Instrument: Finnigan MAT 900S, TSP: P4000, AS3000, UV3000HR; Column: Symmetry C18, 150 mm×2.1 mm, 5.0 μm; Eluent A: acetonitrile, Eluent B: water+0.3 g 35% HCl, Eluent C: water; Gradient: 0.0 min 2% A→2.5 min 95% A→5 min 95% A; Oven: 70° C.; Flow: 1.2 ml/min; UV-detection: 210 nm Method 3 (LC-MS)

Instrument MS: Micromass ZQ; Instrument HPLC: Waters Alliance 2790; Column: Symmetry C18, 50 mm×2.1 mm, 3.5 μm; Eluent A: water+0.05% formic acid, Eluent B: acetonitrile+0.05% formic acid; Gradient: 0.0 min 10% B→3.5 min 90% B→5.5 min 90% B; Oven: 50° C.; Flow: 0.8 ml/min; UV-detection: 210 nm Method 4 (LC-MS)

Instrument: Micromass Quattro LCZ, HP1100; Column: Symmetry C18, 50 mm×2.1 mm, 3.5 μm; Eluent A: water+0.05% formic acid, Eluent B: acetonitrile+0.05% formic acid; Gradient: 0.0 min 90% A→4.0 min 10% A→6.0 min 10% A; Oven: 40° C.; Flow: 0.5 ml/min; UV-detection: 208-400 nm Method 5 (LC-MS)

Instrument: Micromass Platform LCZ, HP1100; Column: Symmetry C18, 150 mm×2.1 mm, 5 μm; Eluent A: water+0.05% formic acid, Eluent B: acetonitrile+0.05% formic acid; Gradient: 0.0 min 90% A→9.0 min 10% A→10.0 min 10% A; Oven: 40° C.; Flow: 0.5 ml/min; UV-detection: 208-400 nm Method 6 (LC-MS)

Instrument: Micromass Platform LCZ, HP1100; Column: Symmetry C18, 50 mm×2.1 mm, 3.5 μm; Eluent A: water+0.05% formic acid, Eluent B: acetonitrile+0.05% formic acid; Gradient: 0.0 min 90% A→4.0 min 10% A→6.0 min 10% A; Oven: 40° C.; Flow: 0.5 ml/min; UV-detection: 208-400 nm Method 7 (LC-MS)

Instrument: Waters Alliance 2790 LC; Column: Symmetry C18, 50 mm×2.1 mm, 3.5 μm; Eluent A: water+0.1% formic acid, Eluent B: acetonitrile+0.1% formic acid; Gradient: 0.0 min 5% B→5.0 min 10% B→6.0 min 10% B; Temperature: 50° C.; Flow: 1.0 ml/min; UV-detection: 210 nm Method 8 (HPLC)

Instrument: HP 1100 with DAD-detection; Column: Kromasil RP-18, 60 mm×2 mm, 3.5 μm; Eluent A: 5 ml $HClO_4$/l $H_2O$, Eluent B: acetonitrile; Gradient: 0 min 2% B, 0.5 min 2% B, 4.5 min 90% B, 6.5 min 90% B; Temperature: 30° C.; Flow: 0.75 ml/min; UV-detection: 210 nm Method 9 (HPLC)

Instrument: HP 1100 with DAD-detection; Column: Kromasil RP-18, 60 mm×2 mm, 3.5 μm; Eluent A: 5 ml $HClO_4$/l $H_2O$, Eluent B: acetonitrile; Gradient: 0 min 2% B, 0.5 min 2% B, 4.5 min 90% B, 15 min 90% B; Temperature: 30° C.; Flow: 0.75 ml/min; UV-detection: 210 nm Method 10 (LC-MS)

Instrument MS: Micromass ZQ; Instrument HPLC: Waters Alliance 2790; Column: Symmetry C18, 50 mm×2.1 mm, 3.5 μm; Eluent A: water+0.05% formic acid, Eluent B: acetonitrile+0.05% formic acid; Gradient: 0.0 min 5% B→4.5 min 90% B→5.5 min 90% B; Temperature: 50° C.; Flow: 1.0 ml/min; UV-detection: 210 nm.

Starting Materials:

Example 1A

Ethyl 3-{[3-(trifluoromethyl)phenyl]amino}-2-butenoate

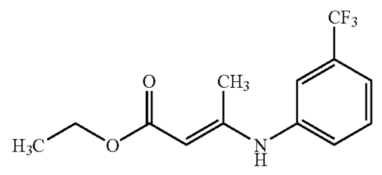

Method a):

4.0 g (31 mmol) Ethyl 3-oxobutanoate, 5.0 g (31 mmol) 3-trifluoromethylaniline and 1.86 g (31 mmol) acetic acid are dissolved in 50 ml toluene. The reaction mixture is refluxed overnight with a Dean-Stark trap to remove water. After cooling down to room temperature, the solvent is removed in vacuo and the residue is purified by column chromatography on silica with cyclohexane/ethylacetate mixtures as eluent.

Yield: 2.28 g (27% of th.) $^{1}$H-NMR (300 MHz, DMSO-$d_6$): δ=1.2 (t, 3H); 2.0 (s, 3H); 4.1 (q, 2H); 4.8 (s, 1H); 7.5 (m, 4H); 10.4 (s, 1H) ppm.

Method b):

3-Trifluoromethylaniline (2.50 g, 15.5 mmol) and ethyl acetoacetate (2.32 g, 17.8 mmol) are dissolved in absolute ethanol in a 500 ml round bottom flask equipped with a stir bar and a reflux condenser. Magnesium sulphate monohydrate (2.58 g, 18.6 mmol) and glacial acetic acid (14 mg, 0.23 mmol) are added. The suspension is stirred rigorously at reflux for 16 hours under an argon atmosphere. The crude reaction mixture is cooled to room temperature, filtered and concentrated in vacuo to give an oil. The oil is chromatographed over silica gel with cyclohexane/ethyl acetate mixtures as eluent to yield a pale yellow oil which is analytically pure.

Yield: 1 g (27% of th.)

Example 2A

3-{[3-(Trifluoromethyl)phenyl]amino}-2-butenenitrile

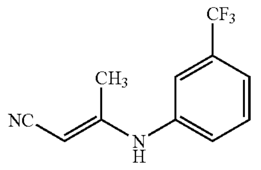

3-Aminocrotonitrile (1.0 g, 12.2 mmol), 3-trifluoromethylaniline (2.0 g, 12.4 mmol), and acetic acid (1.23 g, 20.5 mmol) are dissolved in water (8 ml). The reaction mixture is stirred at room temperature for 30 minutes. The mixture is extracted with toluene three times and the organic phase is dried over sodium sulfate. The solvent is removed in vacuo and the residue is purified by column chromatography on silica with cyclohexane/ethyl acetate mixtures as eluent.

Yield: 0.64 g (23% of th.) $^{1}$H-NMR (300 MHz, DMSO-$d_6$): δ=2.2(s, 3H);4.6 (s, 1H);7.4-7.6(m, 4H); 9.0 (s, 1H) ppm.

Example 3A

Ethyl 3-{[3-(trifluoromethyl)phenyl]amino}-2-hexenoate

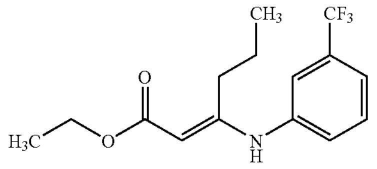

0.85 g (5.4 mmol) Ethyl 3-oxohexanoate, 1.0 g (6.21 mmol) 3-trifluoromethylaniline and 5 mg (0.08 mmol) acetic acid are dissolved in 15 ml ethanol, and 0.78 g (6.5 mmol) magnesium sulfate are added. The reaction mixture is stirred at reflux overnight. After cooling down to room temperature, the solvent is removed in vacuo and the residue is purified by column chromatography on silica with dichloromethane as eluent.

Yield: 0.55 g (34% of th.) $^{1}$H-NMR (300 MHz, DMSO-$d_6$): δ=0.8 (t, 3H); 1.2 (t, 3H); 1.4 (m, 2H); 2.3 (t, 2H); 4.1 (q, 2H); 4.8 (s, 1H); 7.4-7.6 (m, 4H); 10.3 (s, 1H) ppm.

Example 4A

(1R)-2-Methoxy-1-methyl-2-oxoethyl 3-oxobutanoate

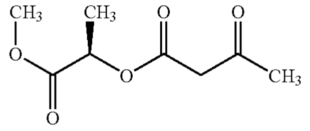

Methyl(2R)-2-hydroxypropanoate (5.0 g, 48 mmol) and triethylamine (49 mg, 0.48 mmol) are dissolved in toluene (40 ml). At 90° C., diketene (5.2 g, 62.4 mmol) is added dropwise. The reaction mixture is stirred at 100° C. for one hour. After cooling to room temperature, the mixture is poured into ice-water. The phases are separated and the aqueous phase is extracted with toluene two times. The combined organic phases are dried over sodium sulfate, the solvent is removed in vacuo and the residue is purified by column chromatography on silica with cyclohexane/ethyl acetate mixtures as eluent.

Yield: 8 g (89% of th.) $^{1}$H-NMR (300 MHz, DMSO-$d_6$): δ=1.4 (d, 3H); 2.2 (s, 3H); 3.7 (s, 3H, s, 2H); 5.1 (q, 1H) ppm.

Example 5A

Ethyl(3S)-3-(acetoacetyloxy)butanoate

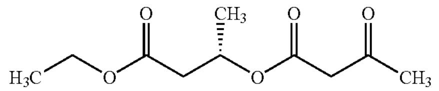

5.7 g (43.2 mmol) Ethyl(3S)-3-hydroxybutanoate and 44 mg (0.43 mmol) triethylamine are dissolved in 40 ml toluene. At 90° C., 4.7 g (56.1 mmol) diketene are added dropwise. The reaction mixture is stirred at 100° C. for one hour. After cooling down to room temperature, the mixture is poured into ice-water. The phases are separated and the aqueous phase is extracted two times with toluene. The combined organic phases are dried over sodium sulfate, the solvent is removed in vacuo and the residue is purified by column chromatography on silica with cyclohexane/ethyl acetate mixtures as eluent.

Yield: 7.1 g (77% of th.) $^{1}$H-NMR (300 MHz, DMSO-$d_6$): δ=1.2 (t, 3H, d, 3H); 2.2 (s, 3H); 2.6 (m, 2H); 3.6 (s, 2H); 4.1 (q, 2H); 5.2 (m, 1H) ppm.

Example 6A

1-Methyl-2-(4-morpholinyl)ethyl 3-oxobutanoate

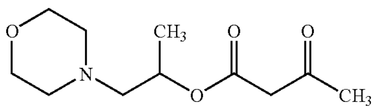

5.0 g (34.4 mmol) 1-(4-Morpholinyl)-2-propanol and 35 mg (0.34 mmol) triethylamine are dissolved in 40 ml toluene. At 90° C., 3.76 g (44.77 mmol) diketene are added dropwise. The reaction mixture is stirred at 100° C. for one hour. After cooling down to room temperature, the mixture is poured into ice-water. The phases are separated and the water phase is extracted two times with toluene. The combined organic phases are dried over sodium sulfate, the solvent is removed in vacuo and the residue is purified by column chromatography on silica with cyclohexane/ethyl acetate mixtures as eluent.

Yield: 5.34 g (68% of th.) $^{1}$H-NMR (200 MHz, DMSO-$d_6$): δ=1.2 (d, 3H); 2.2 (s, 3H); 2.3-2.4 (m, 6H); 3.5 (m, 6H); 5.1 (m, 1H) ppm.

In analogy to Example 3A, the following compounds are prepared:

| Ex.-No. | Structure | Yield [%] | $R_t$ [min] (method) | Mass $[M + H]^+$ |
|---|---|---|---|---|
| 7A | 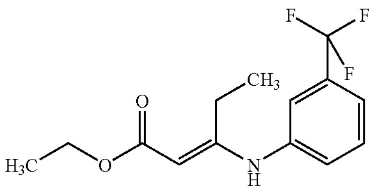 | 15 | 3.0 (8) | 288 |
| 8A | 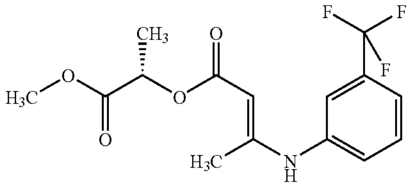 | 37 | 3.2 (8) | 332 |
| 9A | 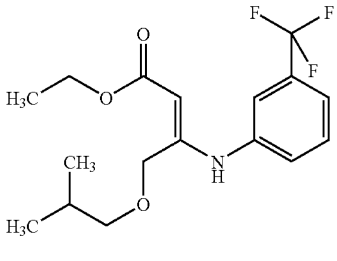 | 48 | 3.88 (3) | 346 |
| 10A | 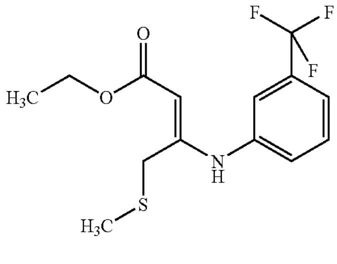 | 47 | 3.46 (3) | 320 |

-continued
| Ex.-No. | Structure | Yield [%] | $R_t$ [min] (method) | Mass $[M + H]^+$ |
|---|---|---|---|---|
| 11A | 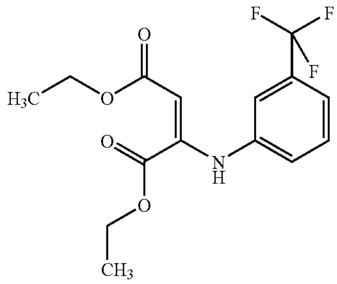 | 2 | 4.23 (7) | 332 |
| 12A | 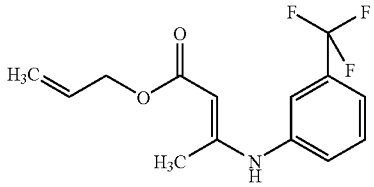 | 21 | 3.2 (8) | 285 $[M]^+$ |
| 13A | 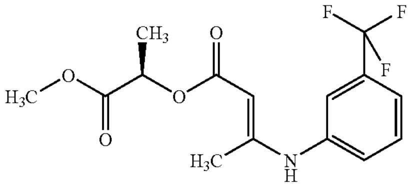 | 45 | 3.2 (8) | 332 |
| 14A | 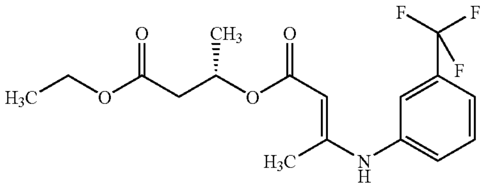 | 26 | 3.2 (8) | 360 |
| 15A | 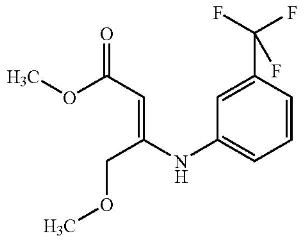 | 52 | 2.54 (7) | 290 |
| 16A | 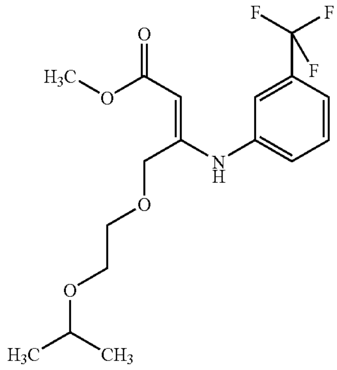 | 25 | 3.93 (7) | 362 |

-continued

| Ex.-No. | Structure | Yield [%] | $R_t$ [min] (method) | Mass $[M + H]^+$ |
|---|---|---|---|---|
| 17A | 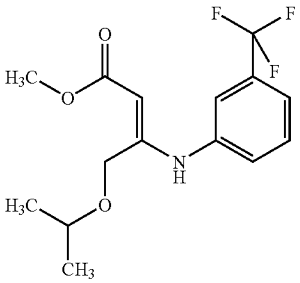 | 24 | 3.97 (7) | 318 |
| 18A | 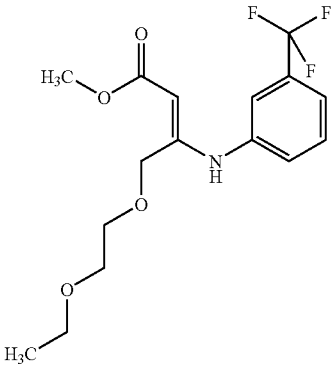 | 25 | 3.70 (7) | 348 |
| 19A | 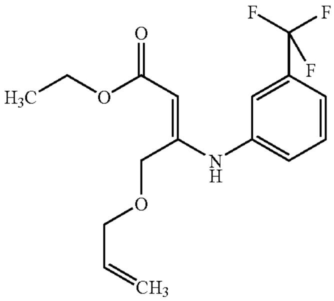 | 49 | 4.1 (7) | 330 |
| 20A | 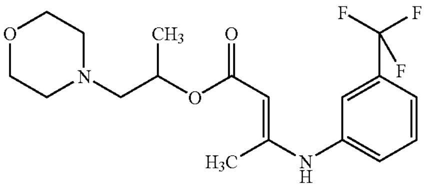 | 15 | 3.2 (8) | 373 |

Example 21A

3-(4-Morpholinyl)-3-oxopropanenitrile

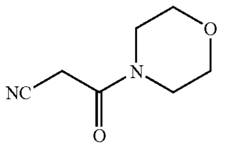

500 mg (5.88 mmol) Cyanoacetic acid are dissolved in 30 ml dimethylformamide, 563 mg (6.47 mmol) morpholine, 794 mg (5.88 mmol) 1-hydroxy-1H-benzotriazole hydrate and 718 mg (5.88 mmol) 4-dimethylaminopyridine are added. The reaction mixture is stirred at 0° C., then 1.12 g (5.88 mmol) 1-(3-dimethylaminopropyl)-3-ethylcarbodimide hydrochloride are added. The reaction mixture is stirred at room temperature for 18 hours, then water and ethyl acetate are added. The organic phase is dried over sodium sulfate and evaporated to dryness in vacuo. The residue is purified by preparative HPLC.

Yield: 249 mg (28% of th.) $^1$H-NMR (300 MHz, DMSO-$d_6$): δ=3.3 (m, 2H); 3.4 (m, 2H); 3.6 (m, 4H); 4.0 (s, 2H) ppm.

Example 22A

2-Cyano-N-(2-methoxyethyl)acetamide

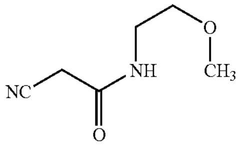

0.5 g (4.42 mmol) Ethyl cyanoacetate and 0.37 g (4.86 mmol) 2-methoxyethylamine are dissolved in 10 ml ethanol and stirred at reflux overnight. After cooling down to room temperature, the solvent is removed in vacuo and the product is crystallised from ethanol/diethylether.

Yield: 0.44 g (70% of th.) $^1$H-NMR (300 MHz, DMSO-$d_6$): δ=3.2 (s, 3H, m, 2H); 3.3 (m, 2H); 3.6 (s, 2H); 8.3 (s, 1H) ppm.

Example 23A

2-Cyano-N-propylacetamide

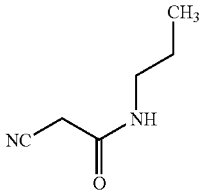

500 mg (5.88 mmol) Cyanoacetic acid are dissolved in 30 ml dimethylformamide, 382 mg (6.47 mmol) n-propylamine, 874 mg (6.47 mmol) 1-hydroxy-1H-benzotriazole hydrate and 718 mg (5.88 mmol) 4-dimethylaminopyridine are added. The reaction mixture is stirred at 0° C., then 1.24 g (6.47 mmol) 1-(3-dimethylaminopropyl)-3-ethylcarbodiimide hydrochloride are added. The reaction mixture is stirred at room temperature for 18 hours, then water and ethyl acetate are added. The organic phase is dried over sodium sulfate and evaporated to dryness in vacuo. The residue is purified by preparative HPLC.

Yield: 172 mg (23% of th.) $^1$H-NMR (200 MHz, DMSO-$d_6$): δ=0.8 (t, 3H); 1.4 (sext, 2H); 3.0 (q, 2H); 3.6 (s, 2H, 8.2 (s, 1H) ppm.

Example 24A

Ethyl 2-cyano-3-(5-cyano-2-pyridinyl)-2-propenoate

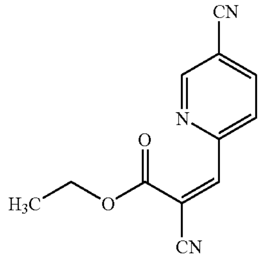

The compound of Example 33A (421 mg, 3.2 mmol), ethyl cyanoacetate (360 mg, 3.2 mmol) and piperidine (8.1 mg, 0.095 mmol) are dissolved in absolute ethanol (7.5 ml) and stirred at room temperature for 3 hours. During this time a precipitate is formed, which is filtered and washed with a minimal amount of additional ethanol (1 ml).

Yield: 395 mg (50% of th.) HPLC (method 8)=4.18 min MS (ESIpos): m/z=228 (M+H)$^+$ $^1$H-NMR (400 MHz, DMSO-$d_6$): δ=9.21 (d, 1H); 8.54 (dd, 1H); 8.46 (s, 1H); 8.12 (d, 1H); 4.35 (q, 2H); 1.32 (t, 3H) ppm.

Example 25A

4-[(Z)-2-Cyano-2-(4,4-dimethyl-4,5-dihydro-1,3-oxazol-2-yl)ethenyl]benzonitrile

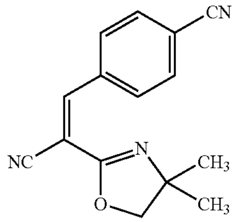

The compound of Example 34A (crude product; 527 mg) and 4-cyanobenzaldehyde (200 mg, 1.5 mmol) are dissolved in ethanol (5 ml). Piperidine (3.5 mg, 0.046 mmol) is added, and the reaction mixture is stirred at room temperature overnight. The crude reaction mixture is concentrated in vacuo, the residue is dissolved in DMSO (5 ml) and purified by preparative HPLC to afford the title compound as a mixture of E and Z geometric isomers.

Yield: 194 mg (51% of th.) HPLC (method 8): $R_t$=3.70 min+4.14 min LC-MS (method 4): $R_t$=3.96 min+4.11 min MS (EI): m/z=252 (M+H)$^+$ $^1$H-NMR (200 MHz, DMSO-$d_6$): δ=1.24 (s, 6H); 4.10 (s, 2H); 7.41 (d, 1H); 7.78 (d, 2H); 7.96 (d, 1H); 8.07 (d, 1H) ppm.

Example 26A

4-[(Z)-2-(1,3-Benzothiazol-2-yl)-2-cyanoethenyl]benzonitrile

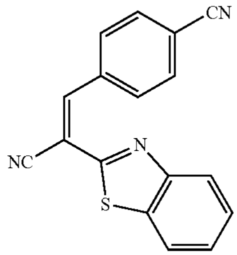

Benzothiazole-2-acetonitrile (750 mg, 4.3 mmol) and 4-cyanobenzaldehyde (564 mg, 4.3 mmol) are dissolved in ethanol (20 ml). Piperidine (11 mg, 0.13 mmol) is added, and the reaction is stirred at room temperature for 2 hours. A precipitate is formed, which is filtered and washed with additional ethanol (5 ml). The solid is dried in a vacuum desiccator overnight and used without further purification.

Yield: 1.12 g (91% of th.) HPLC (method 8): $R_t$=4.94 min MS (EI): m/z=288 (M+H)$^+$ $^1$H-NMR (200 MHz, DMSO-$d_6$): δ=7.47-7.69 (m, 2H); 8.08 (d, 3H); 8.23 (d, 3H); 8.53 (s, 1H) ppm.

Example 27A

Ethyl(2E)-4,4,4-trifluoro-3-{[3-(trifluoromethyl)phenyl]amino}-2-butenoate

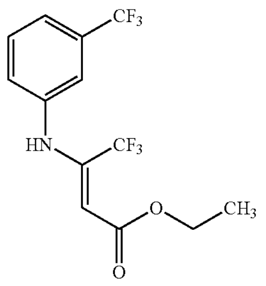

Prepared according to the method of Stanforth et al. [(a) Latham, E. J., Stanforth, S. P., *J. Chem. Soc. Perkin Trans* 1, 1997, 2059; (b) Stanforth, S. P., *Tetrahedron,* 2001, 57, 1833; (c) Latham, E. J., Murphy, S. M., Stanforth, S. P., *Tetrahedron Lett.* 1994, 35, 3395]:

Ethyl(triphenylphosphoranylidene)acetate (677 mg, 1.95 mmol) and 2,2,2-trifluoro-N-[3-(trifluoromethyl)phenyl]acetamide (Example 35A; 500 mg, 1.95 mmol) are dissolved in toluene and stirred at reflux (120° C.) overnight (18 hours). The crude reaction mixture is cooled to room temperature, concentrated, and the residue is chromatographed over silica gel with cyclohexane/ethyl acetate mixtures as eluent to afford a yellow oil which is analytically pure.

Yield: 270 mg (27% of th.) HPLC (method 8): $R_t$=5.38 min MS (EI): m/z=328 $(+H)^+$ $^1$H-NMR (300 MHz, $CDCl_3$): δ=1.32 (t, 3H); 4.22 (q, 2H); 5.43 (s, 1H); 7.36 (d, 1H); 7.41-7.47 (m, 2H); 7.48-7.49 (m, 2H) ppm.

Example 28A

Ethyl(2Z)-2-cyano-3-(4-cyanophenyl)-2-propenoate

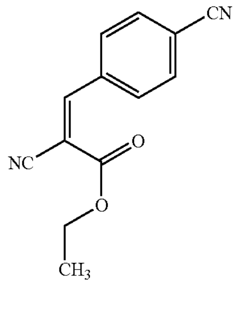

Ethyl cyanoacetate (2.59 g, 22.88 mmol) and 4-formylbenzonitrile (3.0 g, 22.88 mmol) are dissolved in ethanol (100 ml). Piperidine (100 mg, 1.14 mmol) is added, and the reaction mixture is stirred at room temperature for 2 hours. The solvent is removed in vacuo, and the residue is purified by column chromatography on silica with cyclohexane/ethyl acetate mixtures as eluent.

Yield: 5.0 g (97% of th.) HPLC (method 8): $R_t$=4.47 min MS (DCI): m/z=244 $(M+NH_4)^+$ $^1$H-NMR (300 MHz, $CDCl_3$): δ=1.41 (t, 3H); 4.41 (q, 2H); 7.79 (d, 2H); 8.05 (d, 2H); 8.24 (s, 1H) ppm.

Example 29A

Ethyl(2E)-4,4,4-trifluoro-3-{[5-(trifluoromethyl)-3-pyridinyl]amino}-2-butenoate

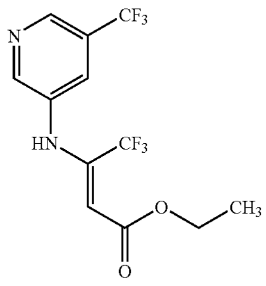

The compound of Example 37A (425 mg, 1.65 mmol) and ethyl(triphenylphosphoranylidene)acetate (573.6 mg, 1.65 mmol) are dissolved in toluene (8.5 ml) under an argon atmosphere. The reaction mixture is refluxed overnight. After cooling to room temperature, the solvent is removed in vacuo, and the residue is purified by column chromatography on silica with cyclohexane/ethyl acetate 7:1→5:1 mixtures as eluent.

Yield: 257 mg (48% of th.) HPLC (method 8): $R_t$=4.83 min MS (DCI): m/z 346 $(M+NH_4)^+$ $^1$H-NMR (200 MHz, DMSO-$d_6$): δ=1.04 (t, 3H); 3.93 (q, 2H); 5.77 (s, 1H); 7.61 (s, 1H); 8.49-8.62 (m, 2H); 9.49 (s, 1H) ppm.

Example 30A

6-Methylnicotinonitrile-1-oxide

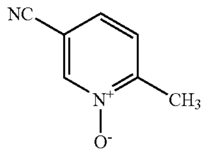

Prepared according to the procedure of Ashimore et al. [Ashimore, A., Ono, T., Uchida, T., Fkaya, C., Watanabe, M., Yokoyama, K, *Chem. Pharm. Bull.* 1990, 38, 2446]:

6-Methylnicotinonitrile (3.68 g, 31.15 mmol) is dissolved in chloroform (60 ml). 3-Chloroperoxybenzoic acid (7.53 g, 32.71 mmol) is added dropwise as a solution in chloroform (60 ml), and the solution is stirred at room temperature overnight. Sodium sulphite (2.92 g, 23.17 mmol) is added, and the resulting mixture is stirred for one hour. The reaction is quenched with saturated sodium bicarbonate solution, and the product is extracted with chloroform (500 ml). The organic phase is washed with brine, dried over magnesium sulphate monohydrate, filtered and concentrated in vacuo. The residue is used without further purification.

Yield: 3.2 g (77% of th.) $^1$H-NMR (400 MHz, DMSO-$d_6$): δ=2.40 (s, 3H); 7.68 (d, 1H); 7.73 (d, 1H); 8.90 (s, 1H) ppm.

Example 31A (5-Cyano-2-pyridinyl)methylacetate

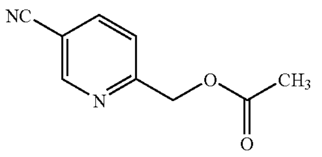

Acetic anhydride (3.2 g, 31.31 mmol) is heated to 115° C. under an argon atmosphere. The compound of Example 30A (700 mg, 5.22 mmol) is added and the solution is stirred at reflux for one hour. Ethanol (3 ml, 51.12 mmol) is added dropwise to the mixture and refluxing is continued for 10 minutes. The mixture is cooled to room temperature, poured into ice water and neutralised with saturated sodium bicarbonate solution. The aqueous phase is extracted with diethyl ether. The organic phase is washed with brine, dried with magnesium sulphate, filtered and concentrated in vacuo to afford a black oil. The oil is dissolved in dimethylsulfoxide (8 ml) and purified by preparative HPLC.

Yield: 233 mg (25% of th.) HPLC (method 8): $R_t$=3.15 min MS (EI): m/z=177 $(M+H)^+$ $^1$H-NMR (300 MHz, DMSO-$d_6$): δ=2.14 (s, 3H); 5.23 (s, 2H); 7.62 (d, 1H); 8.33 (dd, 1H); 8.99 (d, 1H) ppm.

Example 32A 6-(Hydroxymethyl)nicotinonitrile

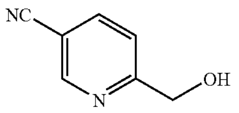

The compound of Example 31A (180 mg, 1.02 mmol) is dissolved in tetrahydrofuran (8 ml). Lithium hydroxide (48.94 mg, 2.04 mmol) is dissolved in water (5 ml) and added to the THF solution. The reaction is stirred for 2 hours at room temperature. The mixture is diluted with water and ethyl acetate. The aqueous phase is extracted three times with ethyl acetate. The organic phases are combined and washed with brine, dried with magnesium sulphate monohydrate, filtered and concentrated in vacuo. The residue is used without further purification.

Yield: 125 mg (91% of th.) HPLC (method 8): $R_t$=1.17 min MS (DCI): m/z=152 $(M+NH_4)^+$ $^1$H-NMR (300 MHz, DMSO-$d_6$): δ=4.63 (d, 2H); 5.64 (t, 1H); 7.65 (d, 1H); 8.29 (dd, 1H); 8.92 (d, 1H) ppm.

Example 33A

6-Formylnicotinonitrile

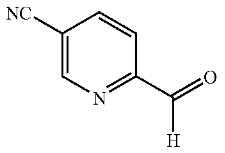

Oxalyl chloride (936 mg, 7.38 mmol) is dissolved in dichlormethane (8 ml) under an argon atmosphere and cooled to −78° C. in an acetone dry-ice bath. Dimethylsulfoxide (1.153 g, 14.76 mmol) is added dropwise and the mixture is stirred for 20 minutes at −78° C. The compound of Example 32A (900 mg, 6.71 mmol) is added dropwise as a dichloromethane (7 ml) solution. The reaction is stirred for an additional two hours at −78° C. Triethylamine (3.05 g, 30.19 mmol) is added and the reaction is kept at −78° C. for 10 minutes, then allowed to warm to room temperature. The reaction is quenched with saturated ammonium chloride solution and extracted with ethyl acetate. The ethyl acetate phase is washed with bicarbonate and brine, dried over magnesium sulphate monohydrate, filtered and concentrated to afford a yellow oil. The crude oil is purified by column chromatography on silica gel with dichloromethane as eluent.

Yield: 424 mg (48% of th.) HPLC (method 8): $R_t$=1.19 min MS (EI): m/z=132 $(M)^+$ $^1$H-NMR (200 MHz, DMSO-$d_6$): δ=5.69 (t, 1H); 7.65 (d, 1H); 8.31 (dd, 1H); 8.93 (d, 1H) ppm.

Example 34A (4,4-Dimethyl-4,5-dihydro-1,3-oxazol-2-yl)acetonitrile

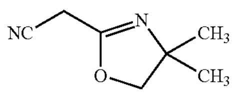

Prepared according to the method of Jnaneshware et al. [(a) Jnaneshware, G. K., Deshpande, V. H., Bedekar, A. V., *J. Chem. Res. Synop.* 1999, 4, 252. (b) Jnaneshware, G. K., Deshpande, V. H., Lalithambika, T., Ravindranathan, T., Bedekar, A. V., *Tetrahedron Lett.* 1998, 39, 459]:

Dicyanomethane (500 mg, 7.6 mmol), 2-amino-2-methylpropanol. (675 mg, 7.6 mmol) and Montmorillonite K-10 (135 mg) are dissolved/suspended in toluene (150 ml). The mixture is heated to reflux and stirred at this temperature overnight (18 hours). The mixture is cooled to room temperature and filtered. The solid is washed with additional toluene and acetone, and the filtrate is concentrated in vacuo to give a dark oil which is used in the next step without further purification.

Yield: 781 mg (75% of th.)

Example 35A 2,2,2-Trifluoro-N-[3-(trifluoromethyl)phenyl]acetamide

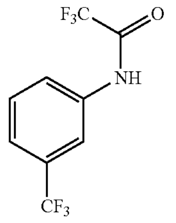

3-(Trifluoromethyl)aniline (4.03 g, 25 mmol) and pyridine (4.35 g, 55 mmol) are dissolved in methylene chloride (250 ml). The solution is cooled to 0° C. and trifluoroacetic anhydride (5.3 g, 25 mmol) is added. The solution is stirred at room temperature overnight. The reaction is quenched with saturated sodium bicarbonate solution, extracted with methylene chloride, washed with saturated aqueous ammonium chloride solution and saturated aqueous copper sulphate solution. The organic phase is dried with magnesium sulphate monohydrate, filtered and concentrated in vacuo. The residue is purified by column chromatography on silica with cyclohexane/ethyl acetate 10:1 mixture as eluent.

Yield: 6.3 g (98% of th.) HPLC (method 8): $R_t$=4.68 min MS (EI): m/z=258 $(M+H)^+$ $^1$H-NMR (300 MHz, DMSO-$d_6$): δ=7.59 (d, 1H); 7.67 (t, 1H); 7.96 (d, 1H); 8.08 (s, 1H); 11.52 (br. s, 1H) ppm.

Example 36A 5-(Trifluoromethyl)-3-pyridinamine

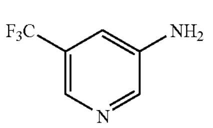

Prepared according to the method of Barlin et al. [Barlin, G. B., Jiravinyu, C., *Aust. J. Chem.,* 1990, 43, 1175]:

3-Chloro-5-(trifluoromethyl)pyridine (3.0 g, 16.52 mmol) is suspended in water (67.5 ml) and treated with copper(I) chloride (8.18 g, 82.62 mmol). Ammonia solution (25%, 67.5 ml) is added and the reaction is stirred for 48 hours at 170° C. in an autoclave. The reaction mixture is cooled to room temperature and extracted three times with dichloromethane. The combined organic phases are washed with brine, dried with magnesium sulphate, filtered and concentrated in vacuo to yield analytically pure product.

Yield: 2.09 g (78% of th.) HPLC (method 8): $R_t$=1.73 min MS (DCI): m/z=180 $(M+NH_4)^+$ $^1$H-NMR (200 MHz, DMSO-$d_6$): δ=5.85 (s, 2H); 7.16 (s, 1H); 8.02 (s, 1H); 8.17 (s, 1H) ppm.

Example 37A 2,2,2-Trifluoro-N-[5-(trifluoromethyl)-3-pyridinyl] acetamide

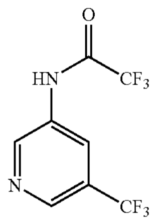

The compound of Example 36A (1 g, 6.2 mmol), trifluoroacetic anhydride (1.30 g, 6.2 mmol) and pyridine (0.54 g, 6.8 mol) are dissolved in tetrahydrofuran (20 ml) under an argon atmosphere. The solution is cooled to −78° C. with stirring and lithium diisopropylamide (3.0 ml of a 2 M solution in THF/heptane, 6.0 mmol) is added dropwise. The reaction mixture is allowed to warm to room temperature, and then stirred at room temperature overnight. The reaction is quenched with water and extracted with ethyl acetate (3×100 ml). The ethyl acetate phase is washed with brine, dried with magnesium sulphate monohydrate, filtered and concentrated to give a yellow oil. The oil is purified by flash chromatography on silica gel with cyclohexane/ethyl acetate mixtures as eluent.

Yield: 1.05 g (66% of th.) HPLC (method 8): $R_t$=4.23 min MS (EI): m/z=259 $(M+H)^+$ $^1$H-NMR (300 MHz, DMSO-$d_6$): δ=8.46 (s, 1H); 8.84 (s, 1H); 9.10 (s, 1H); 11.80 (s, 1H) ppm.

Example 38A 2-(Trimethylsilyl)ethylcyanoacetate

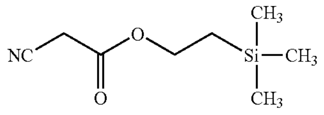

2000 mg (16.91 mmol) 2-(Trimethylsilyl)ethanol are dissolved in 160 ml diethylether. 1307 mg (15.38 mmol) cyanoacetic acid, 3489 mg (16.91 mmol) N,N'-dicyclohexylcarbodiimide and 227 mg (1.54 mmol) 4-(1-pyrrolidinyl) pyridine are added. The mixture is stirred at room temperature for 3 hours under an argon atmosphere and kept at room temperature overnight. The suspension is filtered and the filtrate is washed twice with 5% aqueous acetic acid and twice with water. The organic phase is dried over sodium sulfate, filtered and the solvent is evaporated in vacuo. The residue is re-dissolved in 10 ml hexane and the suspension is filtered over 1 g silica. After evaporation of the solvent, distillation at 0.51 mbar yields the desired product.

Yield: 1.63 g (57% of th) Bp.: 76-78° C./0.51 mbar HPLC (method 9): $R_t$=4.67 min MS (DCI): m/z=203 $(M+NH_4)^+$ $^1$H-NMR (300 MHz, $CDCl_3$): δ=0.04 (s, 9H); 0.99-1.09 (m, 2H); 3.40 (s, 2H); 4.24-4.33 (m, 2H) ppm.

Example 39A 2-(Trimethylsilyl)ethyl 3-oxobutanoate

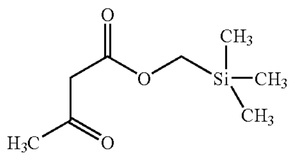

To a mixture of 5.0 g (42.28 mmol) 2-(trimethylsilyl)ethanol and 0.20 g (1.99 mmol) triethylamine are added dropwise 3.55 g (42.28 mmol) 4-methylene-2-oxetanone at 50-60° C. The mixture is stirred at 95° C. for 3 hours and then allowed to stand at ca 5° C. overnight. The reaction mixture is purified by distillation Yield: 8.06 g (94% of th.) Bp.: 80° C./0.46 mbar MS (EI): m/z=220 $(M+NH_4)^+$ $^1$H-NMR (300 MHz, $CDCl_3$): δ=0.00 (s, 9H); 0.92-1.01 (m, 2H); 2.22 (s, 3H); 3.37 (s, 2H); 4.14-4.23 (m, 2H) ppm.

Example 40A 2-(Trimethylsilyl)ethyl 3-{[3-(trifluoromethyl)phenyl]amino}-2-butenoate

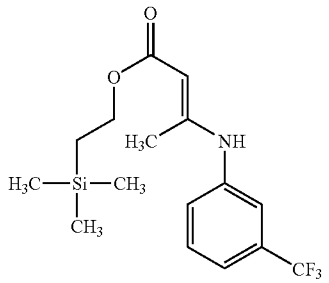

To a solution of 3.75 g (1.5 mmol) of the compound of Example 39A in 55 ml benzene are added 3 g (18.5 mmol) 3-(trifluoromethyl)aniline and 1.1 g (18.5 mmol) acetic acid. The mixture is stirred under reflux overnight using a Dean-Stark trap to remove water. After removal of the solvent in vacuo, the residue is purified by preparative HPLC (column: YMC C18 ODS-AQ 250 mm×30 mm, 11 μm; solvent A: acetonitrile, solvent B: water; gradient: 0 min 10% A, 3 min 10% A, 11 min 90% A, 13 min 90% A, 13.2 min 10% A, 15 min 10% A; wavelength: 220 nm; injection volume: ca. 900 μl ethanol solution; number of injections: 6). The product containing fractions are combined and concentrated in vacuo.

Yield: 1.86 g (29% of th.) MS (EI): m/z=346 $(M+H)^+$ $^1$H-NMR (300 MHz, DMSO-$d_6$): δ=0.00 (s, 9H); 0.87-0.96 (m, 2H); 2.01 (s, 3H); 4.06-4.14 (m, 2H); 4.70 (s, 1H); 7.40-7.48 (m, 3H); 7.49-7.57 (m, 1H); 10.42 (s, 1H) ppm.

Example 41A

Methyl 3-{[3-(trifluoromethyl)phenyl]amino}-2-butenoate

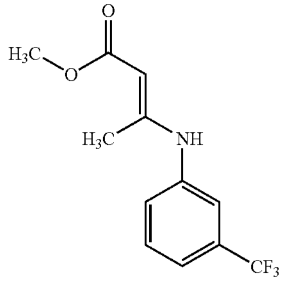

To a solution of 3.48 g (30 mmol) methyl 3-oxobutanoate in 90 ml benzene are added 4.83 g (30 mmol) 3-(trifluoromethyl)aniline and 1.80 g (30 mmol) acetic acid. The mixture is stirred at reflux for four hours using a Dean-Stark trap to remove water. After removal of the solvent in vacuo, the residue is purified by preparative HPLC (column: YMC C18 ODS-AQ 250 mm×30 mm, 11 μm; solvent A: acetonitrile, solvent B: water; gradient: 0 min 10% A, 3 min 10% A, 11 min 90% A, 13 min 90% A, 13.2 min 10% A, 15 min 10% A; wavelength: 220 nm; injection volume: ca. 900 μl ethanol solution; number of injections: 8). The product containing fractions are combined and concentrated in vacuo.

Yield: 2.56 g (33% of th.) MS (EI): m/z=260 $(M+H)^+$ $^1$H-NMR (200 MHz, DMSO-$d_6$): δ=2.06 (s, 3H); 2.35 (s, 3H); 5.10 (s, 1H); 7.49-7.57 (m, 4H); 10.41 (s, 1H) ppm.

Example 42A

Isopropyl 3-{[3-(trifluoromethyl)phenyl]amino}-2-butenoate

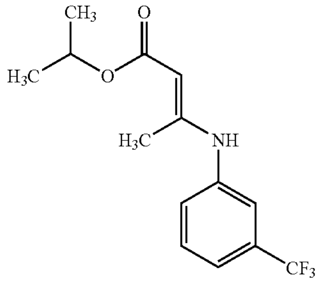

To a solution of 4.33 g (30 mmol) isopropyl 3-oxobutanoate in 90 ml benzene are added 4.83 g (30 mmol) 3-(trifluoromethyl)aniline and 1.80 g (30 mmol) acetic acid. The mixture is stirred under reflux for four hours using a Dean-Stark trap to remove water. After removal of the solvent in vacuo, the residue is purified by preparative HPLC (column: YMC C18 ODS-AQ 250 mm×30 mm, 11 μm; solvent A: acetonitrile, solvent B: water; gradient: 0 min 10% A, 3 min 10% A, 11 min 90% A, 13 min 90% A, 13.2 min 10% A, 15 min 10% A; wavelength: 220 nm; injection volume: ca. 900 μl ethanol solution; number of injections: 8). The product containing fractions are combined and concentrated in vacuo.

Yield: 2.83 g (33% of th.) MS (EI): m/z=288 $(M+H)^+$ $^1$H-NMR (200 MHz, DMSO-$d_6$): δ=1.19 (s, 6H); 2.05 (s, 3H); 4.74 (s, 1H); 4.85-5.02 (m, 1H); 7.47-7.56 (m, 4H); 10.46 (s, 1H) ppm.

Example 43A

2-Methoxyethyl 3-{[3-(trifluoromethyl)phenyl]amino}-2-butenoate

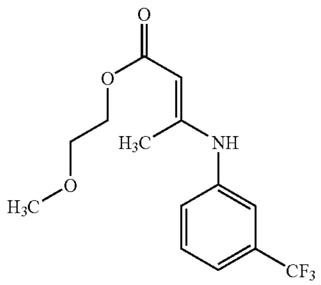

To a solution of 4.81 g (30 mmol) 2-methoxyethyl-3-oxobutanoate in 90 ml benzene are added 4.83 g (30 mmol) 3-(trifluoromethyl)aniline and 1.80 g (30 mmol) acetic acid. The mixture is stirred under reflux for four hours using a Dean-Stark trap to remove water. After removal of the solvent in vacuo, the residue is purified by preparative HPLC (column: YMC C18 ODS-AQ 250 mm×30 mm, 11 μm; solvent A: acetonitrile, solvent B: water; gradient: 0 min 10% A, 3 min 10% A, 11 min 90% A, 13 min 90% A, 13.2 min 10% A, 15 min 10% A; wavelength: 220 nm; injection volume: ca. 900 μl ethanol solution; number of injections: 9). The product containing fractions are combined and concentrated in vacuo.

Yield: 2.68 g (29% of th.) MS (EI): m/z=304 $(M+H)^+$ 1H-NMR (200 MHz, DMSO-$d_6$): δ=2.06 (s, 3H); 3.27 (s, 3H); 3.53 (t, 2H); 4.15 (t, 2H); 4.80 (s, 1H); 7.50-7.56 (m, 4H); 10.39 (s, 1H) ppm.

Preparation Examples

Example 1

Diethyl 2-amino-4-(4-cyanophenyl)-6-methyl-1-(3-methylphenyl)-1,4-dihydro-3,5-pyridine-dicarboxylate

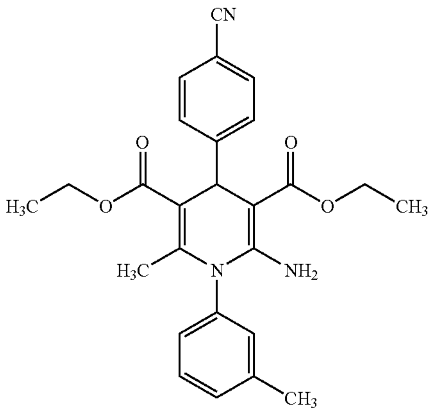

Under argon, 100 mg (0.46 mmol) ethyl(2E)-3-[(3-methylphenyl)amino]-2-butenoate (preparation analogously to Example 1A), 59.80 mg (0.46 mmol) 4-formylbenzonitrile and 51.58 mg (0.46 mmol) ethyl cyanoacetate are dissolved in 2 ml ethanol. 77.66 mg (90 μl, 0.91 mmol) piperidine are added to the mixture which is stirred at reflux overnight. After the reaction is finished, the mixture is purified by preparative HPLC followed by column chromatography on silica with dichloromethane as eluent.

Yield: 16 mg (8% of th.) LC-MS (method 2): $R_t$=3.05 min MS (EI): m/z=446 $(M+H)^+$ $^1$H-NMR (200 MHz, DMSO-$d_6$): δ=1.05-1.16 (m, 6H); 1.95 (s, 3H); 2.39 (s, 3H); 3.89-4.10 (m, 4H); 4.95 (s, 1H); 6.72 (br. s, 2H); 7.15-7.27 (m, 2H); 7.32-7.40 (m, 1H); 7.46 (d, 3H); 7.76 (d, 2H) ppm.

Example 2

Diethyl 2-amino-4-(4-cyanophenyl)-6-methyl-1-[3-(trifluoromethyl)phenyl]-1,4-dihydro-3,5-pyridine-dicarboxylate

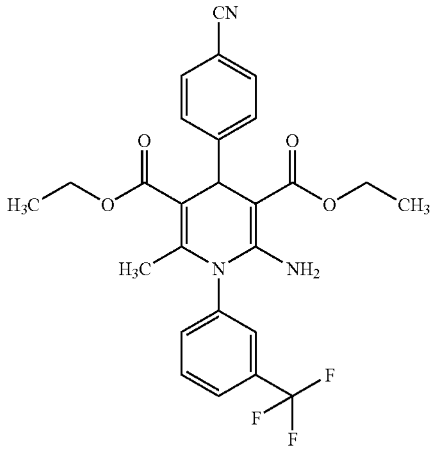

Method a):

The compound is prepared as described in Example 1 from 100 mg (0.37 mmol) of the compound of Example 1A, 48 mg (0.37 mmol) 4-formylbenzonitrile, 41.40 mg (0.37 mmol) ethyl cyanoacetate and 62.32 mg (72 μl, 0.73 mmol) piperidine in 2 ml ethanol. The mixture is purified by preparative HPLC.

Yield: 72 mg (39% of th.) HPLC (method 8): $R_t$=4.63 mm MS (EI): m/z=500 $(M+H)^+$ $^1$H-NMR (200 MHz, DMSO-$d_6$): δ=1.04-1.16 (m, 6H); 1.92 (s, 3H); 3.89-4.09 (m, 4H); 4.96 (s, 1H); 6.85 (br. s, 2H); 7.49 (d, 2H); 7.74 (d, 3H); 7.83 (d, 2H), 7.93 (d, 1H) ppm.

Method b):

Ethyl cyanoacetate (2.07 g, 18.3 mmol) and 4-cyanobenzaldehyde (2.40 g, 18.3 mmol) are dissolved in ethanol (125 ml) under an argon atmosphere. Piperidine (46.7 mg, 0.55 mmol) is added and the reaction mixture is stirred at room temperature for 2 hours. An ethanol (300 ml) solution of the compound of Example 1A (5.00 g, 18.3 mmol) and additional piperidine (0.156 g, 1.83 mmol) is added, and the reaction mixture is stirred at reflux for an additional 16 hours. The crude reaction product is concentrated in vacuo and chromatographed over silica gel with cyclohexane/ethyl acetate mixtures to give a pale yellow oil.

Yield: 4.6 g (43% of th.)

The following compound is prepared analogously as described for Example 1:

| Ex.-No. | Structure | Analytical data |
|---|---|---|
| 3 | 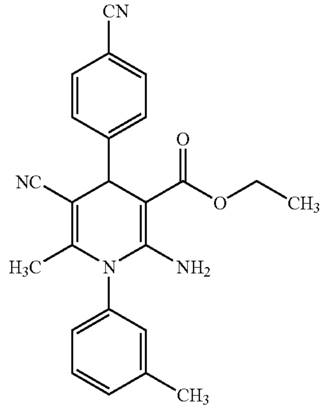 | LC-MS (method 7): $R_t$ = 3.83 min MS (EI): m/z = 399 $(M + H)^+$ |

Example 4

2-Amino-5-cyano-4-(4-cyanophenyl)-6-methyl-1-[3-(trifluoromethyl)phenyl]-1,4-dihydro-3-pyridinecarboxamide

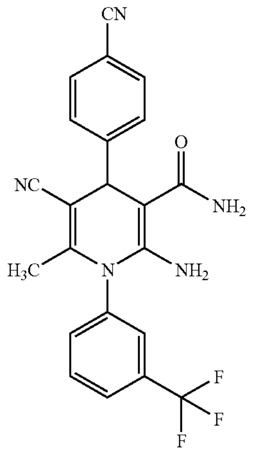

Under argon, 100 mg (0.44 mmol) of the compound of Example 2A, 57.97 mg (0.44 mmol) 4-formylbenzonitrile and 37.17 mg (0.44 mmol) 2-cyanoacetamide are dissolved in 2 ml ethanol. 3.76 mg (4.4 μl, 0.04 mmol) piperidine are added and the mixture is stirred at reflux overnight. The product is crystallised from the reaction mixture at 4° C. The formed crystals are filtered, washed twice with ethanol and dried. The crude product is purified by column chromatography with dichloromethane/methanol 100:1 as eluent.

Yield: 63 mg (34% of th.) LC-MS (method 6): $R_t$=4.21 min MS (EI): m/z=424 $(M+H)^+$HPLC (method 8): $R_t$=3.99 ml $^1$H-NMR (200 MHz, DMSO-$d_6$): δ=1.68 (s, 3H); 4.76 (s, 1H); 6.42 (br. s, 2H); 7.24 (br. s, 2H); 7.63 (d, 2H); 7.77 (d, 2H); 7.82-7.95 (m, 4H) ppm.

Example 5

Ethyl 6-amino-5-(aminocarbonyl)-4-(4-cyanophenyl)-2-methyl-1-[3-(trifluoromethyl)phenyl]-1,4-dihydro-3-pyridinecarboxylate

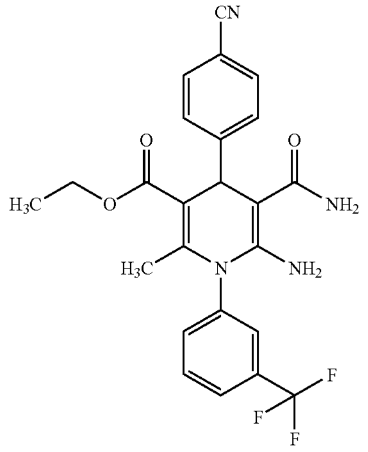

Under argon, 100 mg (0.37 mmol) of the compound of Example 1A, 48.00 mg (0.37 mmol) 4-formylbenzonitrile and 30.77 mg (0.37 mmol) 2-cyanoacetamide are dissolved in 2 ml ethanol. 1.56 mg (1.81 μl, 0.02 mmol) piperidine are added to the mixture which is stirred at reflux. After one hour, additional 9.35 mg (10.86 μl, 0.11 mmol) piperidine are added, and the reaction mixture is stirred at reflux overnight. After the reaction is finished, the mixture is purified by column chromatography with dichloromethane and dichloromethane/methanol 100:1→80:1 as eluent.

Yield: 40 mg (23% of th.) HPLC (method 8): $R_t$=4.18 min MS (EI): m/z=471 $(M+H)^+$ $^1$H-NMR (300 MHz, DMSO-$d_6$): δ=1.19 (t, 3H); 1.87 (s, 3H); 4.06 (q, 2H); 4.90 (s, 1H); 6.45 (br. s, 2H); 7.03 (br. s, 2H); 7.61 (d, 2H); 7.68 (d, 2H); 7.72-7.79 (m, 3H); 7.89 (d, 1H) ppm.

Example 6

Ethyl 2-amino-5-cyano-4-(4-cyanophenyl)-6-methyl-1-[3-(trifluoromethyl)phenyl]-1,4-dihydro-3-pyridinecarboxylate

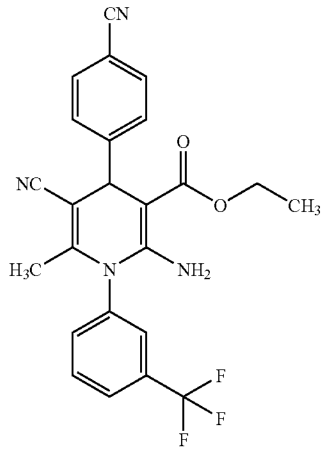

Under argon, 100 mg (0.44 mmol) of the compound of Example 2A, 57.97 mg (0.44 mmol) 4-formylbenzonitrile and 50.01 mg (0.44 mmol) ethyl cyanoacetate are dissolved in 2 ml ethanol. 3.76 mg (4.4 μl, 0.04 mmol) piperidine are added, and the mixture is stirred at reflux overnight. After cooling down to room temperature, the formed crystals are filtered and washed twice with ethanol. The crude product is purified by column chromatography with cyclohexane/ethyl acetate mixtures as eluent.

Yield: 63 mg (32% of th.) PLC (method 8): $R_t$=4.89 min MS (EI): m/z=453 $(M+H)^+$ $^1$H-NMR (300 MHz, DMSO-$d_6$): δ=0.97 (t, 3H); 1.72 (s, 3H); 3.88 (q, 2H); 4.59 (s, 1H); 7.04 (br. s, 2H); 7.56 (d, 2H); 7.76-7.86 (m, 4H); 7.91-7.96 (m, 1H); 7.98 (s, 1H) ppm.

Example 7

5-Cyano-4-(4-cyanophenyl)-2-imino-N,N,6-trimethyl-1-[3-(trifluoromethyl)phenyl]-1,2,3,4-tetrahydro-3-pyridinecarboxamide

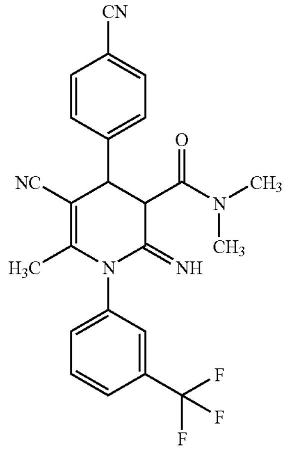

Under argon, 100 mg (0.44 mmol) of the compound of Example 2A, 57.97 mg (0.44 mmol) 4-formylbenzonitrile and 49.57 mg (0.44 mmol) 2-cyano-N,N-dimethylacetamide are dissolved in 2 ml ethanol. 3.76 mg (4.4 μl, 0.04 mmol) piperidine are added, and the mixture is stirred at reflux overnight. After cooling down to room temperature, the crude product is purified by column chromatography with cyclohexane/ethyl acetate 20:1, 10:1, 8:1, 6:1, 4:1, 2:1, 1:1, 1:2 and dichloromethane/methanol 100:1, 50:1, 20:1 as eluents. The product containing fractions are repurified by preparative HPLC.

Yield: 70 mg (35% of th.) LC-MS (method 3): R=2.49 min MS (EI): m/z=452 $(M+H)^+$ $^1$H-NMR (300 MHz, DMSO-$d_6$): δ=1.90 (s, 3H); 2.89 (s, 3H); 3.14 (s, 3H); 4.12-4.17 (m, 1H); 4.28-4.33 (m, 1H); 7.60 (d, 2H); 7.66-7.85 (m, 4H); 7.89 (d, 2H); 8.52 (s, 1H) ppm.

The following compounds are prepared analogously as described for Example 4:

| Ex.-No. | Starting material | Structure | Analytical data |
|---|---|---|---|
| 8 | Example 2A | 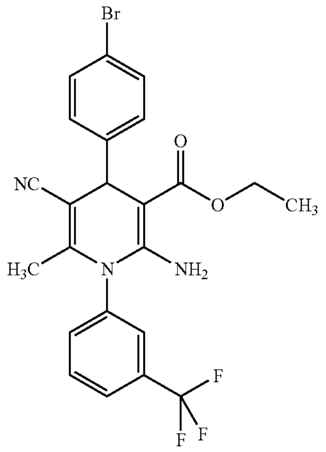 | HPLC (method 8): $R_t$ = 5.31 min. MS (EI): m/z = 506 $(M + H)^+$ |

-continued

| Ex.-No. | Starting material | Structure | Analytical data |
|---|---|---|---|
| 9 | Example 3A | 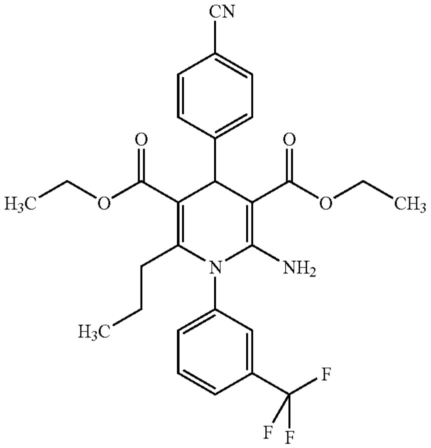 | LC-MS (method 3): $R_t$ = 3.68 min. MS (EI): m/z = 528 $(M + H)^+$ |
| 10 | Example 7A | 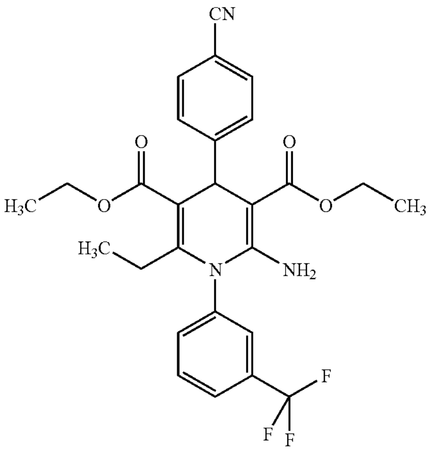 | LC-MS (method 7): $R_t$ = 4.43 min HPLC (method 8): $R_t$ = 4.67 min MS (EI): m/z = 514 $(M + H)^+$ |

Example 11

Ethyl 4-(4-cyanophenyl)-5-[(dimethylamino)carbonyl]-6-imino-2-methyl-1-[3-(trifluoromethyl)phenyl]-1,4,5,6-tetrahydro-3-pyridinecarboxylate

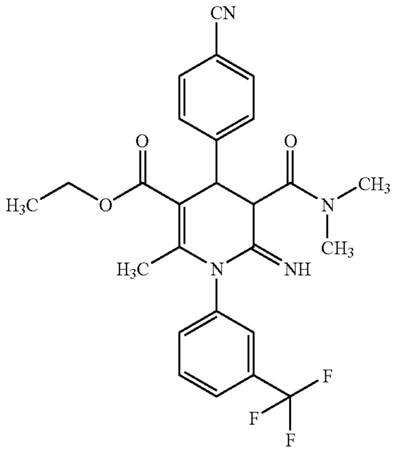

Under argon, 200 mg (0.73 mmol) of the compound of Example 1A, 95.98 mg (0.73 mmol) 4-formylbenzonitrile and 82.07 mg (0.73 mmol) 2-cyano-N,N-dimethylacetamide are dissolved in 4 ml ethanol. 6.23 mg (7.24 μl, 0.07 mmol) piperidine are added, and the mixture is stirred at reflux overnight. After cooling down to room temperature, the crude product is purified by column chromatography on silica with cyclohexane/ethyl acetate 2:1 and dichloromethane/methanol 100:1, 40:1 as eluents.

Yield: 29 mg (8% of th) LC-MS (method 4): $R_t$=3.31 min. MS (EI): m/z=498 $(M)^+$ $^1$H-NMR (400 MHz, DMSO-$d_6$): δ=1.04 (t, 3H); 2.08 (s, 3H); 2.89 (s, 3H); 3.21 (s, 3H); 3.97 (q, 2H); 4.20 (s, 1H); 4.35 (s, 1H); 7.54 (d, 2H); 7.59-7.65 (m, 2H); 7.67-7.76 (m, 2H); 7.83 (d, 2H); 8.27 (s, 1H) ppm.

Example 12

5-Acetyl-6-amino-4-(4-cyanophenyl)-2-methyl-1-[3-(trifluoromethyl)phenyl]-1,4-dihydro-3-pyridinecarbonitrile

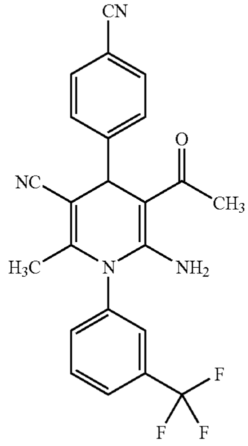

Under argon, 100 mg (1.20 mmol) 5-methylisoxazole are dissolved in 2 ml ethanol and 81.90 mg (1.20 mmol) sodium ethanolate are added. The mixture is stirred at room temperature for one hour. Then 272.24 mg (1.20 mmol) of the compound of Example 2A, 157.82 mg (1.20 mmol) 4-formylbenzonitrile and 10.25 mg (11.90 μl, 0.12 mmol) piperidine are added to the mixture which is stirred at reflux overnight. After the reaction is finished, the mixture is purified by preparative HPLC.

Yield: 44 mg (9% of th.) LC-MS (method 6): $R_t$=4.40 min. MS (EI): m/z=423 $(M+H)^+$ $^1$H-NMR (300 MHz, DMSO-$d_6$): δ=1.68 (s, 3H); 1.80 (s, 3H); 4.80 (s, 1H); 7.60 (d, 2H); 7.81 (d, 2H); 7.87 (d, 2H); 7.94 (d, 2H) ppm.

The following compounds are prepared analogously as described for Example 4:

| Ex-No. | Starting material | Structure | Analytical data |
|---|---|---|---|
| 13 | Example 8A | 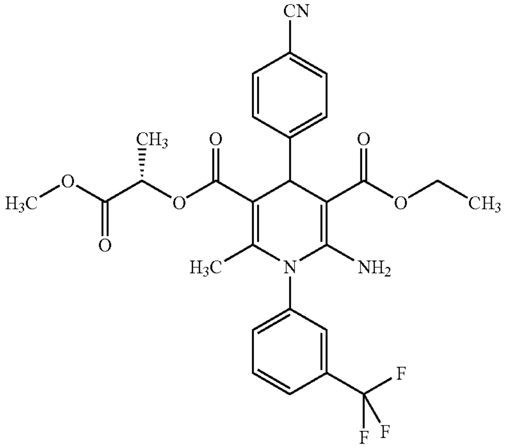 | mixture of diastereotners LC-MS (method 7): $R_t$ = 4.13 min. MS (EI): m/z = 558 $(M + H)^+$ |
| 14 | Example 9A | 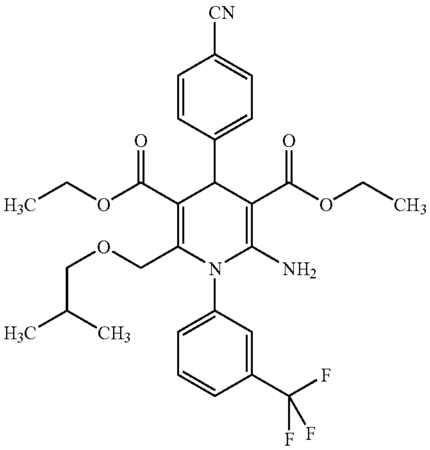 | LC-MS (method 7): $R_t$ = 4.56 min. HPLC (method 8): $R_t$ = 5.05 min. MS (EI): m/z = 572 $(M + H)^+$ |

-continued
| Ex-No. | Starting material | Structure | Analytical data |
|---|---|---|---|
| 15 | Example 10A | 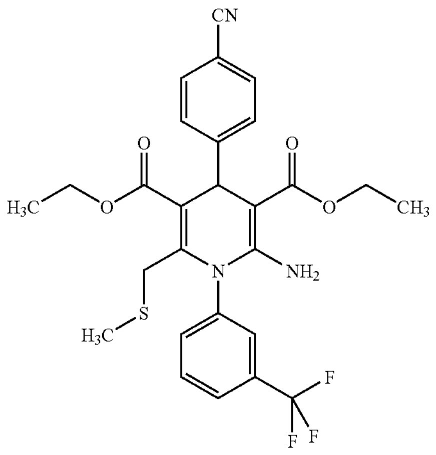 | LC-MS (method 7): $R_t$ = 4.20 min HPLC (method 8): $R_t$ = 4.75 min MS (EI): m/z = 546 $(M + H)^+$ |
| 16 | Example 11A | 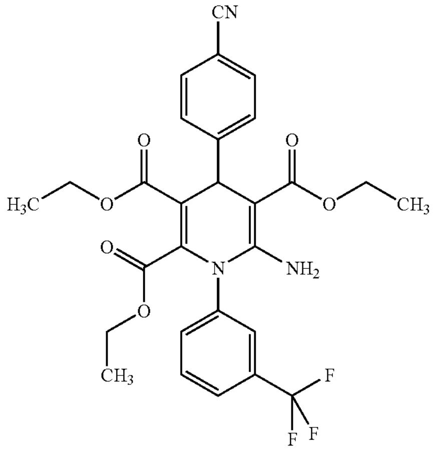 | LC-MS (method 7): $R_t$ = 4.03 min HPLC (method 8): $R_t$ = 5.23 min MS (EI): m/z = 558 $(M + H)^+$ |
| 17 | Example 8A | 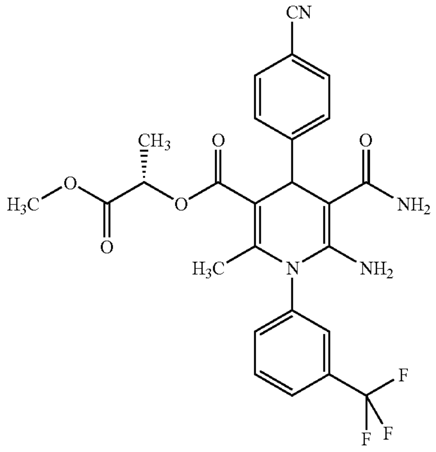 | mixture of diastereomers LC-MS (method 7): $R_t$ = 2.18 + 3.18 min MS (EI): m/z = 529 $(M + H)^+$ |

-continued

| Ex-No. | Starting material | Structure | Analytical data |
|---|---|---|---|
| 18 | Example 12A | 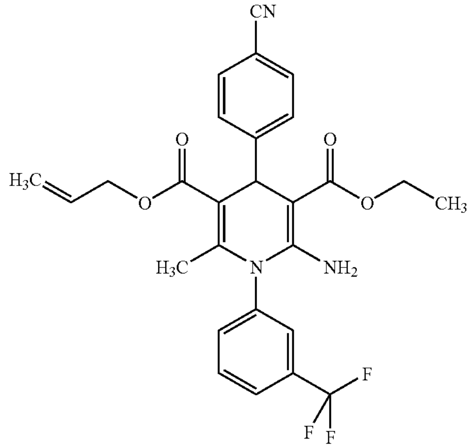 | LC-MS (method 7): $R_t$ = 4.12 min MS (EI): m/z = 512 $(M + H)^+$ |

Example 19 and Example 20

3-Ethyl 5-[(1S)-2-methoxy-1-methyl-2-oxoethyl]2-amino-4-(4-cyanophenyl)-6-methyl-1-[3-(trifluoromethyl)phenyl]-1,4-dihydro-3,5-pyridinedicarboxylate

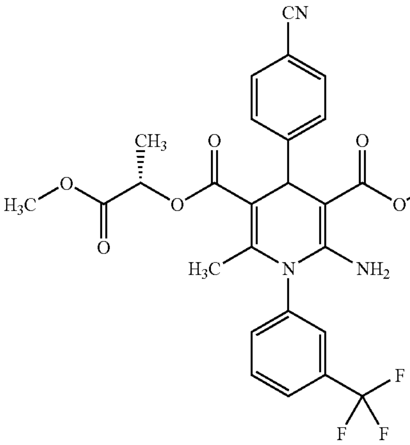

The two diastereomers of Example 13 are separated by preparative HPLC.

Example 19—Diastereomer 1

$^1$H-NMR (200 MHz, DMSO-$d_6$): δ=1.1 (t, 3H); 1.3 (d, 3H); 2.0 (s, 3H); 3.6 (s, 3H); 4.0 (m, 2H); 4.9 (q, 1H); 5.0 (s, 1H); 6.9 (br. s, 2H); 7.5 (m, 2H); 7.8 (m, 3H); 7.9 (m, 3H) ppm.

Example 20—Diastereomer 2

$^1$H-NMR (200 MHz, DMSO-$d_6$): δ=1.1 (t, 3H); 1.4 (d, 3H); 1.9 (s, 3H); 3.5 (s, 3H); 4.0 (m, 2H); 5.0 (m, 1H); 5.0 (s, 1H); 6.9 (br. s, 2H); 7.5 (m, 2H); 7.8 (m, 3H); 7.9 (m, 3H) ppm.

Example 21

3-Ethyl 5-[(1R)-2-methoxy-1-methyl-2-oxoethyl]2-amino-4-(4-cyanophenyl)-6-methyl-1-[3-(trifluoromethyl)phenyl]-1,4-dihydro-3,5-pyridinedicarboxylate

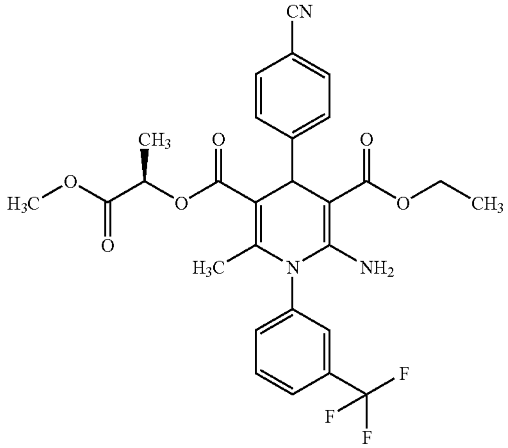

Under argon, 100 mg (0.30 mmol) of the compound of Example 13A and 39.58 mg (0.30 mmol) 4-formylbenzonitrile are dissolved in 2 ml ethanol. To this mixture, 34.14 mg (0.30 mmol) ethyl cyanoacetate and 2.57 mg (2.99 μl, 0.03 mmol) piperidine are added. The reaction mixture is stirred for 30 min at room temperature and at reflux overnight. After cooling down to room temperature, the formed crystals are filtered. The crude product is purified by column chromatography on silica with dichloromethane and dichloromethane/methanol 100:1, 40:1 as eluent.

Yield: 55 mg (34% of th.) as mixture of diastereomers HPLC (method 8): $R_t$=4.63 min MS (EI): m/z=558 $(M+H)^+$ $^1$H-NMR (300 MHz, DMSO-$d_6$): δ=1.10 (t, 6H); 1.3 (d, 3H); 1.4 (d, 3H); 1.91 (s, 3H); 1.96 (s, 3H); 3.54 (s, 3H); 3.63 (s, 3H); 3.92-4.05 (m, 4H); 4.85-4.96 (m, 2H); 4.98 (s, 2H); 6.83 (br.s, 4H); 7.51 (m, 4H); 7.73 (m, 6H); 7.77-7.93 (m, 6H) ppm.

Example 22 and Example 23

3-Ethyl 5-[(1R)-2-methoxy-1-methyl-2-oxoethyl]2-amino-4-(4-cyanophenyl)-6-methyl-1-[3-(trifluoromethyl)phenyl]-1,4-dihydro-3,5-pyridinedicarboxylate

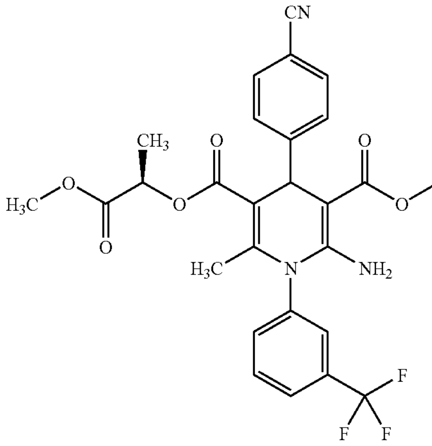

The two diastereomers of Example 21 are separated by preparative HPLC.

Example 22—Diastereomer 1

$^1$H-NMR (400 MHz, DMSO-$d_6$): δ=1.1 (t, 3H); 1.4 (d, 3H); 1.9 (s, 3H); 3.6 (s, 3H); 4.0 (m, 2H); 5.0 (m, 1H); 5.0 (s, 1H); 6.9 (br. s, 2H); 7.5 (m, 2H); 7.7 (m, 3H); 7.8 (m, 2H); 7.9 (m, 1H) ppm.

Example 23—Diastereomer 2

$^1$H-NMR (400 MHz, DMSO-$d_6$): δ=1.1 (t, 3H); 1.3 (d, 3H); 1.9 (s, 3H); 3.7 (s, 3H); 4.0 (m, 2H); 4.9 (q, 1H); 5.0 (s, 1H); 6.9 (br. s, 2H); 7.5 (m, 2H); 7.7 (m, 3H); 7.8 (m, 1H); 7.9 (m, 2H) ppm.

The following compounds are prepared analogously as described for Example 4:

| Ex-No. | Starting material | Structure | Analytical data |
|---|---|---|---|
| 24 | Example 14A | 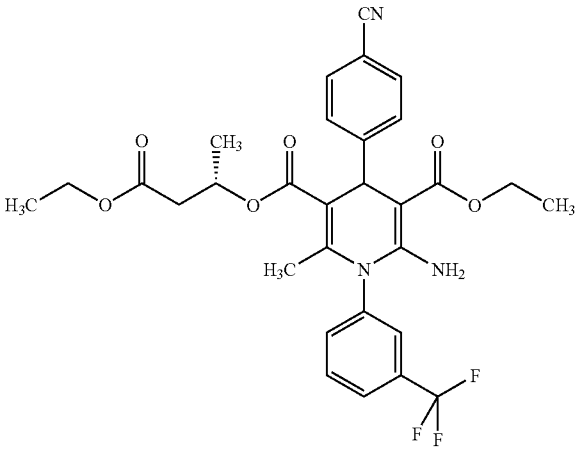 | HPLC (method 8): $R_t$ = 4.74 min. MS (EI): m/z = 586 $(M + H)^+$ |
| 25 | Example 15A | 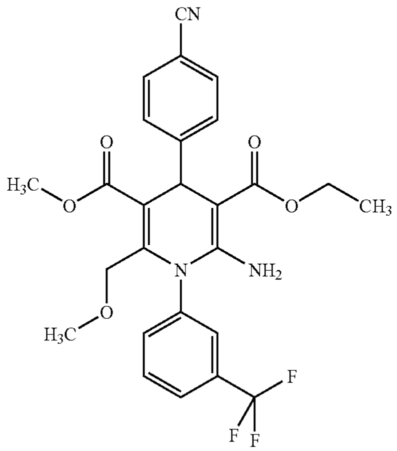 | LC-MS (method 7): $R_t$ = 3.80 min. MS (EI): m/z = 516 $(M + H)^+$ |

-continued
| Ex-No. | Starting material | Structure | Analytical data |
|---|---|---|---|
| 26 | Example 16A | 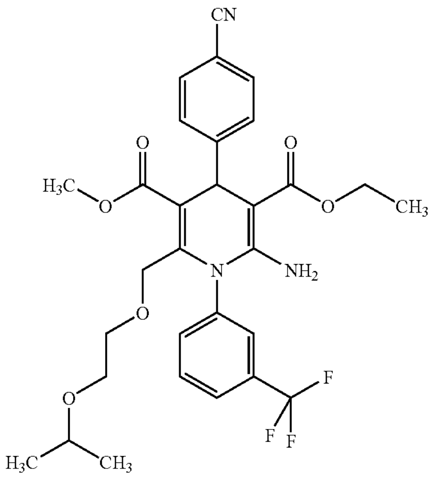 | LC-MS (method 7): $R_t$ = 4.12 min. MS (EI): m/z = 588 $(M + H)^+$ |
| 27 | Example 17A | 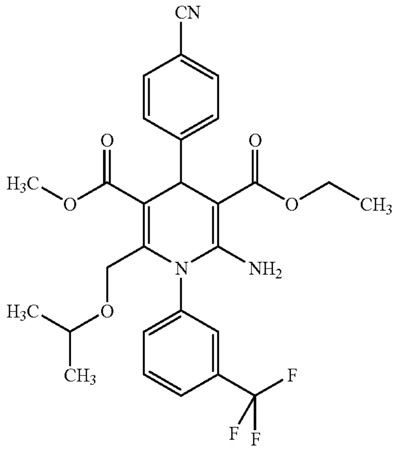 | LC-MS (method 7): $R_t$ = 4.10 min. MS (EI): m/z = 544 $(M + H)^+$ |
| 28 | Example 18A | 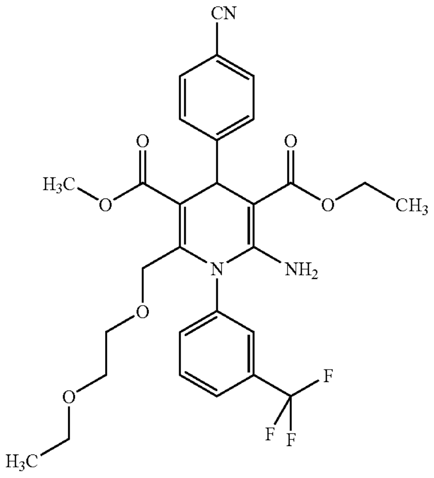 | LC-MS (method 7): $R_t$ = 3.95 min MS (EI): m/z = 574 $(M + H)^+$ |

-continued
| Ex-No. | Starting material | Structure | Analytical data |
|---|---|---|---|
| 29 | Example 19A | 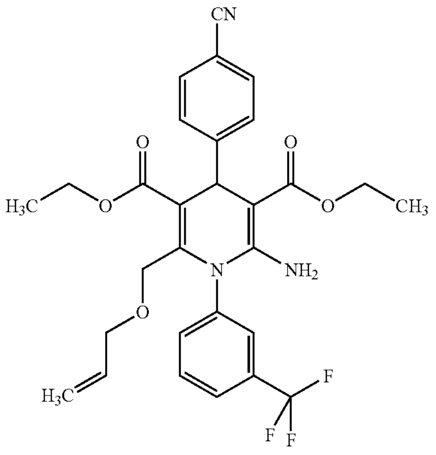 | LC-MS (method 7): $R_t$ = 4.18 min MS (EI): m/z = 556 $(M + H)^+$ |
| 30 | Example 20A | 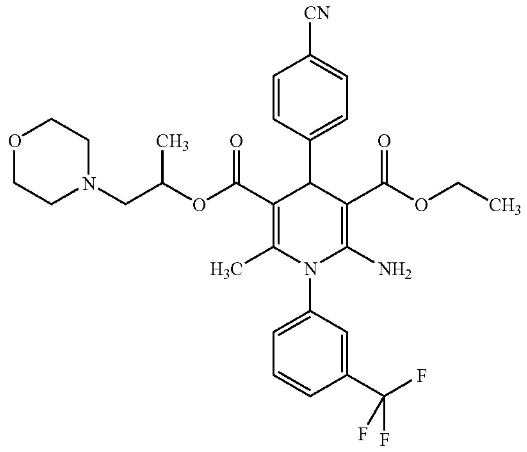 | MS (EI): m/z = 599 $(M + H)^+$ |
| 31 | Example 1A and 21A | 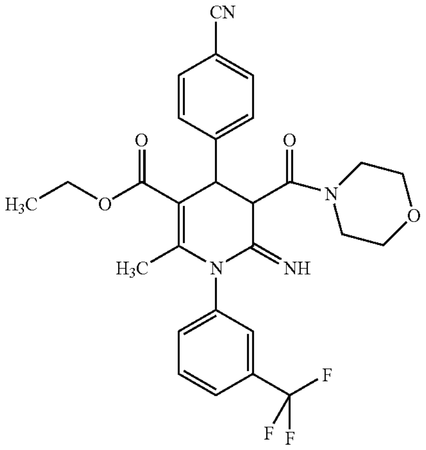 | LC-MS (method 7): $R_t$ = 2.15 min. HPLC (method 8): $R_t$ = 4.43 min. MS (EI): m/z = 541 $(M + H)^+$ |

-continued
| Ex-No. | Starting material | Structure | Analytical data |
| --- | --- | --- | --- |
| 32 | Example 1A and 23A | 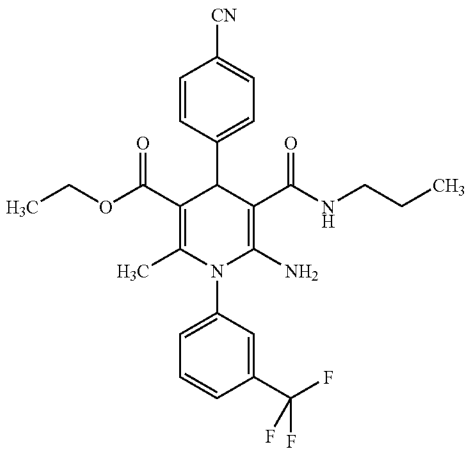 | HPLC (method 8): $R_t$ = 4.57 min. MS (EI): m/z = 513 $(M + H)^+$ |
| 33 | Example 1A and 22A | 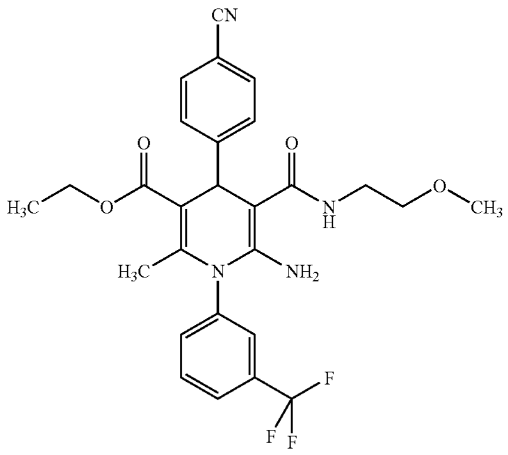 | LC-MS (method 7): $R_t$ = 2.12 + 2.92 min. MS (EI): m/z = 529 $(M + H)^+$ |
| 34 | Example 1A | 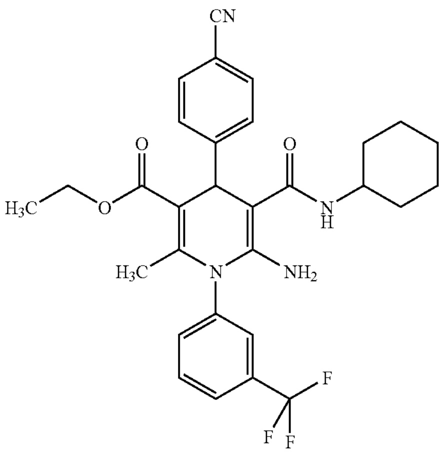 | LC-MS (method 7): $R_t$ = 2.54 + 3.34 min. MS (EI): m/z = 553 $(M + H)^+$ |

-continued
| Ex-No. | Starting material | Structure | Analytical data |
|---|---|---|---|
| 35 | Example 1A | 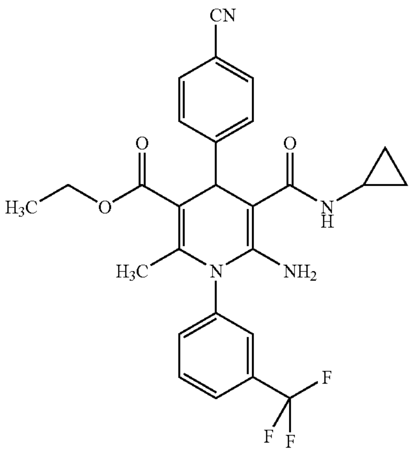 | LC-MS (method 7): $R_t$ = 2.17 + 2.98 min. MS (EI): m/z = 511 $(M + H)^+$ |
| 36 | Example 1A | 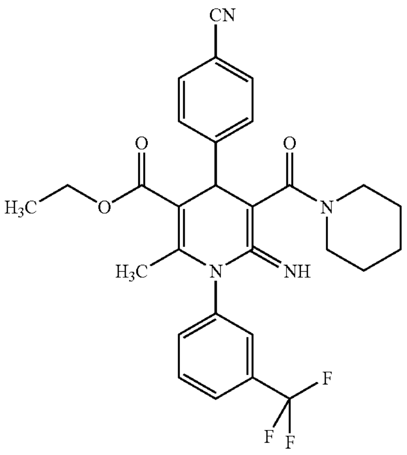 | LC-MS (method 7): $R_t$ = 2.32 min. MS (EI): m/z = 539 $(M + H)^+$ |
| 37 | Example 1A | 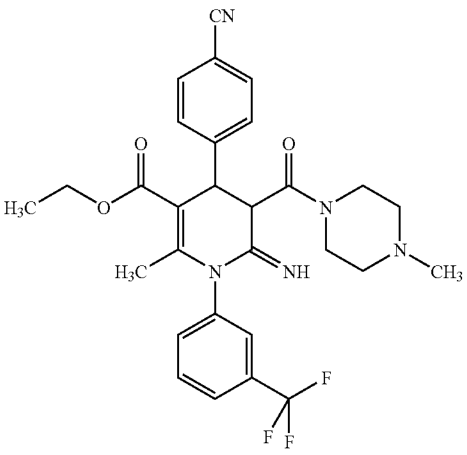 | LC-MS (method 7): $R_t$ = 1.64 + 1.92 min. MS (EI): m/z = 554 $(M + H)^+$ |

-continued
| Ex-No. | Starting material | Structure | Analytical data |
|---|---|---|---|
| 38 | Example 1A | 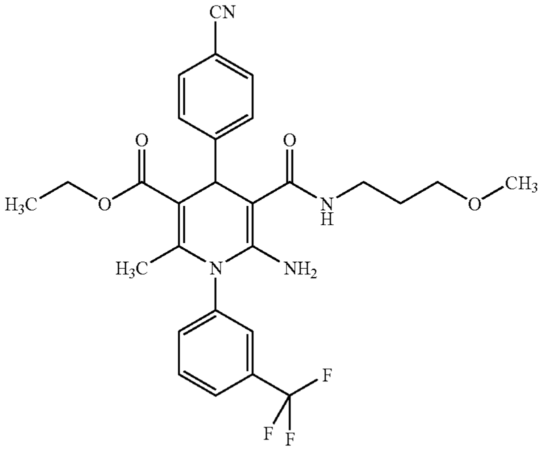 | LC-MS (method 7): $R_t$ = 2.22 + 3.04 min. MS (EI): m/z = 543 $(M + H)^+$ |
| 39 | Example 1A | 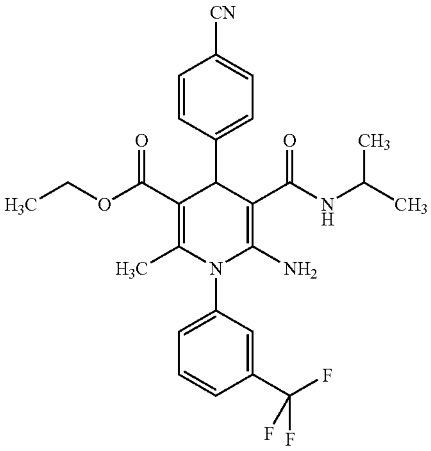 | LC-MS (method 7): $R_t$ = 2.26 + 2.92 min. MS (EI): m/z = 513 $(M + H)^+$ |
| 40 | Example 1A | 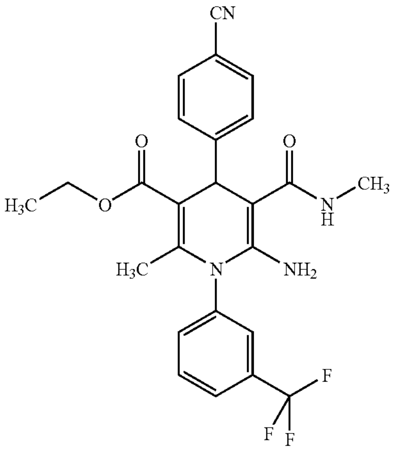 | LC-MS (method 7): $R_t$ = 2.12 + 2.81 min. MS (EI): m/z = 485 $(M + H)^+$ |

Example 41

Ethyl 6-amino-5-cyano(4-(cyanophenyl)-2-methyl-1-[3-(trifluoromethyl)phenyl]-1,4-dihydro-3-pyrdinecarboxylate

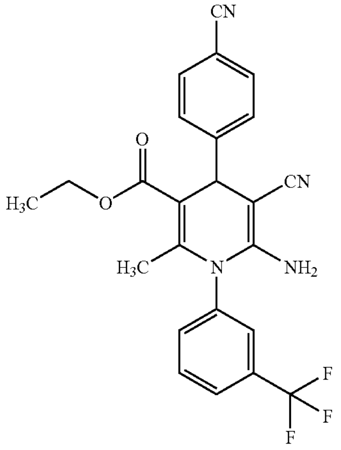

The compound is prepared as described for Example 4 from 100 mg (0.37 mmol) of the compound of Example 1A, 48 mg (0.37 mmol) 4-formylbenzonitrile, 24.18 mg (0.37 mmol) malononitrile and 3.12 mg (3.6 µl, 0.04 mmol) piperidine in 21 ml ethanol. The product is purified by HPLC.

Yield: 33 mg (20% of th.) HPLC (method 8): $R_t$=4.91 ml. LC-MS (method 7): $R_t$=3.59 min. MS (EI): m/z=453 $(M+H)^{+1}$ H-NMR (300 MHz, DMSO-$d_6$): δ=1.04 (t, 3H); 1.94 (s, 3H); 3.96 (q, 2H); 4.60 (s, 1H); 5.53 (s, 2H); 7.50 (d, 2H); 7.66 (d, 1H); 7.72-7.91 (m, 5H) ppm.

Example 42

2-Amino-4-(4-cyanophenyl)-6-methyl-1-[3-(trifluoromethyl)phenyl]-1,4-dihydro-3,5-pyridinedicarbonitrile

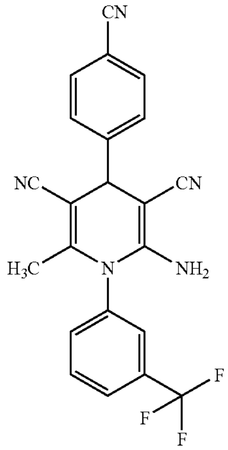

Under argon, 750 mg (3.32 mmol) of the compound of Example 2A, 434.79 mg (3.32 mmol) 4-formylbenzonitrile and 219.04 mg (3.32 mmol) malononitrile are dissolved in 5 ml ethanol. 28.23 mg (33 µl, 0.33 mmol) piperidine are added, and the mixture is stirred at reflux overnight. The product is crystallised from the reaction mixture at 0° C. The formed crystals are filtered, washed twice with cold ethanol and dried.

Yield: 1.17 g (83% of th.) LC-MS (method 7): $R_t$=3.20 min. MS (EI): m/z=406 $(M+H)^+$ $^1$H-NMR (200 MHz, DMSO-$d_6$): δ=1.73 (s, 3H); 4.55 (s, 1H); 5.78 (s, 2H); 7.65 (d, 2H); 7.76 (d, 2H); 7.91 (d, 4H) ppm.

The following compound is prepared analogously as described for Example 2:

| Ex-No. | Starting material | Structure | Analytical data |
| --- | --- | --- | --- |
| 43 | Example 1A | 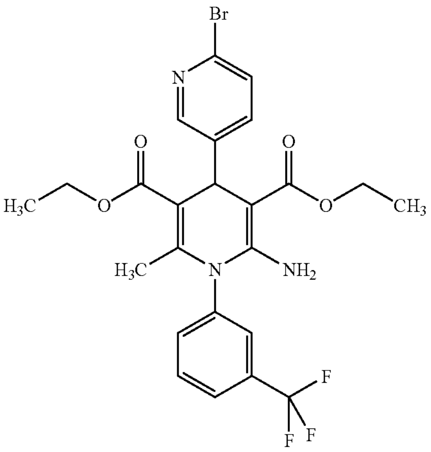 | LC-MS (method 6): $R_t$ = 3.92 min. HPLC (method 8): $R_t$ = 5.34 min. MS (EI): m/z = 555 $(M + H)^+$ |

Example 44

Diethyl 4-(4-cyanophenyl)-2-{[(ethylamino)carbonyl]amino}-6-methyl-1-[3-(trifluoromethyl)phenyl]-1,4-dihydro-3,5-pyridinedicarboxylate

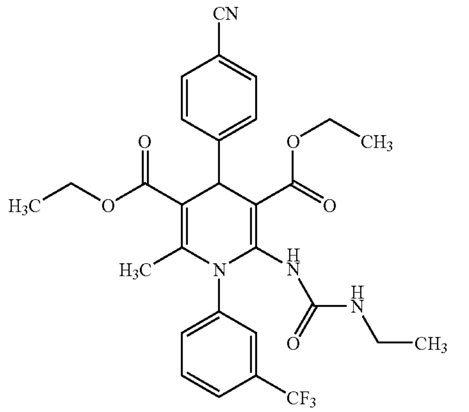

To a stirred solution of the compound of Example 2 (100 mg, 0.20 mmol) in acetonitrile (5 ml) is added 1-isocyanatoethane (14.23 mg, 0.20 mmol) under an argon atmosphere. The mixture is stirred at reflux overnight (18 hrs). After this time, additional 1-isocyanatoethane (42.69 mg, 0.60 mmol) is added. The mixture is stirred at reflux for 24 hours and allowed to stand at room temperature for two days (48 hours). Water (100 μl) and dimethylsulfoxide (5 ml) are added, and the mixture is purified by preparative HPLC.

Yield: 9.7 mg (8% of th.) LC-MS (method 4): $R_t$=4.9 min MS (EI): m/z=571 $(M+H)^+$ $^1$H-NMR (300 MHz, DMSO-$d_6$): δ=0.85 (t, 3H); 1.13-1.26 (m, 6H); 2.01 (s, 3H); 3.95-4.29 (m, 6H); 5.11 (s, 1H); 6.36 (t, 1H); 7.35 (d, 2H); 7.49-7.56 (m, 1H); 7.59 (d, 3H); 7.76-7.83 (m, 3H) ppm.

The following compounds are prepared analogously as described for Example 2:

| Ex-No. | Starting material | Structure | Analytical data |
|---|---|---|---|
| 45 | Example 1A | 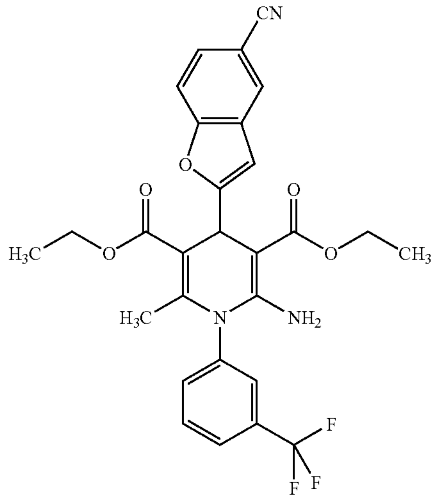 | LC-MS (method 4): $R_t$ = 5.34 min. MS (EI): m/z = 540 $(M + H)^+$ |
| 46 | Example 1A | 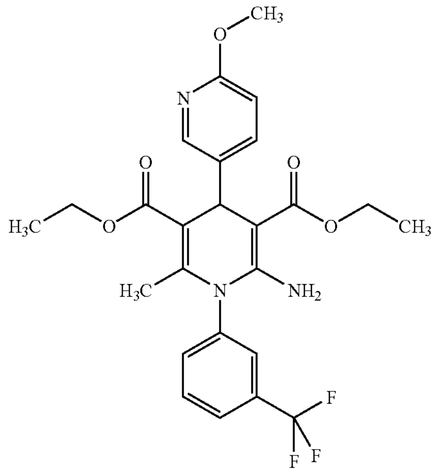 | LC-MS (method 4): $R_t$ = 5.10 min. MS (EI): m/z = 506 $(M + H)^+$ |

Example 47

Diethyl 4-(4-cyanophenyl)-2-(dimethylamino)-6-methyl-1-[3-(trifluoromethyl)-phenyl]-1,4-dihydro-3,5-pyridinedicarboxylate

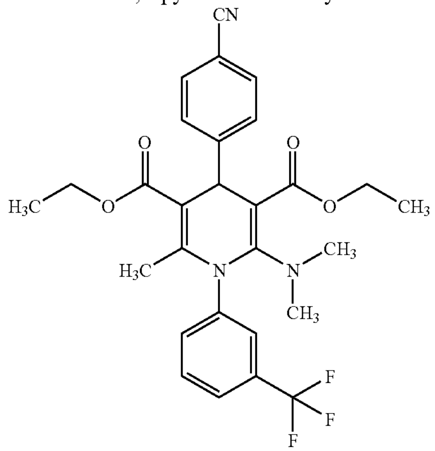

The compound of Example 2 (300 mg, 0.60 mmol) and N-ethyl-N,N-diisopropylamine (170.78 mg, 1.32 mmol) are dissolved in 1,2-dimethoxyethane (7.5 ml) under an argon atmosphere. The mixture is cooled to 0° C. and methyl trifluoromethanesulphonate (216.84 mg, 1.32 mmol) is added. The reaction mixture is stirred at room temperature for 1 hour and then warmed to 50° C. overnight (18 hours). Additional methyl trifluoromethanesulphonate (5 equivalents) and N-ethyl-N,N-diisopropylamine (5 equivalents) are added, and the reaction mixture is stirred at room temperature for 2 hours. The mixture is quenched with water and extracted with ethyl acetate. The aqueous phase is washed with ethyl acetate three times. The organic phases are washed with brine, dried, filtered and the solvent is removed in vacuo. The crude oil is purified by preparative HPLC.

Yield: 143 mg (45% of th.) HPLC (method 8): $R_t$=5.45 min MS (EI): m/z=528 $(M+H)^+$ $^1$H-NMR (300 MHz, DMSO-$d_6$): δ=1.19 (t, 3H); 1.26 (t, 3H); 2.34 (s, 3H); 2.39 (s, 6H); 4.11-4.24 (m, 4H); 4.94 (s, 1H); 6.61 (s, 1H); 7.32 (d, 1H); 7.41 (d, 2H); 7.55-7.68 (m, 2H); 7.75 (d, 2H) ppm.

Example 48

Diethyl 4-(4-cyanophenyl)-2-methyl-6-(methylamino)-1-[3-(trifluoromethyl)phenyl]-1,4-dihydro-3,5-pyridinedicarboxylate

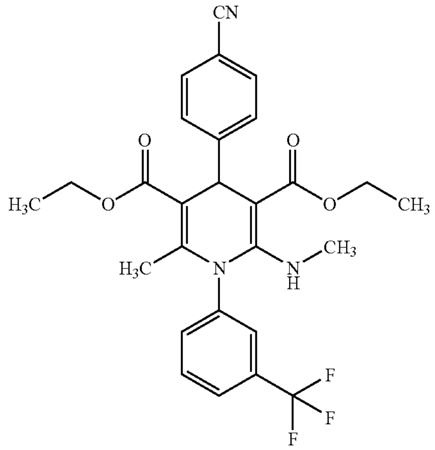

This compound is formed as a by-product in the preparation of Example 47. Yield: 20.4 mg (7% of th.) LC-MS (method 6): $R_t$=4.35 min MS (EI): m/z=514 $(M+H)^+$ $^1$H-NMR (400 MHz, DMSO-$d_6$): δ=1.02-1.09 (m, 6H); 2.09 (s, 3H); 2.64 (s, 3H); 3.97-4.04 (m, 2H); 4.19-4.28 (m, 2H); 4.59 (s, 1H); 4.80 (s, 1H); 7.37-7.49 (m, 2H); 7.58 (d, 2H); 7.70 (d, 2H); 7.80 (d, 2H) ppm.

Example 49

Diethyl 2'-amino-5-cyano-6'-methyl-1'-[3'-(trifluoromethyl)phenyl]-1',4'-dihydro-2,4'-bipyridine-3',5'-dicarboxylate

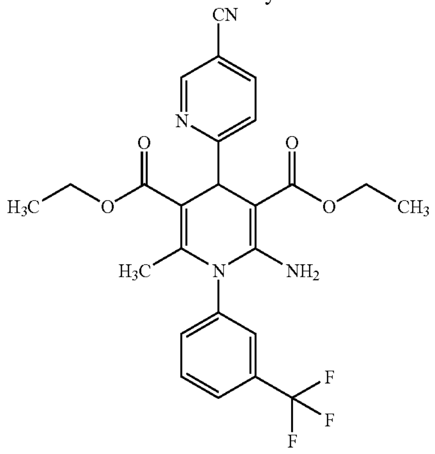

The compounds of Example 1A (280 mg, 0.87 mmol) and of Example 24A (200 mg, 0.87 mmol) are dissolved in ethanol (6 ml). Piperidine (10 mg, 8.6 μl, 0.09 mmol) is added, and the mixture is stirred at 85° C. overnight. The crude reaction mixture is cooled to room temperature, concentrated in vacuo, dissolved in dimethylsulfoxide (5 ml) and purified by preparative HPLC.

Yield: 130 mg (27% of th.) LC-MS (method 6): $R_t$=5.10 min MS (EI): m/z=501 $(M+H)^+$ $^1$H-NMR (300 MHz, DMSO-$d_6$): δ=1.08-1.16 (m, 6H); 1.93 (s, 3H); 3.93-4.09 (m, 4H); 5.03 (s, 1H); 6.78 (br. s, 2H); 7.42 (d, 1H); 7.80-7.93 (m, 4H); 8.18 (dd, 1H); 8.94 (d, 1H) ppm.

Example 50

Ethyl 6-amino-4-(4-cyanophenyl)-5-(4,4-dimethyl-4,5-dihydro-1,3-oxazol-2-yl)-2-methyl-1-[3-(trifluoromethyl)phenyl]-1,4-dihydro-3-pyridinecarboxylate

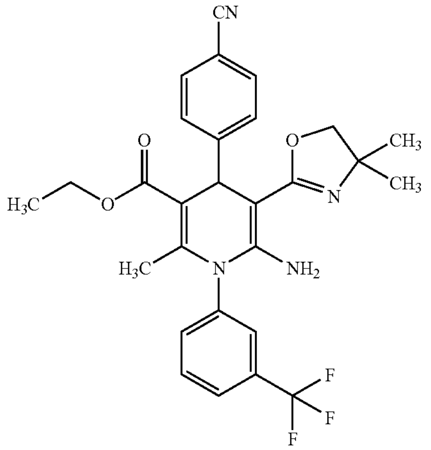

In analogy to Example 49, the compound is prepared from 250 mg (0.59 mmol) of the compound of Example 1A and 150 mg (0.59 mmol) of the compound of Example 25A.

Yield: 21 mg (7% of th.) LC-MS (method 7): $R_t$=2.36 min MS (EI): m/z=525 $(M+H)^+$ $^1$H-NMR (300 MHz, DMSO-$d_6$): δ=1.06-1.18 (m, 9H); 1.96 (s, 3H); 3.69 (d, 1H); 3.86 (d, 1H); 4.03 (q, 2H); 4.98 (s, 1H); 5.74 (s, 1H); 6.74 (br. s, 2H); 7.47 (d, 2H); 7.65 (d, 1H); 7.69-7.79 (m, 3H); 7.89 (d, 1H) ppm.

Example 51

Ethyl 6-amino-5-(1,3-benzothiazol-2-yl)-4-(4-cyanophenyl)-2-methyl-1-[3-(trifluoromethyl)phenyl]-1,4-dihydro-3-pyridinecarboxylate

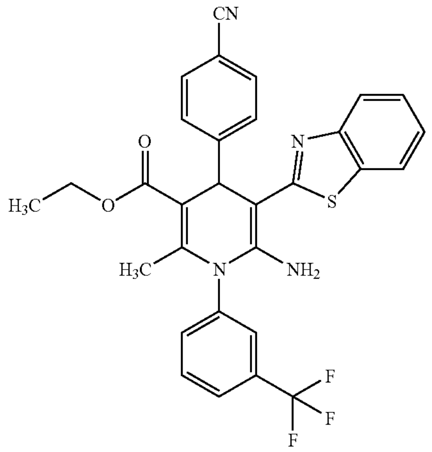

In analogy to Example 49, the compound is prepared from 250 mg (0.59 mmol) of the compound of Example 1A and 170.9 mg (0.59 mmol) of the compound of Example 26A.

Yield: 116 mg (35% of th.) LC-MS (method 6): $R_t$=5.85 min. MS (EI): m/z=561 $(M+H)^+$ $^1$H-NMR (300 MHz, DMSO-$d_6$): δ=1.24 (t, 3H); 1.96 (s, 3H); 4.14 (q, 2H); 5.02 (s, 1H); 7.15 (t, 1H); 7.32 (t, 1H); 7.59 (d, 2H); 7.64 (d, 3H); 7.77 (d, 2H); 7.80-7.87 (m, 3H); 7.95 (d, 2H) ppm.

Example 52

Diethyl 2-amino-4-(4-cyanophenyl)-6-(trifluoromethyl)-1-[3-(trifluoromethyl)phenyl]-1,4-dihydro-3,5-pyridinedicarboxylate

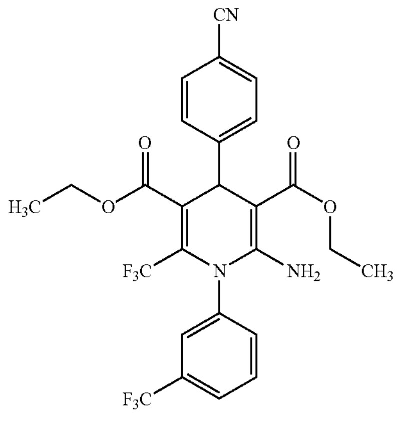

The compound of Example 27A (170 mg, 0.52 mmol) and the compound of Example 28A (117 mg, 0.52 mmol) are dissolved in dioxane (20 ml). 1,8-Diazabicyclo[5.4.0]-undec-7-ene (DBU) (7.91 mg, 0.05 mmol) is added, and the mixture is stirred at 80° C. under an argon atmosphere overnight. The reaction mixture is cooled to room temperature, concentrated in vacuo, dissolved in dimethylsulfoxide (5 ml) and purified by preparative HPLC.

Yield: 13 mg (5% of th.) LC-MS (method 10): $R_t$=4.16 min. MS (EI): m/z=554 $(M+H)^+$ $^1$H-NMR (300 MHz, DMSO-$d_6$): δ=1.04 (t, 3H); 1.11 (t, 3H); 3.94-4.03 (m, 2H); 4.10-4.21 (m, 2H); 4.92 (s, 1H); 7.08 (br.s, 2H); 7.46 (d, 1H); 7.64 (s, 2H); 7.69 (d, 2H); 7.77 (t, 1H); 7.86 (d, 2H) ppm.

Example 53

Diethyl 2-amino-4-(4-cyanophenyl)-5',6-bis(trifluoromethyl)-4H-1,3'-bipyridine-3,5-dicarboxylate

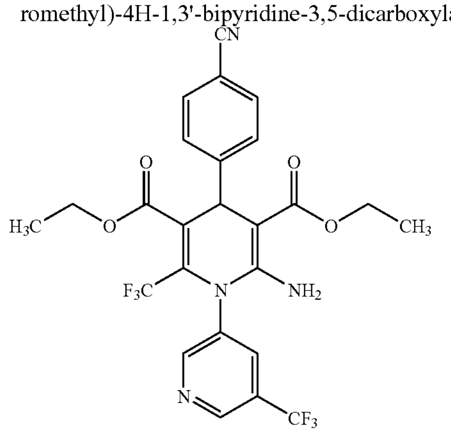

Under Argon, the compound of Example 29A (180 mg, 0.40 mmol) and the compound of Example 28A (90.36 mg, 0.40 mmol) are dissolved in dioxane (5 ml). 1,8-Diazabicyclo [5.4.0]undec-7-ene (DBU) (6.08 mg, 0.04 mmol) is added, and the resulting solution is stirred at 85° C. overnight. The crude mixture is cooled to room temperature and purified directly by preparative HPLC.

Yield: 38 mg (17% of th.) LC-MS (method 7): $R_t$=3.91 min. MS (EI): m/z=555 $(M+H)^+$ $^1$H-NMR (300 MHz, $CDCl_3$): δ=1.14 (dt, 6H); 4.06 (q, 2H); 4.16 (q, 2H); 5.04 (s, 1H); 6.17 (br. s, 2H); 7.42 (d, 2H); 7.66 (d, 2H); 7.82 (s, 1H); 8.79 (s, 1H); 9.01 (s, 1H) ppm.

Example 54

Diethyl 2-amino-6-methyl-4-(5-methyl-1H-imidazolyl)-1-[3-(trifluoromethyl)-phenyl]-1,4-dihydro-3,5-pyridinedicarboxylate

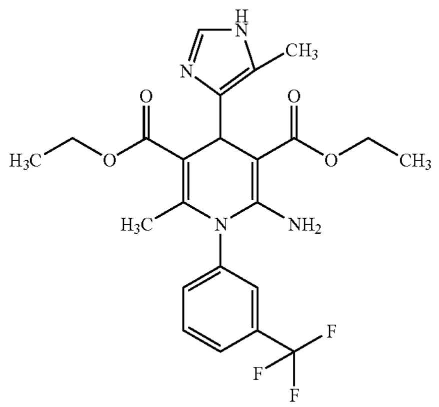

A mixture of 200 mg (0.73 mmol) of Example 1A, 80.6 mg (0.73 mmol) 5-methyl-1H-imidazole-4-carbaldehyde, 82.8 mg (0.73 mmol) ethyl cyanoacetate and 6.23 mg (0.07 mmol) piperidine in 2 ml ethanol is stirred at reflux for 4 hours under an argon atmosphere. 6.23 mg (0.07 mmol) piperidine are added and stirring under reflux is continued overnight. The mixture is allowed to stand at room temperature for 24 hours and is then stirred at reflux for 4 hours. Another 6.23 mg (0.07 mmol) piperidine are added and the mixture is refluxed. After 24 hours, additional 6.23 mg (0.07 mmol) piperidine are added and stirring at reflux is continued for another 8 hours. The solvent is removed in vacuo and the residue is purified by preparative HPLC. 15 mg of impure product are collected and re-purified by column chromatography on silica with dichloromethane/methanol/aq. ammonia 15:1:0.1 as eluent.

Yield: 5.5 mg (1.6% of th.) LC-MS (method 5): $R_t$=3.31 min. HPLC (method 8): $R_t$=4.32 min. MS (EI): m/z=479 $(M+H)^+$ $^1$H-NMR (200 MHz, DMSO-$d_6$): δ=1.17 (t, 6H); 1.91 (s, 3H); 2.21 (s, 3H); 3.88-4.12 (m, 4H); 4.80 and 5.05 (s, 1H); 6.41-6.82 (m, 2H); 7.30 (s, 1H); 7.70-7.96 (m, 2H); 8.05 (d, 1H); 8.42 (d, 1H); 11.41 (s, 1H) ppm.

Example 55

Ethyl 6-amino-5-(aminocarbonyl)-4-(4-cyano-2-methylphenyl)-2-methyl-1-[3-(trifluoromethyl)phenyl]-1,4-dihydro-3-pyridinecarboxylate

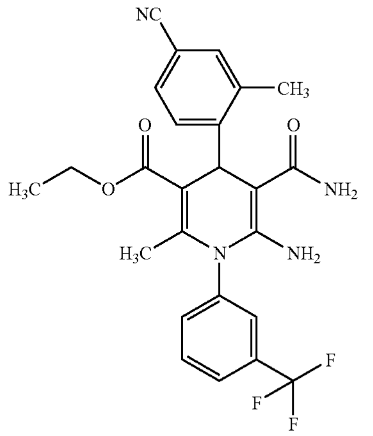

A mixture of 100 mg (0.37 mmol) of Example 1A, 53.12 mg (0.37 mmol) 4-formyl-3-methylbenzonitrile, 30.8 mg (0.37 mmol) 2-cyanoacetamide and 9.35 mg (0.11 mmol) piperidine in 10 ml ethanol is stirred at reflux overnight under an argon atmosphere. The solvent is removed in vacuo and the residue is purified by preparative HPLC. 26.4 mg of impure product are isolated and re-purified by column chromatography on silica with dichloromethane/methanol 50:1 as eluent.

Yield: 16.6 mg (9.2% of th.) LC-MS (method 5): $R_t$=3.62 min. HPLC (method 8): $R_t$=4.26 min. MS (EI): m/z=485 $(M+H)^+$ $^1$H-NMR (mixture of tautomers; 400 MHz, $CDCl_3$): δ=1.10 and 1.20 (t, 3H); 1.89 and 2.17 (s, 3H); 2.48 and 2.52 (s, 3H); 3.49 (m, 1H); 4.02-4.19 (m, 2H); 4.88 (br. s, 1H); 5.06 and 5.23 (s, 1H); 6.40 and 6.66 (br. s, 2H); 7.38-7.60 (m, 5H); 7.68-7.85 (m, 2H) ppm.

Example 56

5-Ethyl 3-[2-(trimethylsilyl)ethyl]2-amino-4-(4-cyanophenyl)-6-methyl-1-[3-(trifluoromethyl)phenyl]-1,4-dihydro-3,5-pyridinedicarboxylate

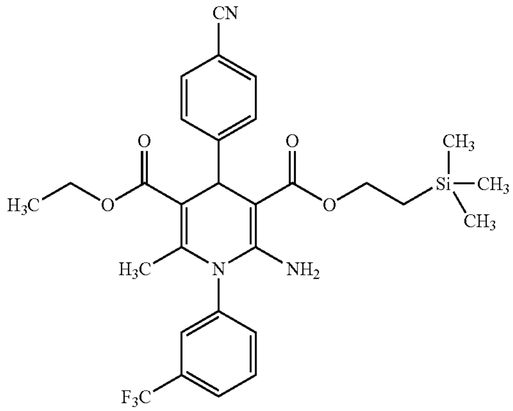

A mixture of 300 mg (1.10 mmol) of Example 1A, 152 mg (1.10 mmol) 4-formylbenzonitrile, 203 mg (1.10 mmol) of Example 38A and 28.1 mg (0.33 mmol) piperidine is stirred at reflux for 24 hours under an argon atmosphere. The solvent is removed in vacuo and the residue is purified by preparative HPLC.

Yield: 163 mg (26% of th.) LC-MS (method 7): $R_t$=4.69 min. HPLC (method 8): $R_t$=5.02 min. MS (EI): m/z=572 $(M+H)^+$ $^1$H-NMR (300 MHz, DMSO-$d_6$): δ=0.00 (s, 9H); 0.81-0.91 (m, 2H); 1.11 (t, 3H); 1.91 (s, 3H); 3.92-4.07 (m, 4H); 5.00 (s, 1H); 6.81 (br. s, 2H); 7.47 (d, 2H); 7.65-7.77 (m, 3H); 7.78-7.86 (m, 2H); 7.90 (d, 1H) ppm.

Example 57

5-[(1S)-2-Methoxy-1-methyl-2-oxoethyl]-3-methyl-2-amino-4-(4-cyanophenyl)-6-methyl-1-[3-(trifluoromethyl)phenyl]-1,4-dihydro-3,5-pyridinedicarboxylate

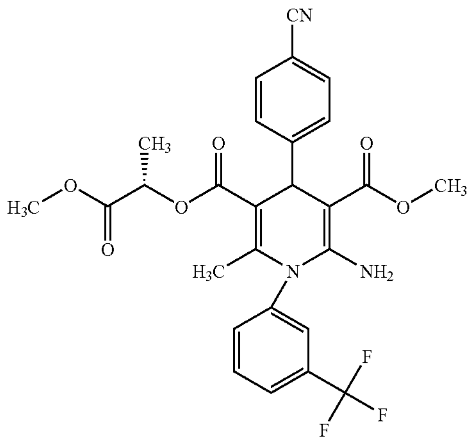

To a solution of 19.82 mg (0.20 mmol) methyl cyanoacetate in 2-butanol (1 ml) are added 26.23 mg (0.20 mmol) 4-formylbenzonitrile and 5.11 mg (0.06 mmol) piperidine. The mixture is stirred at room temperature for 30 minutes. Then 66.26 mg (0.20 mmol) of the compound of Example 8A are added and the reaction mixture is stirred at 80° C. for one hour. After cooling, 500 μl dimethylformamide are added and the mixture is purified by preparative HPLC (column: Macherey Nagel Nucleosil 100-5C18 Nautilus 20 mm×50 mm, 5 μm; solvent A: acetonitrile, solvent B: water; gradient: 0 min 10% A, 2 min 10% A, 6 min 90% A, 7 min 90% A, 7.1 min 10% A, 8 min 10% A; wavelength: 220 nm; injection volume: ca. 500 μl; number of injections: 1). The product containing fractions are combined and concentrated in vacuo.

Yield: 4 mg (3.7% of th.) MS (EI): m/z=544 $(M+H)^+$ $^1$H-NMR (300 MHz, DMSO-$d_6$): δ=1.40 (d, 3H); 2.06 (s, 3H); 3.54 (d, 3H); 3.65 (d, 3H); 4.8-5.0 (m, 2H); 6.84 (br. s, 2H); 7.47-7.54 (m, 4H); 7.74 (d, 2H); 7.80-7.85 (m, 2H); 7.93 (d, 1H) ppm.

Example 58

3-Ethyl 5-[2-(trimethylsilyl)ethyl]2-amino-4-(4-cyanophenyl)-6-methyl-1-[3-(trifluoromethyl)phenyl]-1,4-dihydro-3,5-pyridinedicarboxylate

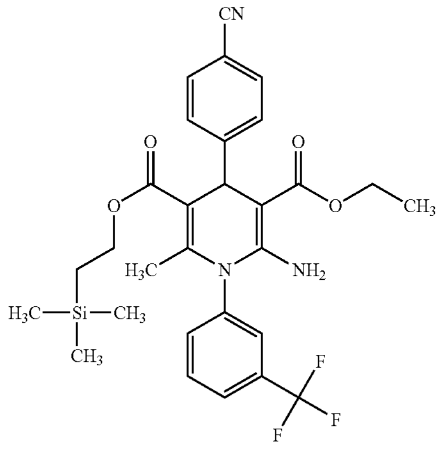

To a solution of 0.68 g (5.15 mmol) 4-cyanobenzaldehyde in 9 ml ethanol are added 0.58 g (5.15 mmol) 2-cyanoethylacetate and 51 μl (0.52 mmol) piperidine. The mixture is stirred at room temperature for one hour, then 1.78 g (5.15 mmol) of the compound of Example 40A are added. The reaction mixture is refluxed for 6.5 hours and stored in a deep-freezer for 48 hours. The precipitate is filtered off, and the mother liquor is purified by preparative HPLC (column: YMC C18 ODS-AQ 250 mm×30 mm, 11 μm; solvent A: acetonitrile, solvent B: water; gradient: 0 min 10% A, 3 min 10% A, 11 min 90% A, 13 min 90% A, 13.2 min 10% A, 15 min 10% A; wavelength: 220 nm; injection volume: ca. 1000 and 2000 μl ethanol solution; number of injections: 7). The product containing fractions are combined and concentrated in vacuo.

Yield: 477 mg (16.2% of th.) MS (EI): m/z=572 $(M)^+$ $^1$H-NMR (200 MHz, DMSO-$d_6$): δ=0.00 (s, 9H); 0.80-0.95 (m, 2H); 1.11 (t, 3H); 1.93 (s, 3H); 3.89-4.20 (m, 4H); 4.99 (s, 1H); 6.84 (br. s, 2H); 7.49 (d, 2H); 7.67-7.9 (m, 5H); 7.93 (d, 1H) ppm.

Example 59

2-(Trimethylsilyl)ethyl-6-amino-5-(aminocarbonyl)-4-(4-cyanophenyl)-2-methyl-1-[3-(trifluoromethyl)phenyl]-1,4-dihydro-3-pyridinecarboxylate

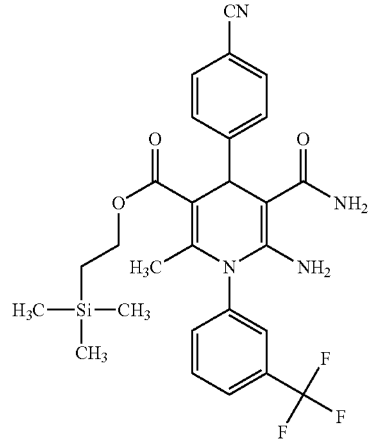

To a solution of 0.45 g (5.40 mmol) 2-cyanoacetamide in 5 ml ethanol are added 0.71 g (5.40 mmol) 4-formylbenzonitrile, a solution of 1.87 g (5.40 mmol) of the compound of Example 40A in 6 ml ethanol and 0.16 g (1.89 mmol) piperidine. The mixture is stirred under reflux for 3.5 hours. The reaction mixture is purified by preparative HPLC (column: YMC C18 ODS-AQ 250 mm×30 mm, 11 μm; solvent A: acetonitrile, solvent B: water; gradient: 0 min 10% A, 3 min 10% A, 11 min 90% A A, 13 min 90% A, 13.2 min 10% A, 15 min 10% A; wavelength: 220 nm; injection volume: ca. 2000 μl; number of injections: 8). The product containing fractions are combined and concentrated in vacuo.

Yield: 741 mg (25% of th.) MS (EI): m/z=543 $(M+H)^+$ 1H-NMR (300 MHz, DMSO-$d_6$): δ=0.00 (s, 9H); 0.86-1.09 (m, 2H); 1.88 (s, 3H); 4.11 (t, 2H); 4.90 (s, 1H); 6.44 (br. s, 2H); 7.03 (br. s, 2H); 7.61 (d, 2H); 7.67 (d, 2H); 7.73-7.82 (m, 3H); 7.89 (d, 1H) ppm.

Example 60

6-Amino-4-(4-cyanophenyl)-5-(ethoxycarbonyl)-2-methyl-1-[3-(trifluoromethyl)-phenyl]-1,4-dihydro-3-pyridinecarboxylic acid

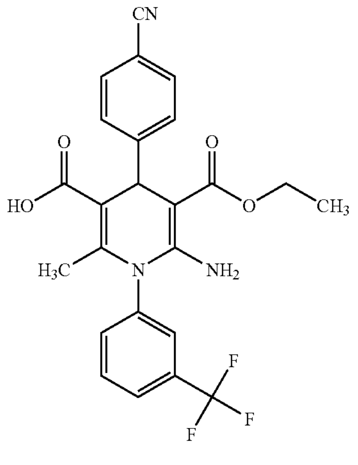

To a solution of 410 mg (0.72 mmol) of the compound of Example 58 in 1.4 ml absolute tetrahydrofuran are added 1.43 ml (1.43 mmol) of a 1 M solution of N,N-tributyl-1-butan-aminiumfluoride in tetrahydrofuran under argon at 0° C. After 5 minutes at 0° C., the reaction mixture is stirred at room temperature overnight. The solvent is removed in vacuo and the residue is purified by column chromatography on silica with dichloromethane/methanol 100:1→100:6 mixtures as eluent. The product containing fractions are combined and concentrated in vacuo. The residue is dissolved in 250 ml ethyl acetate and washed three times with 10% citric acid solution and brine. The organic phase is dried with magnesium sulfate and concentrated in vacuo. Trituration of the residue in ethyl acetate affords the title product.

Yield: 288 mg (85% of th.) MS (EI): m/z=472 $(M+H)^+$ $^1$H-NMR (200 M, DMSO-$d_6$): δ=1.12 (t, 3H); 1.94 (s, 3H); 3.98 (q, 2H); 4.99 (s, 1H); 6.81 (br. s, 2H); 7.49 (d, 2H); 7.65-7.79 (m, 3H); 7.80-7.87 (m, 2H); 7.92 (d, 1H); 12.29 (br. s, 1H) ppm.

Example 61

6-Amino-5-(aminocarbonyl)-4-(4-cyanophenyl)-2-methyl-1-[3-(trifluoromethyl)-phenyl]-1,4-dihydro-3-pyridinecarboxylic acid

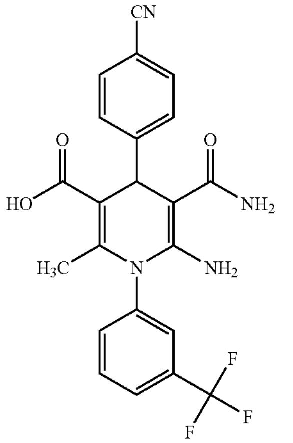

To a solution of 650 mg (1.2 mmol) of the compound of Example 59 in 2.4 ml dimethylformamide are added 1.2 ml (1.2 mmol) of a 1 M solution of tris(dimethylamino)sulfoniumdifluoro(trimethyl)silicate in tetrahydrofuran under argon at 0° C. After stirring the reaction mixture for 15 minutes at 0° C., stirring is continued at room temperature overnight. The reaction mixture is diluted with water and extracted four times with ethyl acetate. The combined organic phases are dried with sodium sulfate and concentrated in vacuo. The residue is purified by preparative HPLC (column: YMC C18 ODS-AQ 250 mm×30 mm, 11 μm; solvent A: acetonitrile, solvent B: water; gradient: 0 min 10% A, 3 min 10% A, 11 min 90% A, 13 min 90% A, 13.2 min 10% A, 15 min 10% A; wavelength: 220 nm; injection volume: ca. 1000 μl and 2000 μl methanol solution; number of injections: 2). The product containing fractions are combined and concentrated in vacuo.

Yield: 112 mg (21% of th.) MS (EI): m/z=443 $(M+M)^+$ $^1$H-NMR (400 MHz, DMSO-$d_6$): δ=1.89 (s, 3H); 4.93 (s, 1H); 6.43 (br. s, 2H); 7.02 (br. s, 2H); 7.58-7.67 (m, 3H); 7.72-7.83 (m, 4H); 7.87 (d, 1H) ppm.

Example 62

Ethyl 2-amino-4-(4-cyanophenyl)-5-{[(2-hydroxyethyl)amino]carbonyl}-6-methyl-1-[3-(trifluoromethyl)phenyl]-1,4-dihydro-3-pyridinecarboxylate

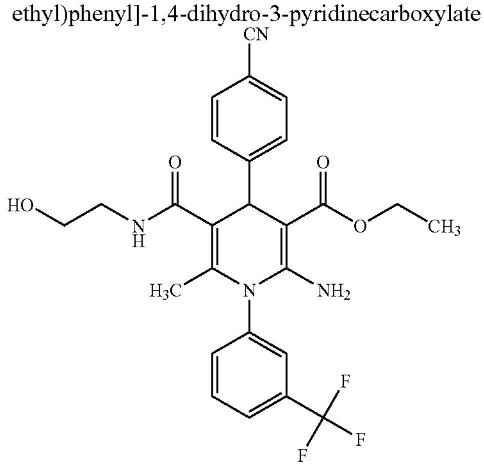

To a solution of 23.57 mg (0.05 mmol) of the compound of Example 60 in 100 μl dimethylformamide 16.22 mg (0.10 mmol) 1-(1H-imidazol-1-ylcarbonyl)-1H-imidazole and 12.22 mg (0.20 mmol) 2-aminoethanol are added. After stirring for 15 minutes, the reaction mixture is allowed to stand at room temperature for two days. The reaction mixture is purified by preparative HPLC (column: Agilent Zorbax Extend C18 20 mm×50 mm, 5 μm; solvent A: acetonitrile, solvent B: water+0.1% triethylamine; gradient: 0 min 10% A, 2 min 10% A, 6 min 90% A, 7 min 90% A, 7.1 min 10% A, 8 min 10% A; wavelength: 220 nm; injection volume: ca 500 μl; number of injections: 1). The product containing fractions are combined and concentrated in vacuo.

Yield: 3.5 mg (14% of th.) MS (EI): m/z=515 $(M+H)^+$ $^1$H-NMR (200 MHz, DMSO-$d_6$): δ=1.00 (t, 3H); 1.53 (s, 3H); 2.95-3.12 (m, 2H); 3.19-3.33 (m, 2H); 3.80-4.01 (m, 2H); 4.56 (t, 1H); 4.80 (s, 1H); 6.85 (br. s, 2H); 7.44 (d, 2H); 7.68-7.77 (m, 6H); 7.90 (d, 1H) ppm.

Example 63

2-Amino-4-(4-cyanophenyl)-5-(1H-imidazol-1-yl-carbonyl)-6-methyl-1-[3-(trifluoromethyl)phenyl]-1,4-dihydro-3-pyridinecarboxamide

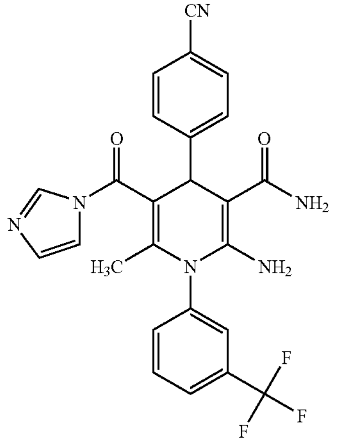

To a solution of 22.1 mg (0.05 mmol) of the compound of Example 61 in 100 μl dimethylformamide 16.22 mg (0.10 mmol) 1-(1H-imidazol-1-ylcarbonyl)-1H-imidazole are added. After stirring at room temperature for two hours, the reaction mixture is purified by preparative HPLC (column: Agilent Zorbax Extend C18 20 mm×50 mm, 5 μm; solvent A: acetonitrile, solvent B: water+0.1% triethylamine; gradient: 0 min 10% A, 2 min 10% A, 6 min 90% A, 7 min 90% A, 7.1 min 10% A, 8 min 10% A; wavelength: 220 nm; injection volume: ca 500 μl; number of injections: 1). The product containing fractions are combined and concentrated in vacuo.

Yield: 3 mg (12% of th.) MS (EI): m/z=493 $(M+H)^+$ $^1$H-NMR (300 MHz, DMSO-$d_6$): δ=1.36 (s, 3H); 4.88 (s, 1H); 6.43 (br. s, 2H); 7.04 (s, 1H); 7.13 (br. s, 2H); 7.55-7.61 (m, 3H, 7.73-7.78 (m, 4H); 7.88 (tr, 1H); 7.93 (s, 1H); 8.17 (s, 1H) ppm.

Example 64

Ethyl 2-amino-4-(4-cyanophenyl)-5-(1H-imidazol-1-ylcarbonyl)-6-methyl-1-[3-(trifluoromethyl)phenyl]-1,4-dihydro-3-pyridinecarboxylate

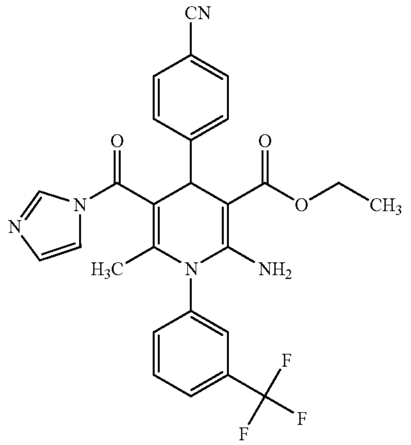

To a solution of 84.8 mg (0.18 mmol) of the compound of Example 60 in 450 μl dimethylformamide 58.3 mg (0.36 mmol) 1-(1H-imidazol-1-ylcarbonyl)-1H-imidazole are added. After stirring for 20 minutes, the reaction mixture is purified by preparative HPLC (column: Agilent Zorbax Extend C18 20 mm×50 mm, 5 μm; solvent A: acetonitrile, solvent B: water+0.1% triethylamine; gradient: 0 min 10% A, 2 min 10% A, 6 min 90% A, 7 min 90% A, 7.1 min 10% A, 8 min 10% A; wavelength: 220 nm; injection volume: ca 500 μl; number of injections: 1). The product containing fractions are combined and concentrated in vacuo.

Yield: 64 mg (68% of th.) MS (EI): m/z=522 $(M+H)^+$ $^1$H-NMR (300 MHz, DMSO-$d_6$): δ=1.01 (t, 3H); 1.36 (s, 3H); 3.91 (q, 2H); 4.84 (s, 1H); 6.95 (br. s, 2H); 7.02 (s, 1H); 7.48 (d, 2H); 7.54 (s, 1H); 7.73 (d, 2H), 7.81 (tr, 2H); 7.92 (d, 1H); 8.08 (s, 1H); 8.20 (s, 1H) ppm.

Example 65

3-Ethyl 5-(2-hydroxyethyl)2-amino-4-(4-cyanophenyl)-6-methyl-1-[3-(trifluoromethyl)phenyl]-1,4-dihydro-3,5-pyridinedicarboxylate

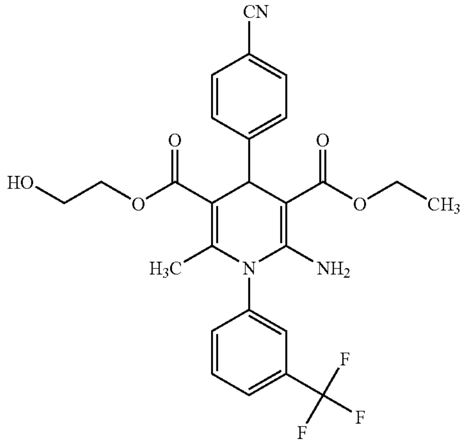

Under argon 28 mg (0.05 mmol) of the compound of Example 64 are dissolved in 1 ml ethylene glycol. After addition of 10 μl triethylamine the mixture is stirred at 100° C. for one hour. The solution is diluted with 500 μl dimethylformamide and is purified by preparative HPLC (column: Agilent Zorbax Extend C18 20 mm×50 mm, 5 μm; solvent A: acetonitrile, solvent B: water+0.1% triethylamine; gradient: 0 min 10% A, 2 min 10% A, 6 min 90% A, 7 min 90% A, 7.1 min 10% A, 8 min 10% A; wavelength: 220 nm; injection volume: ca 750 μl; number of injections: 2). The product containing fractions are combined and concentrated in vacuo.

Yield: 23 mg (83% of th.) MS (EI): m/z=516 $(M+H)^+$ $^1$H-NMR (300 MHz, DMSO-$d_6$): δ=1.08 (t, 3H); 1.91 (s, 3H); 3.52 (q, 2H); 3.87-4.08 (m, 4H); 4.73 (t, 1H); 4.99 (s, 1H); 6.82 (br. s, 2H); 7.52 (d, 2H); 7.72 (d, 3H); 7.82 (tr, 2H); 7.92 (d, 1H) ppm.

Example 66

Ethyl 2-amino-4-(4-cyanophenyl)-5-[(ethylamino)carbonyl]-6-methyl-1-[3-(trifluoromethyl)phenyl]-1,4-dihydro-3-pyridinecarboxylate

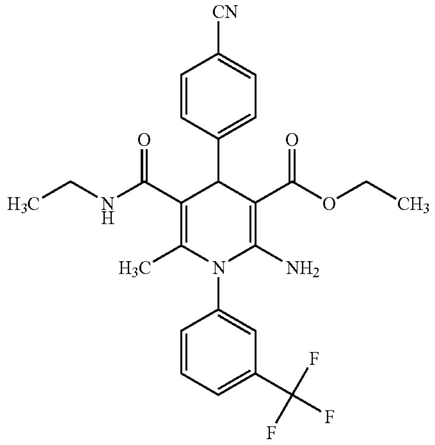

Under argon 64 mg (0.123 mmol) of the compound of Example 64 are dissolved in 1 ml dimethylformamide. After addition of 245 μl (0.245 mmol) of a 2 M solution of ethylamine in tetrahydrofuran, the mixture is stirred at 60° C. for two days. The reaction mixture is purified by preparative HPLC (column: Agilent Zorbax Extend C18 20 mm×50 mm, 5 μm; solvent A: acetonitrile, solvent B: water+0.1% triethylamine; gradient: 0 min 10% A, 2 min 10% A, 6 min 90% A, 7 min 90% A, 7.1 min 10% A, 8 min 10% A; wavelength: 220 nm; injection volume: ca 500 μl; number of injections: 1). The product containing fractions are combined and concentrated in vacuo.

Yield: 14.1 mg (23% of th.) MS (EI): m/z=499 $(M+H)^+$ $^1$H-NMR (200 MHz, DMSO-$d_6$): δ=0.85 (t, 3H); 1.05 (t, 3H); 1.51 (s, 3H); 2.98 (quin, 2H); 3.88 (m, 2H); 4.80 (s, 1H); 6.85 (br. s, 2H); 7.43 (d, 2H); 7.70-7.77 (m, 5H); 7.82 (tr, 1H); 7.91 (d, 1H) ppm.

The following compounds are prepared analogously as described for Example 57:

| Ex.-No. | Starting material | Structure | Yield [%] | Analytical data |
| --- | --- | --- | --- | --- |
| 67 | Example 41A | 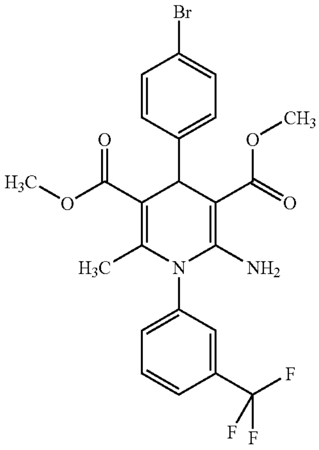 | 3.8 | LC-MS (method 1): $R_t$ = 5.40 min. MS (EI): m/z = 525 $(M + H)^+$ |
| 68 | Example 41A | 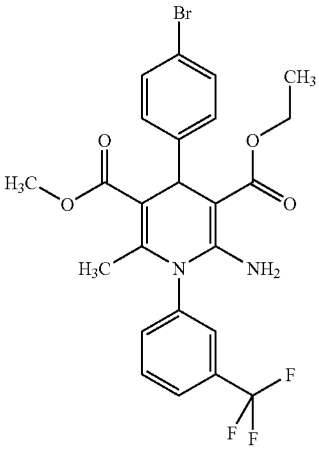 | 8.3 | LC-MS (method 1): $R_t$ = 5.55 min. MS (EI): m/z = 539 $(M + H)^+$ |

-continued
| Ex.-No. | Starting material | Structure | Yield [%] | Analytical data |
| --- | --- | --- | --- | --- |
| 69 | Example 41A | 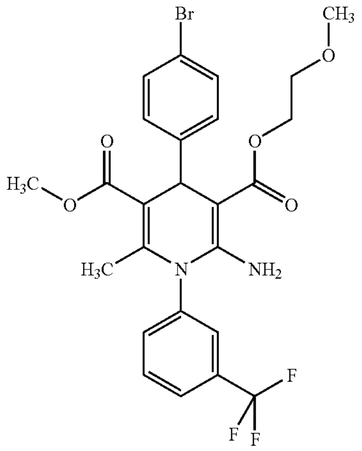 | 15.4 | LC-MS (method 1): $R_t$ = 5.69 min. MS (EI): m/z = 553 $(M + H)^+$ |
| 70 | Example 41A | 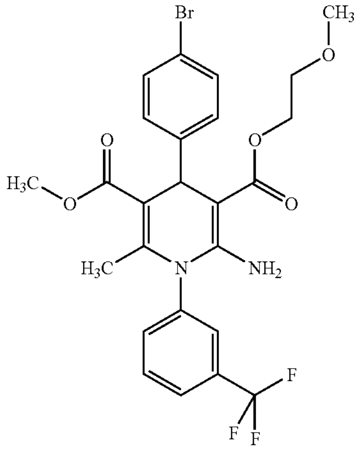 | 2.6 | LC-MS (method 1): $R_t$ = 5.34 min. MS (EI): m/z = 569 $(M + H)^+$ |
| 71 | Example 41A | 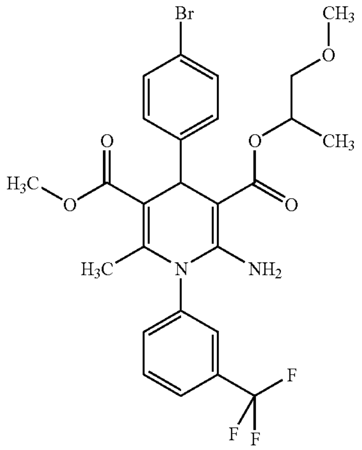 | 6.0 | LC-MS (method 1): $R_t$ = 5.50 min. MS (EI): m/z = 583 $(M + H)^+$ |

-continued
| Ex.-No. | Starting material | Structure | Yield [%] | Analytical data |
| --- | --- | --- | --- | --- |
| 72 | Example 41A | 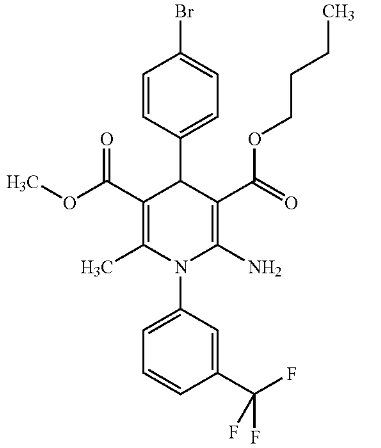 | 7.1 | LC-MS (method 1): $R_t$ = 5.89 min. MS (EI): m/z = 567 $(M + H)^+$ |
| 73 | Example 41A | 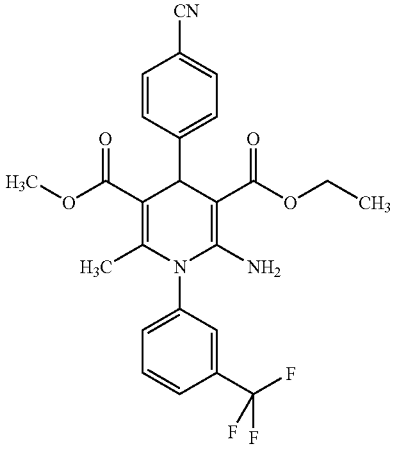 | 11.3 | LC-MS (method 1): $R_t$ = 5.10 min. MS (EI): m/z = 486 $(M + H)^+$ |
| 74 | Example 41A | 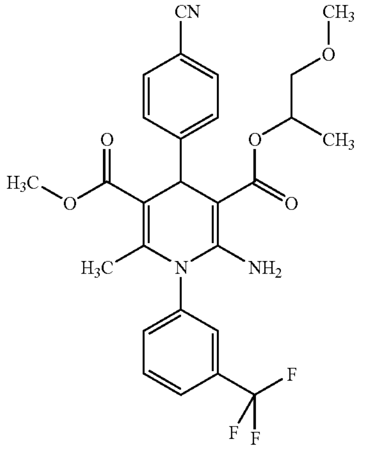 | 11.3 | LC-MS (method 1): $R_t$ = 5.04 min. MS (EI): m/z = 530 $(M + H)^+$ |

-continued
| Ex.-No. | Starting material | Structure | Yield [%] | Analytical data |
|---|---|---|---|---|
| 75 | Example 41A | 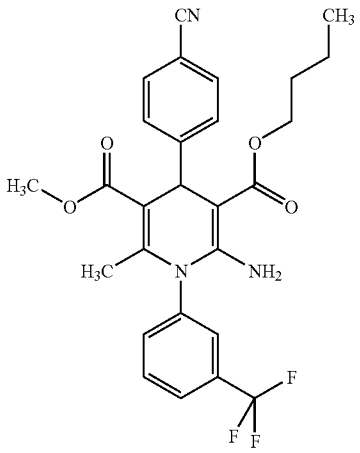 | 13.6 | LC-MS (method 1): $R_t$ = 5.42 min. MS (EI): m/z = 514 $(M + H)^+$ |
| 76 | Example 1A | 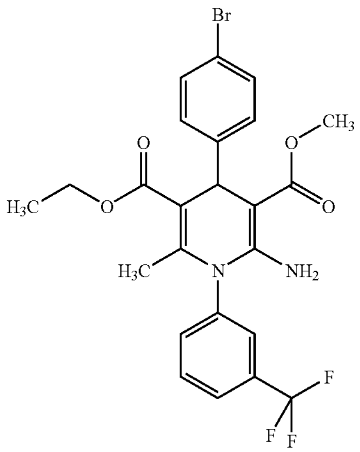 | 3.7 | LC-MS (method 1): $R_t$ = 5.57 min. MS (EI): m/z = 539 $(M + H)^+$ |
| 77 | Example 1A | 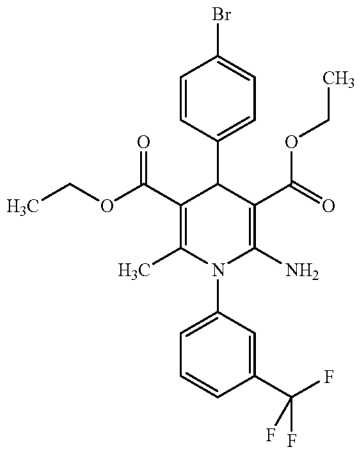 | 4.5 | LC-MS (method 1): $R_t$ = 5.72 min. MS (EI): m/z = 553 $(M + H)^+$ |

-continued
| Ex.-No. | Starting material | Structure | Yield [%] | Analytical data |
|---|---|---|---|---|
| 78 | Example 1A | 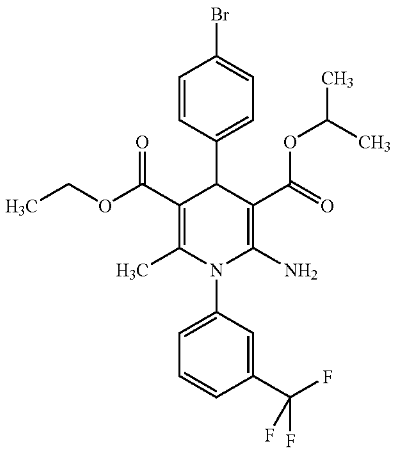 | 8.8 | LC-MS (method 1): $R_t$ = 5.87 min. MS (EI): m/z = 567 $(M + H)^+$ |
| 79 | Example 1A | 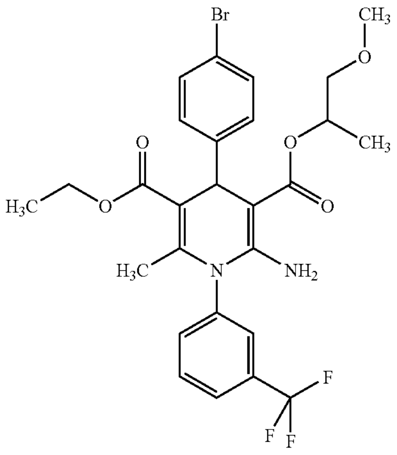 | 5.0 | LC-MS (method 1): $R_t$ = 5.67 min. MS (EI): m/z = 597 $(M + H)^+$ |
| 80 | Example 1A | 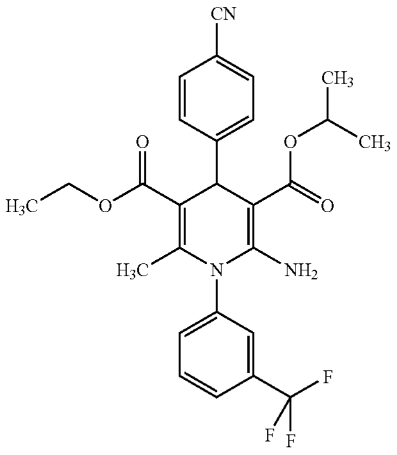 | 27.3 | LC-MS (method 1): $R_t$ = 5.42 min. MS (EI): m/z = 514 $(M + H)^+$ |

-continued
| Ex.-No. | Starting material | Structure | Yield [%] | Analytical data |
|---|---|---|---|---|
| 81 | Example 1A | 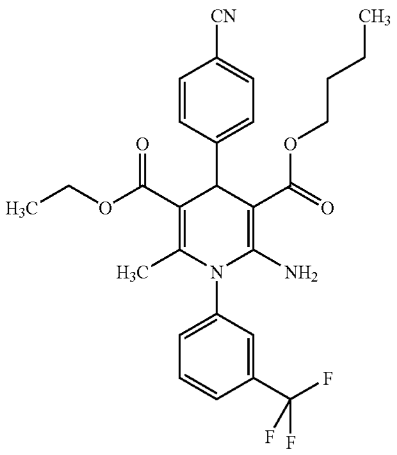 | 11.4 | LC-MS (method 1): $R_t$ = 5.59 min. MS (EI): m/z = 528 $(M + H)^+$ |
| 82 | Example 42A | 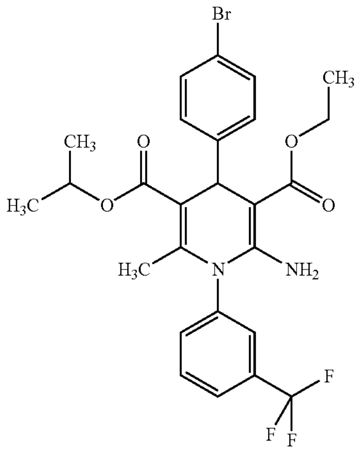 | 2.6 | LC-MS (method 1): $R_t$ = 5.89 min. MS (EI): m/z = 567 $(M + H)^+$ |
| 83 | Example 42A | 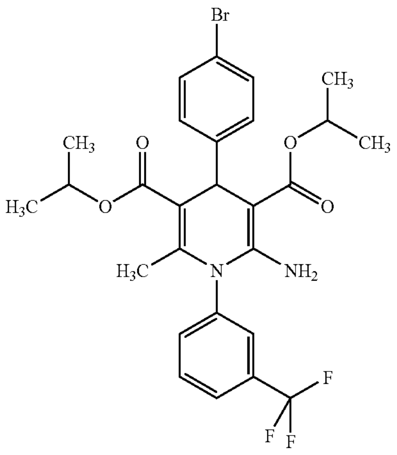 | 11.2 | LC-MS (method 1): $R_t$ = 6.05 min. MS (EI): m/z = 581 $(M + H)^+$ |

-continued
| Ex.-No. | Starting material | Structure | Yield [%] | Analytical data |
|---|---|---|---|---|
| 84 | Example 42A | 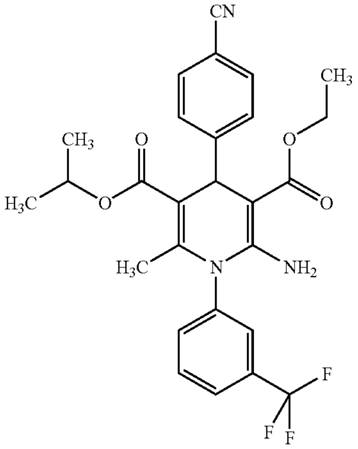 | 4.9 | LC-MS (method 1): $R_t$ = 5.43 min. MS (EI): m/z = 514 $(M + H)^+$ |
| 85 | Example 42A | 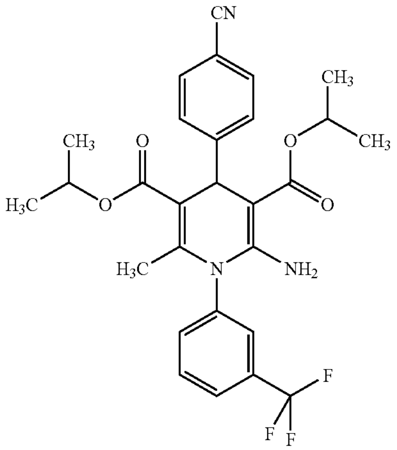 | 17.1 | LC-MS (method 1): $R_t$ = 5.56 min. MS (EI): m/z = 528 $(M + H)^+$ |
| 86 | Example 42A | 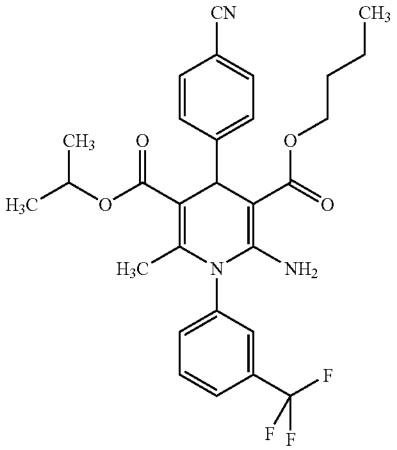 | 3.7 | LC-MS (method 1): $R_t$ = 5.74 min. MS (EI): m/z = 542 $(M + H)^+$ |

-continued
| Ex.-No. | Starting material | Structure | Yield [%] | Analytical data |
|---|---|---|---|---|
| 87 | Example 43A | 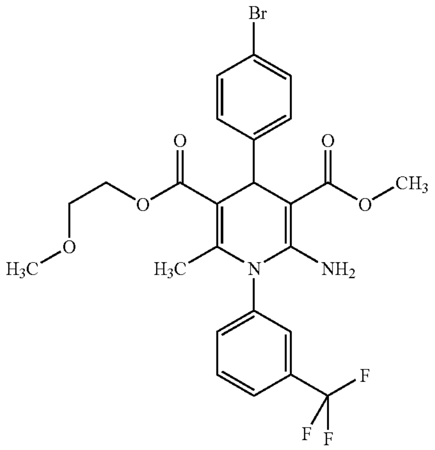 | 2.6 | LC-MS (method 1): $R_t$ = 5.33 min. MS (EI): m/z = 569 $(M + H)^+$ |
| 88 | Example 43A | 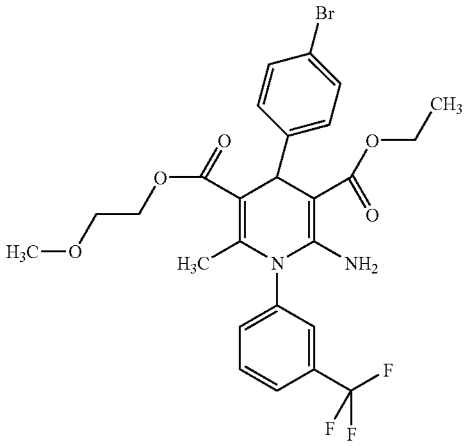 | 6.9 | LC-MS (method 1): $R_t$ = 5.49 min. MS (EI): m/z = 583 $(M + H)^+$ |
| 89 | Example 43A | 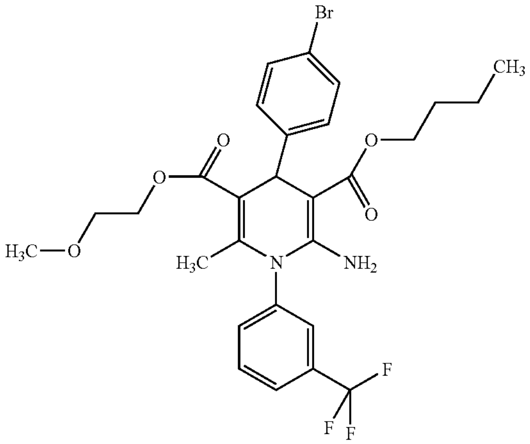 | 4.9 | LC-MS (method 1): $R_t$ = 5.82 min. MS (EI): m/z = 611 $(M + H)^+$ |

-continued
| Ex.-No. | Starting material | Structure | Yield [%] | Analytical data |
|---|---|---|---|---|
| 90 | Example 43A | 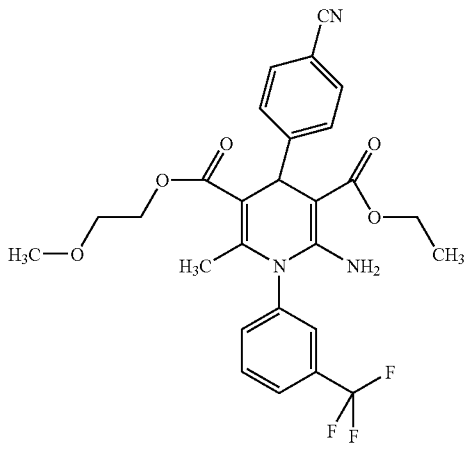 | 6.6 | LC-MS (method 1): $R_t$ = 5.05 min. MS (EI): m/z = 530 $(M + H)^+$ |
| 91 | Example 43A | 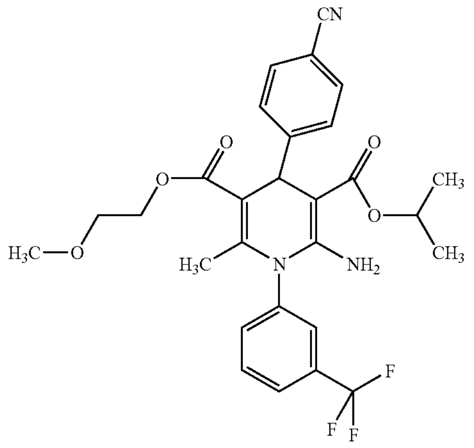 | 25.8 | LC-MS (method 1): $R_t$ = 5.19 min. MS (EI): m/z = 544 $(M + H)^+$ |
| 92 | Example 43A | 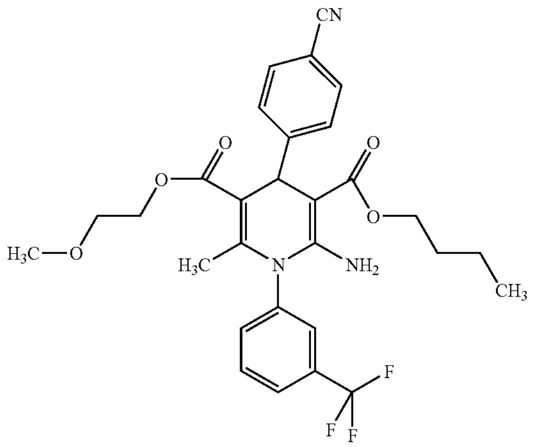 | 13.5 | LC-MS (method 1): $R_t$ = 5.36 min. MS (EI): m/z = 558 $(M + H)^+$ |

-continued
| Ex.-No. | Starting material | Structure | Yield [%] | Analytical data |
|---|---|---|---|---|
| 93 | Example 8A | 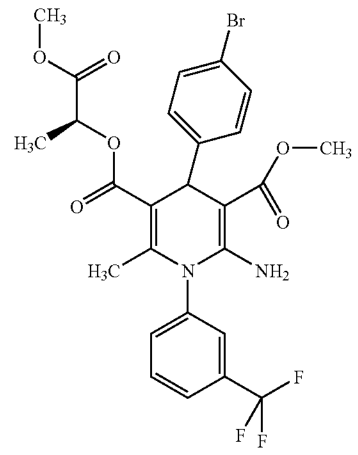 | 5.9 | LC-MS (method 1): $R_t$ = 5.40 min. MS (EI): m/z = 597 $(M + H)^+$ |
| 94 | Example 8A | 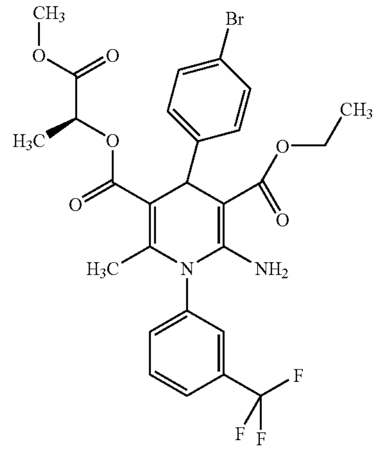 | 11.5 | LC-MS (method 1): $R_t$ = 5.55 min. MS (EI): m/z = 611 $(M + H)^+$ |
| 95 | Example 8A | 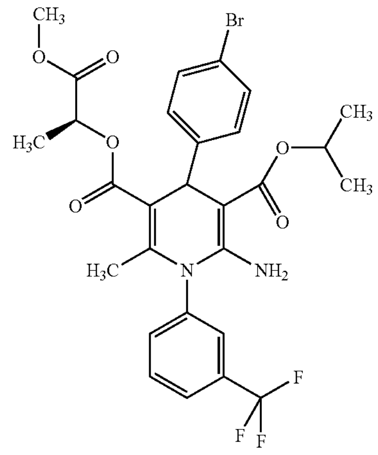 | 11.2 | LC-MS (method 1): $R_t$ = 5.68 min. MS (EI): m/z = 625 $(M + H)^+$ |

-continued
| Ex.-No. | Starting material | Structure | Yield [%] | Analytical data |
| --- | --- | --- | --- | --- |
| 96 | Example 8A | 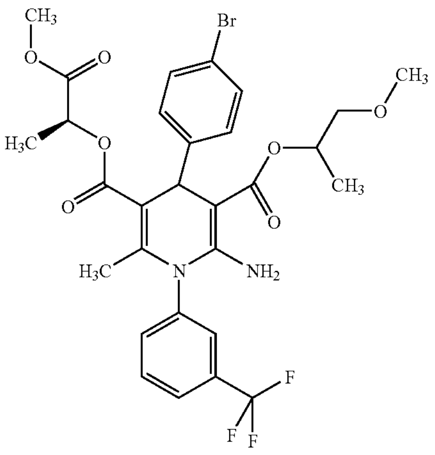 | 5.3 | LC-MS (method 1): $R_t$ = 5.50 min. MS (EI): m/z = 655 $(M + H)^+$ |
| 97 | Example 8A | 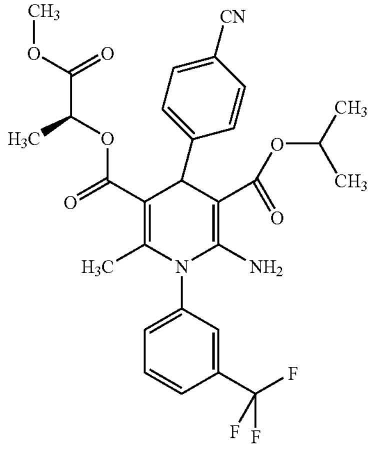 | 26.2 | LC-MS (method 1): $R_t$ = 5.27 min. MS (EI): m/z = 572 $(M + H)^+$ |
| 98 | Example 8A | 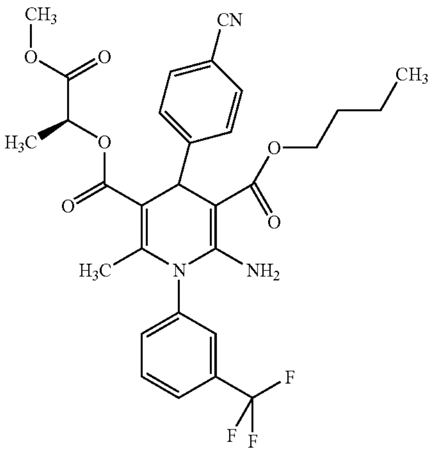 | 25.6 | LC-MS (method 1): $R_t$ = 5.42 min. MS (EI): m/z = 586 $(M + H)^+$ |

-continued
| Ex.-No. | Starting material | Structure | Yield [%] | Analytical data |
| --- | --- | --- | --- | --- |
| 99 | Example 41A | 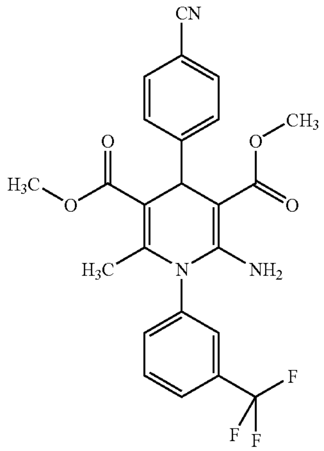 | 2.4 | LC-MS (method 1): $R_t$ = 4.95 min. MS (EI): m/z = 472 $(M + H)^+$ |
| 100 | Example 41A | 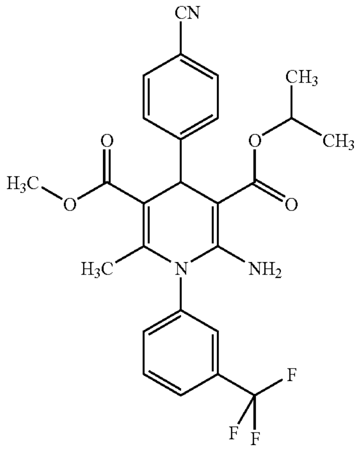 | 1.9 | LC-MS (method 1): $R_t$ = 5.25 min. MS (EI): m/z = 500 $(M + H)^+$ |
| 101 | Example 41A | 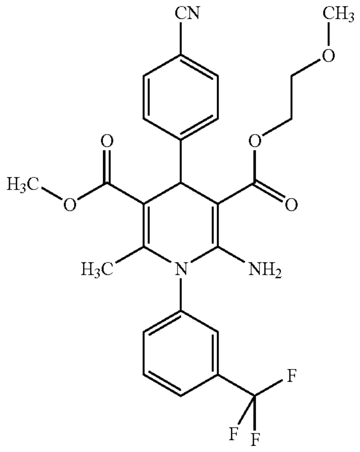 | 1.9 | LC-MS (method 1): $R_t$ = 4.92 min. MS (EI): m/z = 516 $(M + H)^+$ |

-continued
| Ex.-No. | Starting material | Structure | Yield [%] | Analytical data |
|---|---|---|---|---|
| 102 | Example 1A | 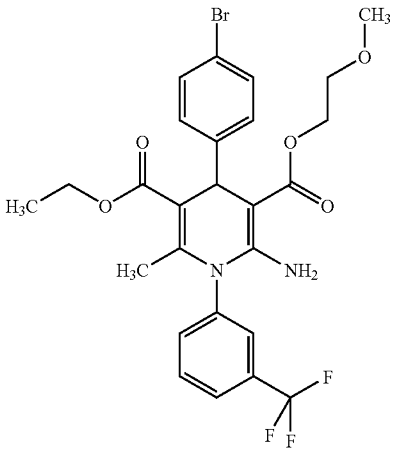 | 1.3 | LC-MS (method 1): $R_t$ = 5.51 min. MS (EI): m/z = 583 $(M + H)^+$ |
| 103 | Example 1A | 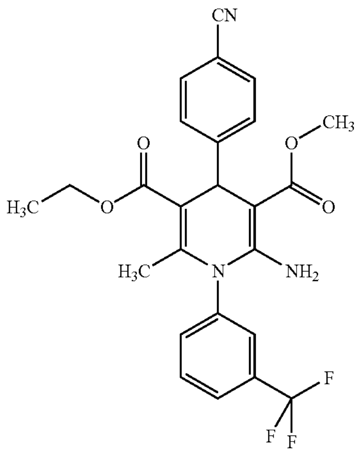 | 2.6 | LC-MS (method 1): $R_t$ = 5.12 min. MS (EI): m/z = 486 $(M + H)^+$ |
| 104 | Example 42A | 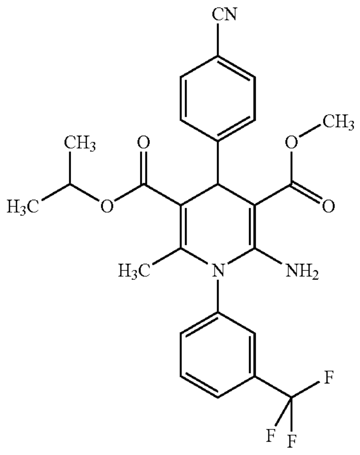 | 0.8 | LC-MS (method 1): $R_t$ = 5.27 min. MS (EI): m/z = 500 $(M + H)^+$ |

-continued
| Ex.-No. | Starting material | Structure | Yield [%] | Analytical data |
|---|---|---|---|---|
| 105 | Example 42A | 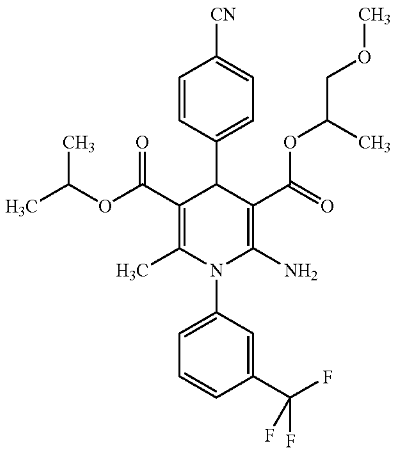 | 1.5 | LC-MS (method 1): $R_t$ = 5.35 min. MS (EI): m/z = 557 $(M + H)^+$ |
| 106 | Example 42A | 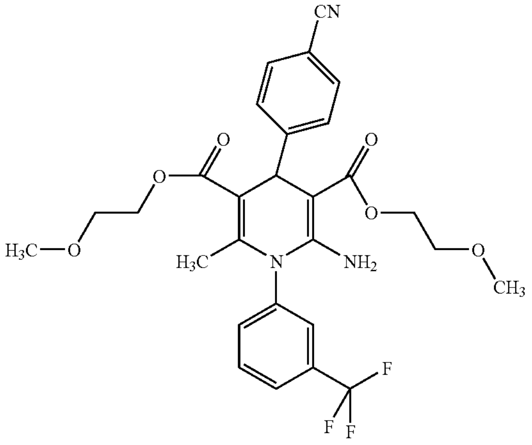 | 1.4 | LC-MS (method 1): $R_t$ = 4.87 min. MS (EI): m/z = 560 $(M + H)^+$ |
| 107 | Example 8A | 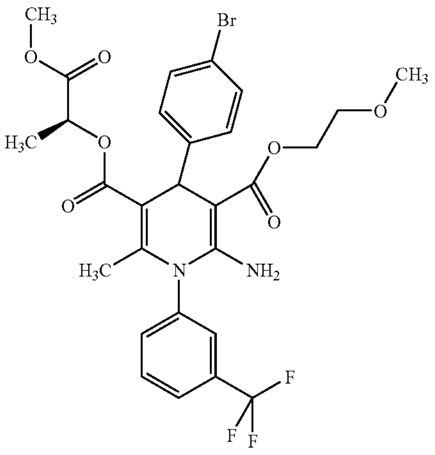 | 0.6 | LC-MS (method 1): $R_t$ = 5.35 min. MS (EI): m/z = 641 $(M + H)^+$ |

-continued

| Ex.-No. | Starting material | Structure | Yield [%] | Analytical data |
|---|---|---|---|---|
| 108 | Example 8A | 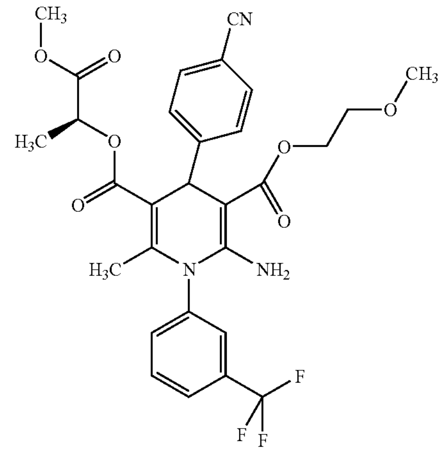 | 1.0 | LC-MS (method 1): $R_t$ = 4.98 min. MS (EI): m/z = 588 $(M + H)^+$ |

C. OPERATIVE EXAMPLES RELATING TO PHARMACEUTICAL COMPOSITIONS

The compounds according to the invention can be converted into pharmaceutical preparations as follows:

Tablet:

Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension:

Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

We claim:

1. A compound of formula (I)

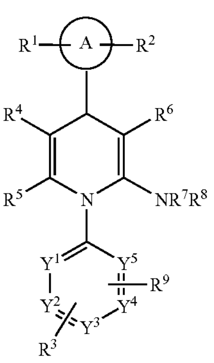

wherein

A represents an aryl or heteroaryl ring, $R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents $C_1$-$C_6$-alkoxycarbonyl, $C_1$-$C_6$-alkenoxycarbonyl, hydroxycarbonyl, aminocarbonyl, mono- or di-$C_1$-$C_4$-alkylaminocarbonyl, $C_6$-$C_{10}$-arylaminocarbonyl, heteroarylcarbonyl, heterocyclylcarbonyl or cyano, wherein $C_1$-$C_6$-alkoxycarbonyl, mono- and di-$C_1$-$C_4$-alkylaminocarbonyl can be substituted with one to three identical or different radicals selected from the group consisting of hydroxy, $C_1$-$C_4$-alkoxy, hydroxycarbonyl, $C_1$-$C_4$-alkoxycarbonyl, amino, mono- and di-$C_1$-$C_4$-alkylamino, aminocarbonyl, mono- and di-$C_1$-$C_4$-alkylaminocarbonyl, $C_1$-$C_4$-alkylcarbonylamino, heteroaryl, heterocyclyl and tri-($C_1$-$C_6$-alkyl)-silyl, $R^5$ represents $C_1$-$C_4$-alkyl, which can be substituted with one to three identical or different radicals selected from the group consisting of halogen, hydroxy, $C_1$-$C_6$-alkoxy, $C_1$-$C_6$-alkenoxy, $C_1$-$C_6$-alkylthio, amino, mono- and di-$C_1$-$C_6$-alkylamino, hydroxycarbonyl, $C_1$-$C_6$-alkoxycarbonyl and the radical —O—($C_1$-$C_4$)-alkyl-O—($C_1$-$C_4$)-alkyl, or $R^5$ represents $C_1$-$C_6$-alkoxycarbonyl, $R^6$ represents cyano, aminocarbonyl, mono- or di-$C_1$-$C_4$-alkylaminocarbonyl, $C_3$-$C_8$-cycloalkylaminocarbonyl, $C_1$-$C_6$-alkylcarbonyl, hydroxycarbonyl, $C_1$-$C_6$-alkoxycarbonyl, heteroaryl, heterocyclyl, heteroarylcarbonyl or heterocyclylcarbonyl, wherein mono- and di-$C_1$-$C_4$-alkylaminocarbonyl, $C_1$-$C_6$-alkylcarbonyl, $C_1$-$C_6$-alkoxycarbonyl, heteroaryl, heterocyclyl, heteroarylcarbonyl and heterocyclylcarbonyl can be substituted with one to three identical or different radicals selected from the group consisting of $C_1$-$C_4$-alkyl, hydroxy, $C_1$-$C_4$-alkoxy, hydroxycarbonyl, $C_1$-$C_4$-alkoxycarbonyl, amino, mono- and di-$C_1$-$C_4$-alkylamino, aminocarbonyl, mono- and di-$C_1$-$C_4$-alkylaminocarbonyl, $C_1$-$C_4$-alkylcarbonylamino, tri-($C_1$-$C_6$-alkyl)-silyl, phenyl and heteroaryl, $R^7$ represents hydrogen, $C_1$-$C_6$-alkyl, aminocarbonyl, mono- or di-$C_1$-$C_6$-alkyl-aminocarbonyl or $C_1$-$C_6$-alkoxycarbonyl, $R^8$ represents hydrogen or $C_1$-$C_6$-alkyl, $R^9$ represents nitro, trifluoromethyl, or $C_1$-$C_6$-alkyl, and $Y^1$, $Y^2$, $Y^3$, $Y^4$ and $Y^5$ independently from each other represent CH or N, wherein the ring contains either 0, 1 or 2 nitrogen atoms.

2. A compound of formula (I) according to claim 1, wherein

A represents an aryl ring, $R^1$, $R^2$ and $R^3$ independently from each other represent hydrogen, methyl, ethyl, fluoro, chloro, bromo, nitro, cyano, trifluoromethyl or trifluoromethoxy, $R^4$ represents $C_1$-$C_6$-alkoxycarbonyl, $C_1$-$C_6$-alkenoxycarbonyl, hydroxycarbonyl, aminocarbonyl, mono- or di-$C_1$-$C_4$-alkylaminocarbonyl, heteroarylcarbonyl or cyano, wherein $C_1$-$C_6$-alkoxycarbonyl, mono- and di-$C_1$-$C_4$-alkylaminocarbonyl can be substituted with one to three identical or different radicals selected from the group consisting of hydroxy, $C_1$-$C_4$-alkoxy, $C_1$-$C_4$-alkoxycarbonyl, amino, mono- and di-$C_1$-$C_4$-alkylamino, heterocyclyl or tri-($C_1$-$C_6$-alkyl)-silyl, $R^5$ represents $C_1$-$C_4$-alkyl, which can be substituted with one to three identical or different radicals selected from the group consisting of halogen, $C_1$-$C_6$-alkoxy, $C_1$-$C_6$-alkenoxy, $C_1$-$C_6$-alkylthio and the radical —O—($C_1$-$C_4$)-alkyl-O—($C_1$-$C_4$)-alkyl, or $R^5$ represents $C_1$-$C_6$-alkoxycarbonyl, $R^6$ represents cyano, aminocarbonyl, mono- or di-$C_1$-$C_4$-alkylaminocarbonyl, $C_3$-$C_8$-cycloalkylaminocarbonyl, $C_1$-$C_6$-alkylcarbonyl, hydroxycarbonyl, $C_1$-$C_6$-alkoxycarbonyl, heteroaryl or heterocyclyl, wherein mono- and di-$C_1$-$C_4$-alkylaminocarbonyl, $C_1$-$C_6$-alkylcarbonyl, $C_1$-$C_6$-alkoxycarbonyl, heteroaryl and heterocyclyl can be substituted with one to three identical or different radicals selected from the group consisting of hydroxy, $C_1$-$C_4$-alkoxy and tri-($C_1$-$C_6$-alkyl)-silyl, or $R^6$ represents a moiety of the formula

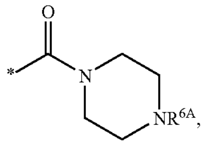

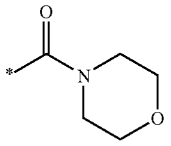

or

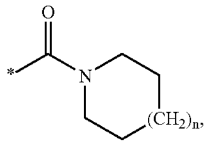

wherein $R^{6A}$ is selected from the group consisting of hydrogen and $C_1$-$C_6$-alkyl, and n represents an integer of 1 or 2, $R^7$ represents hydrogen, $C_1$-$C_6$-alkyl, aminocarbonyl or mono- or di-$C_1$-$C_6$-alkyl-aminocarbonyl, $R^8$ represents hydrogen or $C_1$-$C_6$-alkyl, $R^9$ represents nitro, trifluoromethyl, methyl or ethyl, and $Y^1$, $Y^2$, $Y^3$, $Y^4$ and $Y^5$ each represent CH.

3. A compound of formula (I) according to claim 1 or 2, wherein A is phenyl.

4. A compound of formula (I) according to claim 1 or 2, wherein $R^1$ is hydrogen.

5. A compound of formula (I) according to claim 1 or 2, wherein $R^2$ is cyano.

6. A compound of formula (I) according to claim 1 or 2, wherein $R^3$ is hydrogen.

7. A compound of formula (I) according to claim 1 or 2, wherein $R^4$ is $C_1$-$C_6$-alkoxycarbonyl or cyano.

8. A compound of formula (I) according to claim 1 or 2, wherein $R^5$ is methyl.

9. A compound of formula (I) according to claim 1 or 2, wherein $R^6$ is cyano, aminocarbonyl, mono- or di-methyl- or -ethylaminocarbonyl, methoxycarbonyl or ethoxycarbonyl.

10. A compound of formula (I) according to claim 1 or 2, wherein $R^7$ and/or $R^8$ is hydrogen.

11. A compound of formula (I) according to claim 1 or 2, wherein $R^9$ is trifluoromethyl or nitro.

12. A compound according to claim 1 or 2, wherein said compound is a compound of formula (II):

(II)

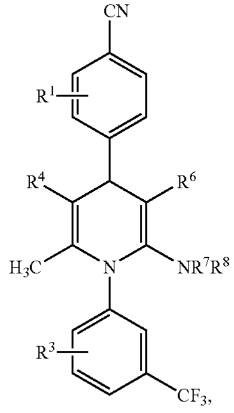

wherein $R^1$, $R^3$, $R^4$, $R^6$, $R^7$ and $R^8$ have the meaning indicated in claim 1 or 2.

13. A process for synthesizing a compound of formula (I) according to claim 1 or 2, wherein $R^7$ and $R^8$ represent hydrogen, by condensing a compound of formula (III)

(III)

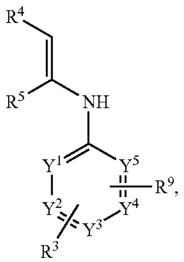

wherein $R^3$, $R^4$, $R^5$, $R^9$, and $Y^1$ to $Y^5$ have the meaning described in claim 1 or 2, in the presence of a base, with a compound of formula (IV) and a compound of formula (V)

(IV)

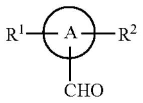

-continued (V)

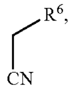

wherein $R^1$, $R^2$, $R^6$ and A have the meaning described in claim 1 or 2.

14. The composition containing at least one compound of formula (I) according to claim 1 or 2 and a pharmacologically acceptable diluent.

15. A process for the preparation of a composition containing at least one compound of formula (I) according to claim 1 and a pharmacologically acceptable diluent, said process comprising bringing said compound of formula (I) and customary auxiliaries into a suitable application form.

16. A method of treating acute and chronic inflammatory, ischaemic or remodelling processes, comprising administering a therapeutically effective amount of a compound according to claim 1.

17. The method of claim 16, wherein the acute and chronic inflammatory, ischaemic or remodelling process is selected from chronic obstructive pulmonary disease, acute coronary syndrome, acute myocardial infarction or development of heart failure.

* * * * *